(12) United States Patent
Bassaganya-Riera et al.

(10) Patent No.: US 11,459,310 B2
(45) Date of Patent: Oct. 4, 2022

(54) LANCL LIGANDS

(71) Applicant: Landos Biopharma, Inc., Blacksburg, VA (US)

(72) Inventors: Josep Bassaganya-Riera, Blacksburg, VA (US); Andrew Leber, Blacksburg, VA (US); Raquel Hontecillas, Blacksburg, VA (US)

(73) Assignee: LANDOS BIOPHARMA, INC., Blacksburg, VA (US)

( * ) Notice: Subject to any disclaimer, the term of this patent is extended or adjusted under 35 U.S.C. 154(b) by 0 days.

(21) Appl. No.: 17/506,453

(22) Filed: Oct. 20, 2021

(65) Prior Publication Data
US 2022/0127250 A1 Apr. 28, 2022

Related U.S. Application Data

(60) Provisional application No. 63/104,109, filed on Oct. 22, 2020.

(51) Int. Cl.
| | |
|---|---|
| C07D 401/14 | (2006.01) |
| C07D 413/14 | (2006.01) |
| A61P 17/06 | (2006.01) |
| A61P 1/16 | (2006.01) |
| A61P 37/06 | (2006.01) |
| A61P 3/04 | (2006.01) |
| A61P 19/02 | (2006.01) |
| A61P 3/10 | (2006.01) |
| A61P 1/00 | (2006.01) |

(52) U.S. Cl.
CPC ............ *C07D 401/14* (2013.01); *A61P 1/00* (2018.01); *A61P 1/16* (2018.01); *A61P 3/04* (2018.01); *A61P 3/10* (2018.01); *A61P 17/06* (2018.01); *A61P 19/02* (2018.01); *A61P 37/06* (2018.01); *C07D 413/14* (2013.01)

(58) Field of Classification Search
CPC ............................. C07D 401/14; C07D 413/14
See application file for complete search history.

(56) References Cited

U.S. PATENT DOCUMENTS

| | | |
|---|---|---|
| 8,143,285 B2 | 3/2012 | Kugimiya |
| 9,556,146 B2 | 1/2017 | Bassaganya-Riera |
| 2010/0022513 A1 | 1/2010 | Forster et al. |
| 2011/0275558 A1 | 11/2011 | Bassaganya-Riera et al. |
| 2012/0157442 A1 | 6/2012 | Bui et al. |
| 2017/0158636 A1 | 6/2017 | James et al. |
| 2017/0283427 A1 | 10/2017 | Jorand-Lebrun et al. |
| 2019/0160100 A1 | 5/2019 | Bassaganya-Riera et al. |

FOREIGN PATENT DOCUMENTS

| | | |
|---|---|---|
| WO | WO 2005/000793 A1 | 1/2005 |
| WO | WO 2010/007046 A2 | 1/2010 |
| WO | WO 2011/029043 A1 | 3/2011 |
| WO | WO 2015/143376 A1 | 9/2015 |
| WO | WO 2016/008010 A1 | 1/2016 |
| WO | WO 2016/064445 A1 | 4/2016 |
| WO | WO 2017/173052 A1 | 10/2017 |
| WO | WO 2019/196803 A1 | 10/2019 |

OTHER PUBLICATIONS

Abreu, M.T., Toll-like receptor signalling in the intestinal epithelium: how bacterial recognition shapes intestinal function, Nat Rev Immunol, 2010, 10(2): p. 131-144.

Becker, A M., K .H. Dao, B.K. Han, R. Komu, S. Lakhanpal, A.B. Mobley, Q.Z. Li, Y. Lian, T. Wu, A.M. Reimold, N.J. Olsen, D.R. Karp, F.Z. Chowdhury, J.D. Farrar, A.B. Satterthwaite, C. Mohan, P.E. Lipsky, E.K. Wakeland, and L.S. Davis, SLE peripheral blood B cell, T cell and myeloid cell transcriptomes display unique profiles and each subset contributes to the interferon signature. PLoS One, 2013. 8(6): p. e67003.

Chemical Abstracts Service: Columbus, OH; Cas Registry/CAPlus Records (Jun. 18, 2020).

Chung, C.H., B.T. Kurien, P. Mehta, M. Mhatre, S. Mou, Q.N. Pye, C. Stewart, M. West, K.S. Williamson, J. Post, L. Liu, R. Wang, and K. Hensley, Identification of lanthionine synthase C-like protein-1 as a prominent glutathione binding protein expressed in the mammalian central nervous system. Biochemistry, 2007. 46(11): p. 3262-3269.

(Continued)

*Primary Examiner* — Brian E McDowell
(74) *Attorney, Agent, or Firm* — Daniel A. Blasiole; DeWitt LLP

(57) ABSTRACT

Provided are compounds of Formula (I):

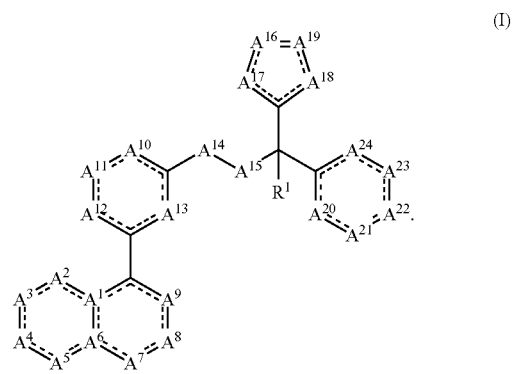

The compounds target the lanthionine synthetase C-like (LANCL) family of proteins, including LANCL2 and LANCL3. The compounds can be used to treat conditions such as inflammatory diseases, metabolic diseases, autoimmune diseases, cancers, and infectious diseases. Exemplary conditions include inflammatory conditions of the liver, such as nonalcoholic fatty liver disease, nonalcoholic steatohepatitis, and cirrhosis; inflammatory conditions of the bile duct, such as primary biliary cholangitis, primary sclerosing cholangitis; inflammatory bowel disease, such as Crohn's disease and ulcerative colitis; lupus, such as systemic lupus erythematosus, lupus nephritis, and cutaneous lupus; arthritis, such as rheumatoid arthritis; hyperglycemia, such as type 1 diabetes, type 2 diabetes, and prediabetes and associated conditions such as atherosclerosis and diabetic kidney disease; psoriasis; and multiple sclerosis.

30 Claims, 30 Drawing Sheets

(56) References Cited

OTHER PUBLICATIONS

Dattatreya et al, A Brief Review on Immune Mediated Diseases. J Clin Cell Immunol 2011, Sl1. DOI: 10.4172/2155-9899.S11-001 ISSN:2155-9899 JCCI.

Guri, A.J., R. Hontecillas, and J. Bassaganya-Riera, Abscisic acid ameliorates experimental IBD by downregulating cellular adhesion molecule expression and suppressing immune cell infiltration, Clin Nutr, 2010, 29(6): p. 824-831.

Leber, A., R. Hontecillas, N. Tubau-Juni, V. Zoccoli-Rodriguez, B. Goodpaster, and J. Bassaganya-Riera, Abscisic acid enriched fig extract promotes insulin sensitivity by decreasing systemic inflammation and activating LANCL2 in skeletal muscle. Sci Rep, 2020, 10(1): p. 10463.

Leber, A., R. Hontecillas, V. Zoccoli-Rodriguez, and J. Bassaganya-Riera, Activation of LANCL2 by BT-11 Ameliorates IBD by Supporting Regulatory T Cell Stability Through Immunometabolic Mechanisms. Inflamm Bowel Dis, 2018. 24(9): p. 1978-1991.

Myers, S.A., A. Rhoads, A.R. Cocco, R. Peckner, A.L. Haber, L.D. Schweitzer, K. Krug, D.R. Mani, K.R. Clauser, O. Rozenblatt-Rosen, N. Hacohen, A. Regev, and S.A. Carr, Streamlined Protocol for Deep Proteomic Profiling of FAC-sorted Cells and its Application to Freshly Isolated Murine Immune Cells. Mol Cell Proteomics, 2019, 18(5):p. 995-1009.

Shurin MR, Smolkin YS. Immune-mediated diseases: where do we stand? Adv Exp Med Biol. 2007;601:3-12.

Taman, H., C .G. Fenton, I.V. Hensel, E. Anderssen, J. Florholmen, and R.H. Paulssen, Transcriptomic Landscape of Treatment-Naive Ulcerative Colitis. J Crohns Colitis, 2018, 12(3): p. 327-336.

Tsuchida, T., Y.A. Lee, N. Fujiwara, M. Ybanez, B. Allen, S. Martins, M.I. Fiel, N. Goossens, H.I. Chou, Y. Hoshida, and S.L. Friedman, A simple diet- and chemical-induced murine NASH model with rapid progression of steatohepatitis, fibrosis and liver cancer. J Hepatol, 2018, 69(2): p. 385-395.

Xie, Z., B Q. Cao, T. Wang, Q. Lei, T. Kang, C.Y. Ge, W.J. Gao, and H. Hui, LanCL1 attenuates ischemia-induced oxidative stress by Sirt3-mediated preservation of mitochondrial function. Brain Res Bull, 2018, 142: p. 216-223.

Zhang, W., L. Wang, Y. Liu, J. Xu, G. Zhu, H. Cang, X. Li, M. Bartlam, K. Hensley, G. Li, Z. Rao, and X.C. Zhang, Structure of human lanthionine synthetase C-like protein 1 and its interaction with Eps8 and glutathione. Genes Dev, 2009. 23(12): p. 1387-1392.

Zocchi, E., R. Hontecillas, A. Leber, A. Einerhand, A. Carbo, S. Bruzzone, N. Tubau-Juni, N. Philipson, V. Zoccoli-Rodriguez, L. Sturla, and J. Bassaganya-Riera, Abscisic Acid: A Novel Nutraceutical for Glycemic Control. Front Nutr, 2017, 4: p. 24.

International Search Report and Written Opinion for PCT Application PCT/US2021/055874 dated Jan. 25, 2022.

Bassaganya-Riera et al. Abscisic Acid Regulates Inflammation via Ligand-binding Domain-independent Activation of Peroxisome Proliferator-activated Receptor. Journal of Biological Chemistry, vol. 286, No. 4, (2011), p. 2504-2516.

Carbo A, Gandour RD, Hontecillas R, Philipson N, Uren A, Bassaganya-Riera J. An N,N-Bis(benzimidazolylpicolinoyl)piperazine (BT-11): A Novel Lanthionine Synthetase C-Like 2-Based Therapeutic for Inflammatory Bowel Disease. *J Med Chem*. Nov. 23, 2016;59(22):10113-10126.

Renren et al. Discovery of small-molecule candidates against inflammatory bowel disease. European Journal of Medicinal Chemistry, Elsevier, Amsterdam, NL, vol. 185 (2019) XP085935544, ISSN: 0223-5234.

| ID | Structure | Affinity (kcal/mol) | |
|---|---|---|---|
| | | LANCL2 | LANCL3 |
| BT-108-1 | 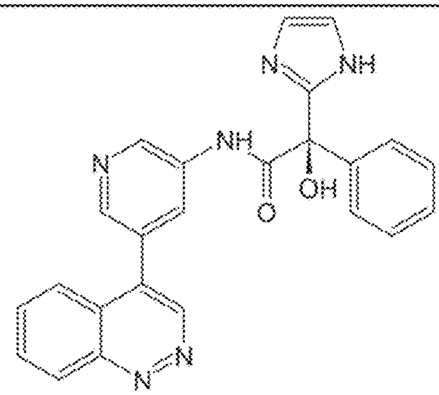 | -10.1 | -10.2 |
| BT-108-2 | 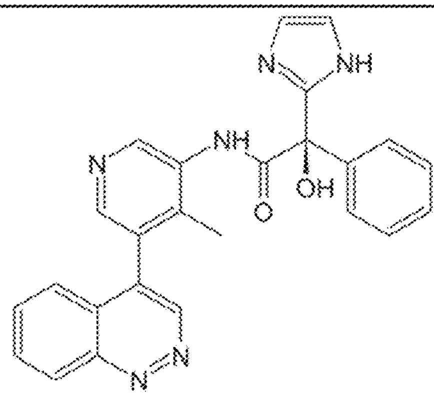 | -10.2 | -8.5 |
| BT-108-3 | 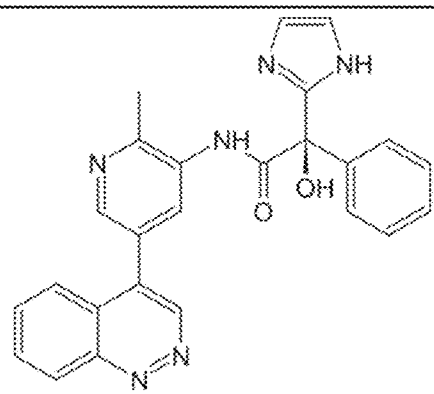 | -9.7 | -9.6 |
| BT-108-4 | 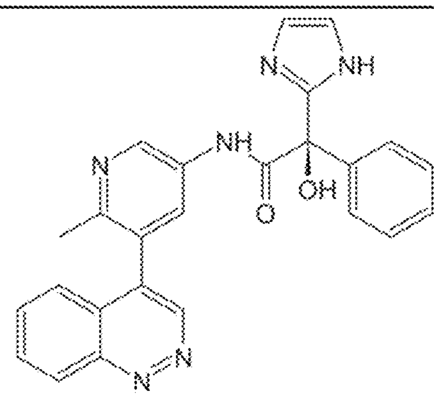 | -9.7 | -9.5 |

| ID | Structure | Affinity (kcal/mol) | |
|---|---|---|---|
| | | LANCL2 | LANCL3 |
| BT-108-5 | 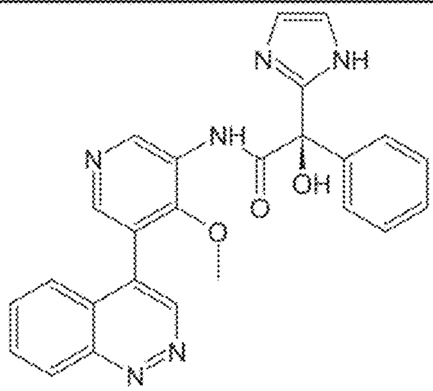 | -9.0 | -8.1 |
| BT-108-6 | 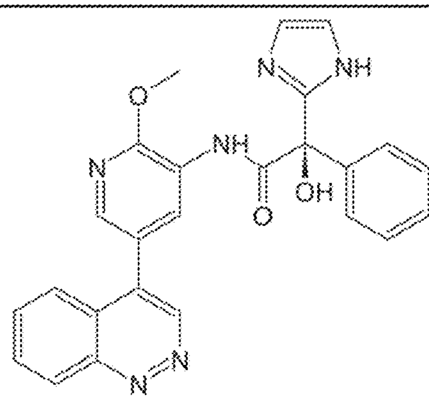 | -9.8 | -9.7 |
| BT-108-7 | 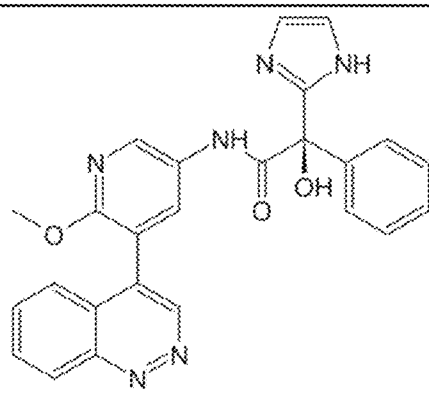 | -9.8 | -9.8 |
| BT-108-8 | 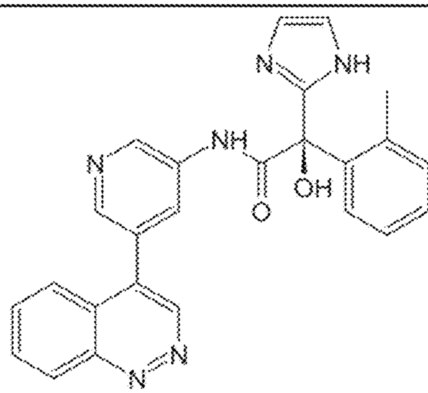 | -9.8 | -9.1 |

| ID | Structure | Affinity (kcal/mol) | |
|---|---|---|---|
| | | LANCL2 | LANCL3 |
| BT-108-9 | 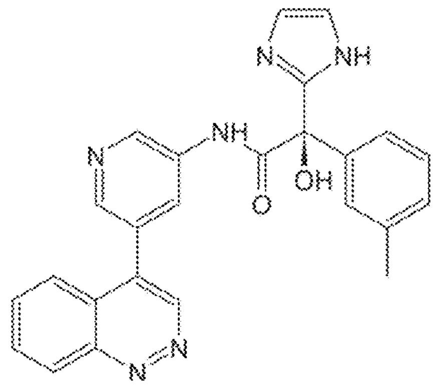 | -9.8 | -9.3 |
| BT-108-10 | 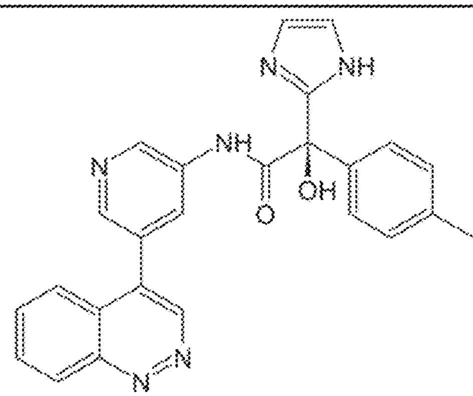 | -9.5 | -8.9 |
| BT-108-11 | 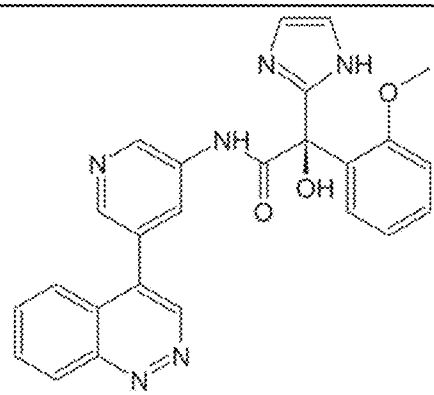 | -9.8 | -9.1 |
| BT-108-12 | 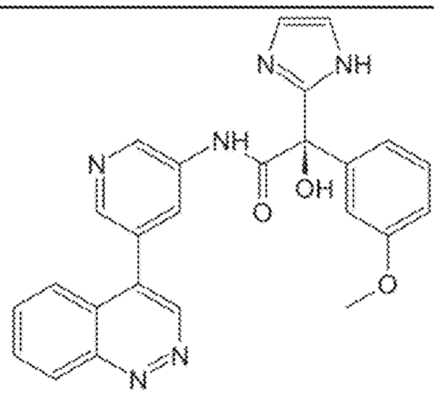 | -10.0 | -9.6 |

| ID | Structure | Affinity (kcal/mol) | |
|---|---|---|---|
| | | LANCL2 | LANCL3 |
| BT-108-13 | 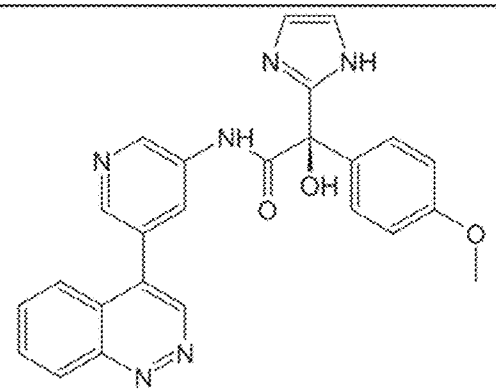 | -9.1 | -8.0 |
| BT-108-14 | 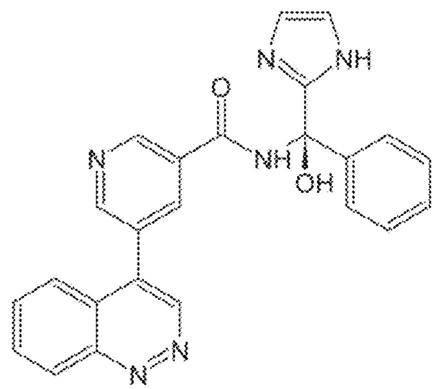 | -9.9 | -9.9 |
| BT-108-15 | 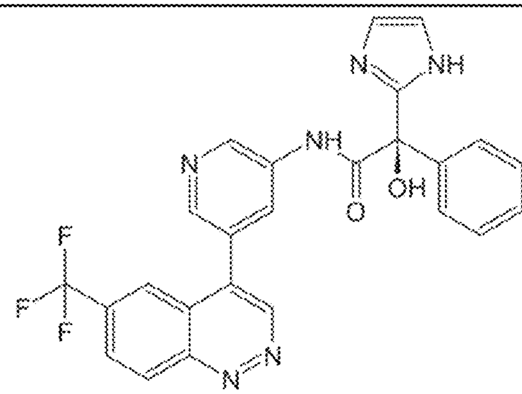 | -10.5 | -10.0 |
| BT-108-16 | 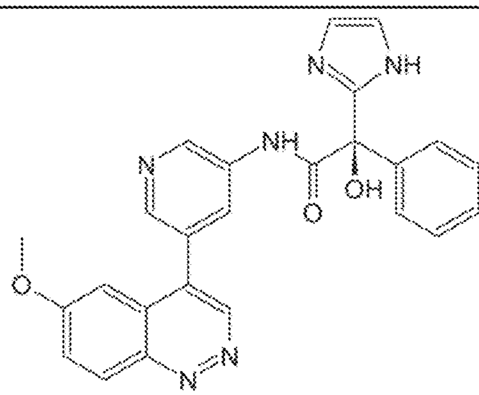 | -8.8 | -10.1 |

| ID | Structure | Affinity (kcal/mol) | |
|---|---|---|---|
| | | LANCL2 | LANCL3 |
| BT-108-17 | 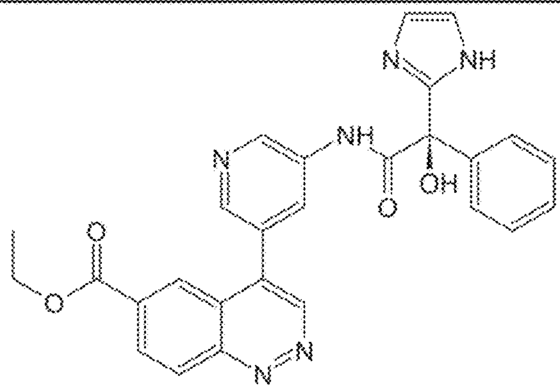 | -9.8 | -9.6 |
| BT-108-18 | 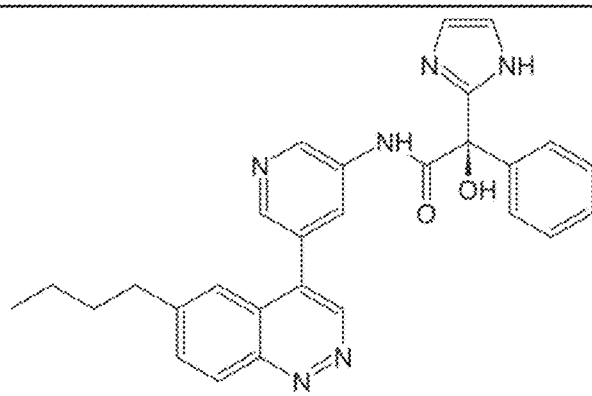 | -9.6 | -9.4 |
| BT-108-19 | 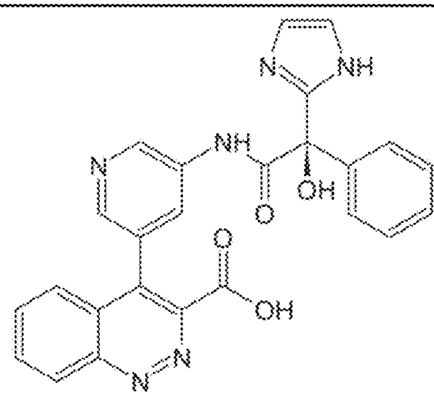 | -9.5 | -9.8 |
| BT-108-20 | 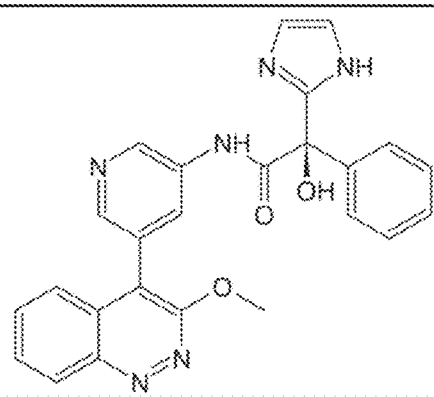 | -9.7 | -9.9 |

| ID | Structure | Affinity (kcal/mol) | |
|---|---|---|---|
| | | LANCL2 | LANCL3 |
| BT-108-21 |  | -9.1 | -9.3 |
| BT-108-22 |  | -9.1 | -8.3 |
| BT-108-23 |  | -8.2 | -8.1 |
| BT-108-24 |  | -9.3 | -8.9 |

| ID | Structure | Affinity (kcal/mol) ||
|---|---|---|---|
| | | LANCL2 | LANCL3 |
| BT-108-25 | 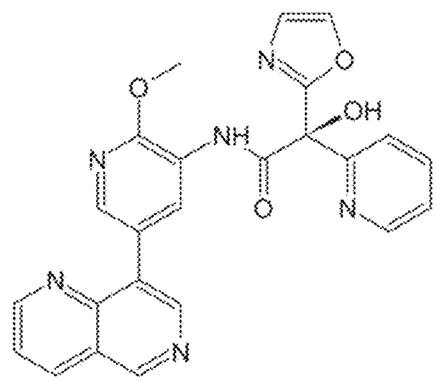 | -8.7 | -8.8 |
| BT-108-26 | 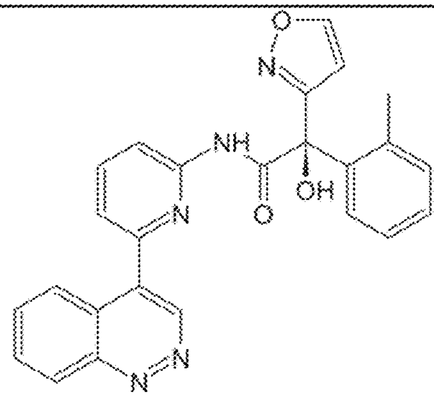 | -9.4 | -9.2 |
| BT-108-27 | 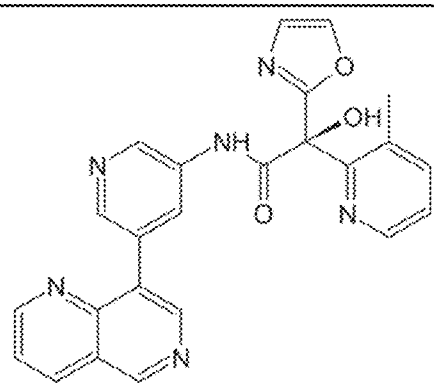 | -8.8 | -9.9 |
| BT-108-28 | 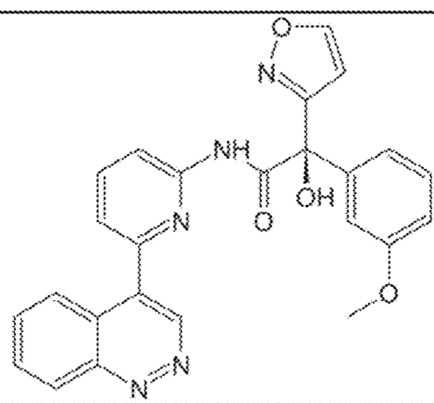 | -8.9 | -8.6 |

| ID | Structure | Affinity (kcal/mol) | |
|---|---|---|---|
| | | LANCL2 | LANCL3 |
| BT-108-29 | 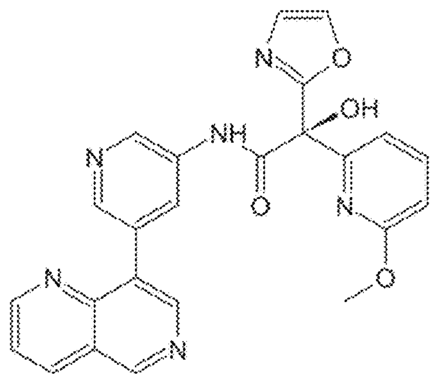 | -8.9 | -8.4 |
| BT-108-30 | 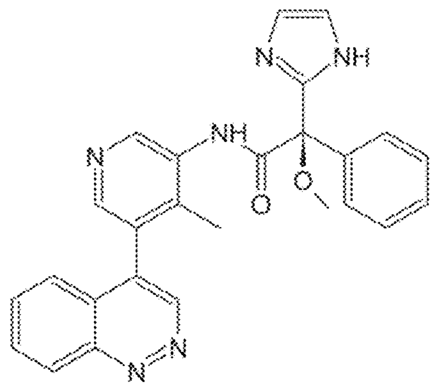 | -10.0 | -8.1 |
| BT-108-31 | 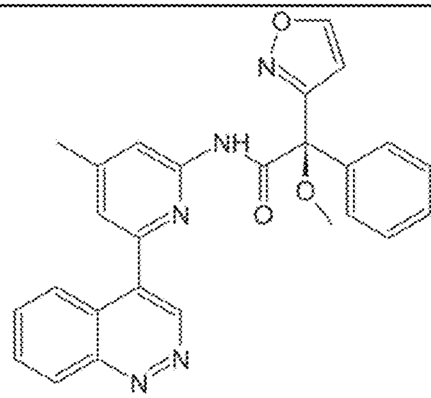 | -9.0 | -8.6 |
| BT-108-32 | 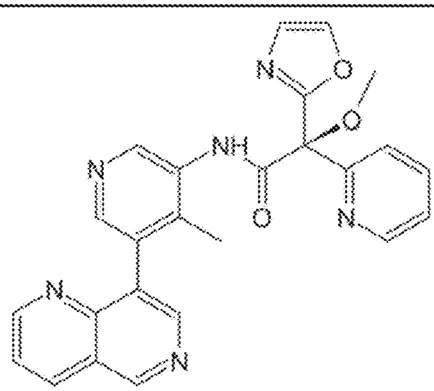 | -8.0 | -8.2 |

| ID | Structure | Affinity (kcal/mol) | |
|---|---|---|---|
| | | LANCL2 | LANCL3 |
| BT-108-33 | 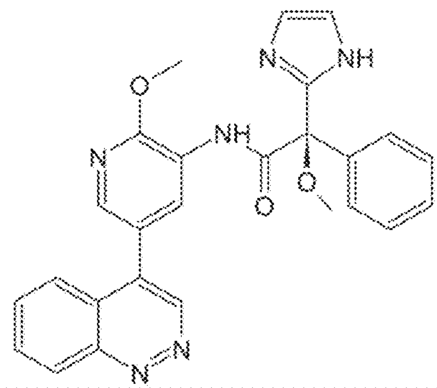 | -9.7 | -9.1 |
| BT-108-34 | 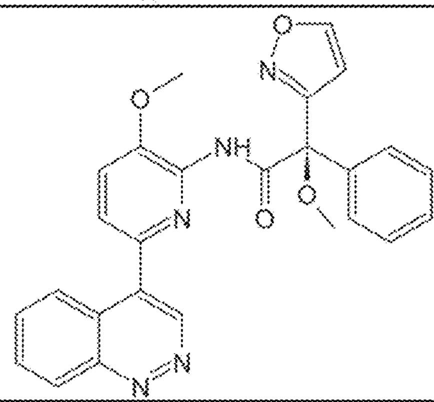 | -9.1 | -9.0 |
| BT-108-35 | 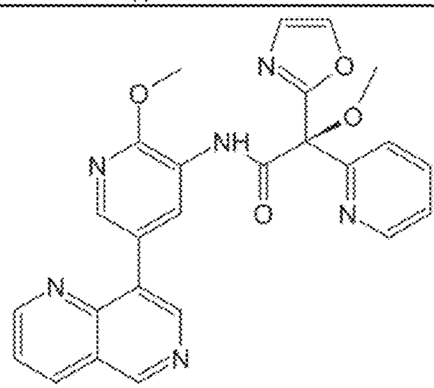 | -8.6 | -8.5 |
| BT-108-36 | 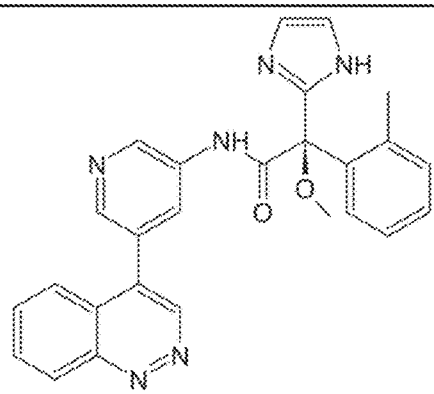 | -9.5 | -9.3 |

| ID | Structure | Affinity (kcal/mol) | |
|---|---|---|---|
| | | LANCL2 | LANCL3 |
| BT-108-37 | 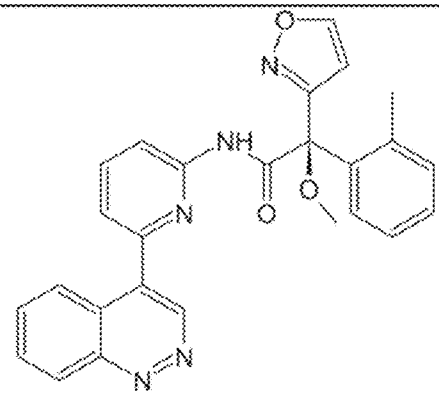 | -9.2 | -9.4 |
| BT-108-38 | 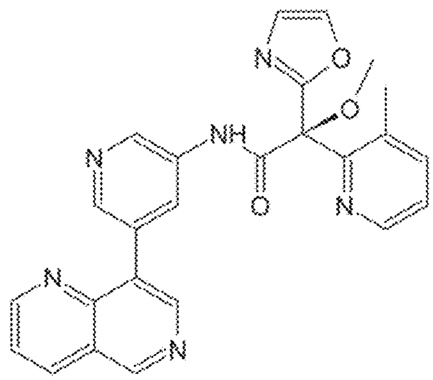 | -8.5 | -9.8 |
| BT-108-39 | 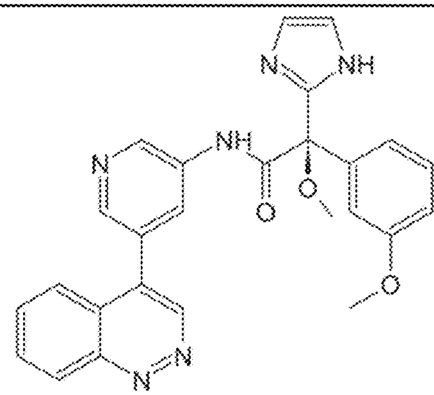 | -9.8 | -9.4 |
| BT-108-40 | 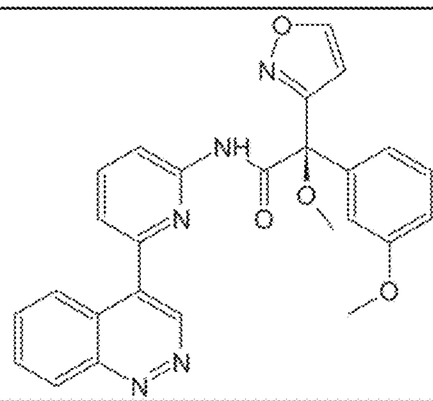 | -8.9 | -9.3 |

FIG. 1J

| ID | Structure | Affinity (kcal/mol) | |
|---|---|---|---|
| | | LANCL2 | LANCL3 |
| BT-108-41 | 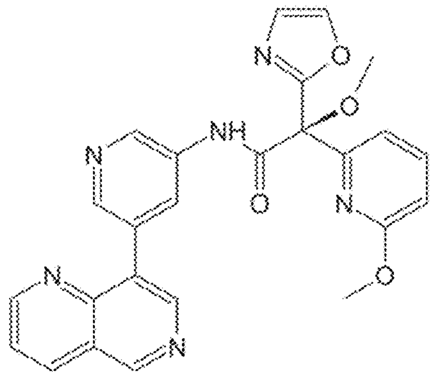 | -9.1 | -8.1 |
| BT-108-42 | 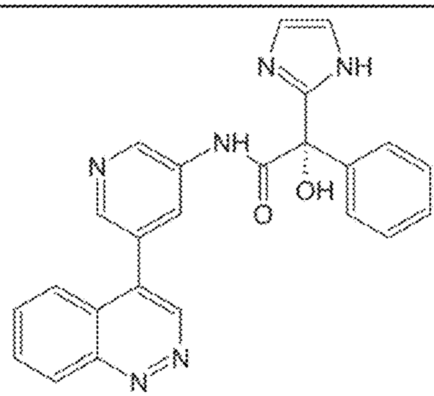 | -10.0 | -10.2 |
| BT-108-43 | 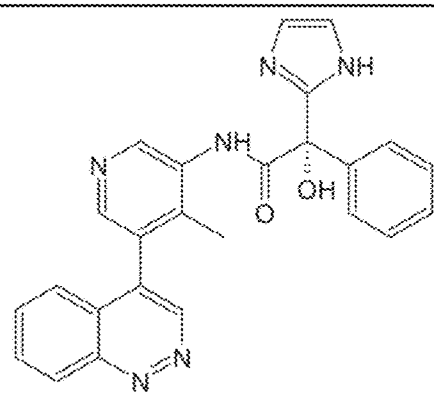 | -9.9 | -8.6 |
| BT-108-44 | 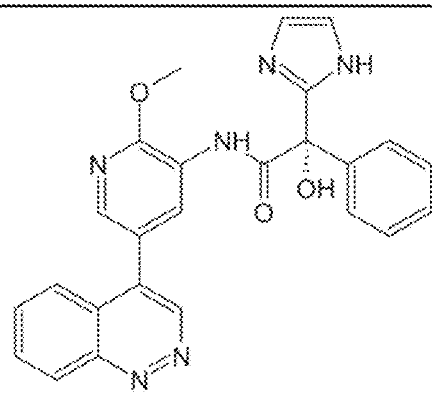 | -9.8 | -9.9 |

| ID | Structure | Affinity (kcal/mol) | |
|---|---|---|---|
| | | LANCL2 | LANCL3 |
| BT-108-45 | 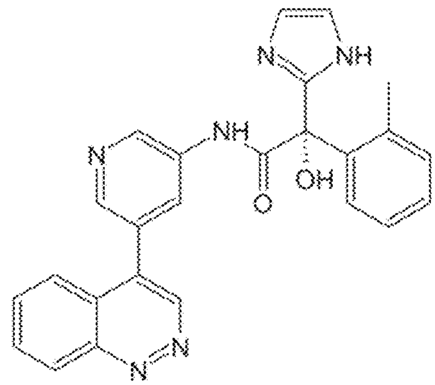 | -9.9 | -9.0 |
| BT-108-46 | 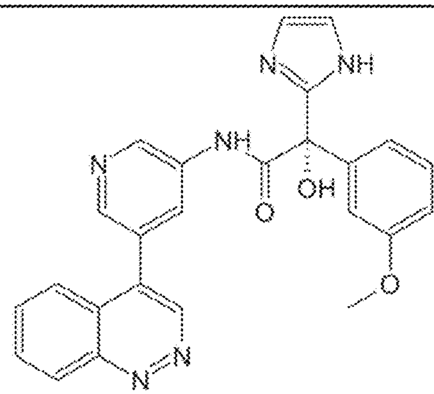 | -9.7 | -9.3 |
| BT-108-47 | 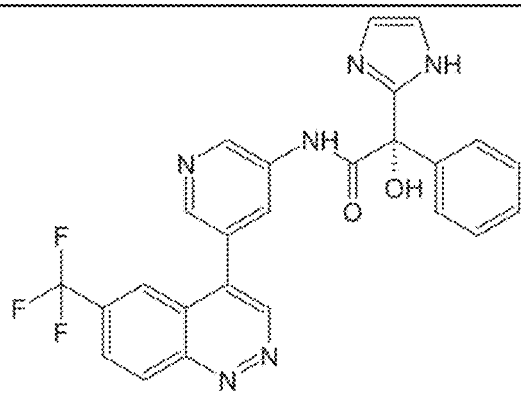 | -10.1 | -10.0 |
| BT-108-48 | 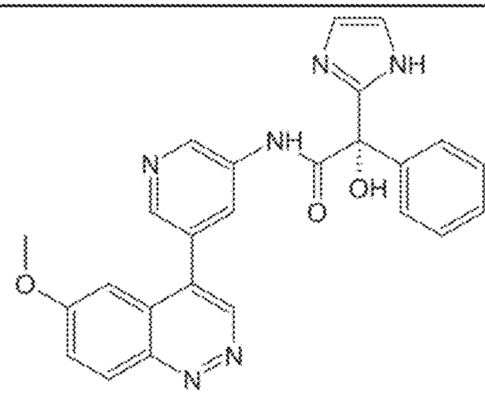 | -8.3 | -9.9 |

| ID | Structure | Affinity (kcal/mol) | |
|---|---|---|---|
| | | LANCL2 | LANCL3 |
| BT-108-49 | 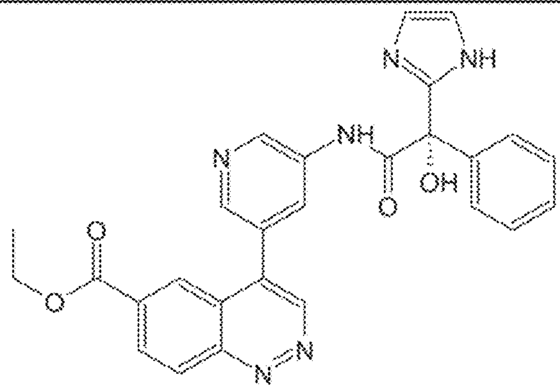 | -9.8 | -9.6 |
| BT-108-50 | 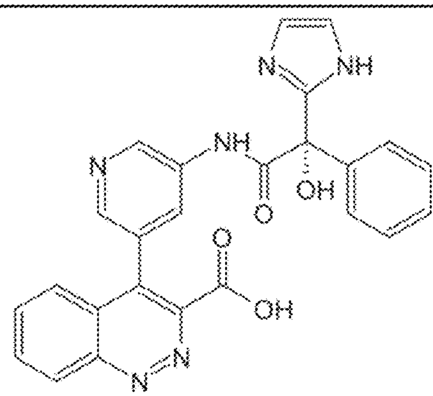 | -9.6 | -9.6 |
| BT-108-51 | 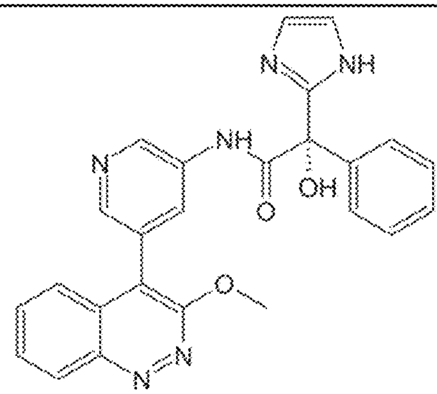 | -9.7 | -9.8 |
| BT-108-52 | 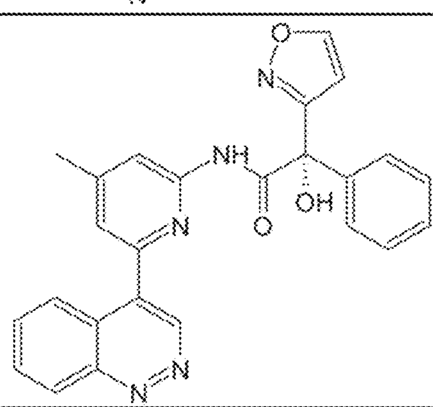 | -9.0 | -8.1 |

FIG. 1M

| ID | Structure | Affinity (kcal/mol) | |
|---|---|---|---|
| | | LANCL2 | LANCL3 |
| BT-108-53 | 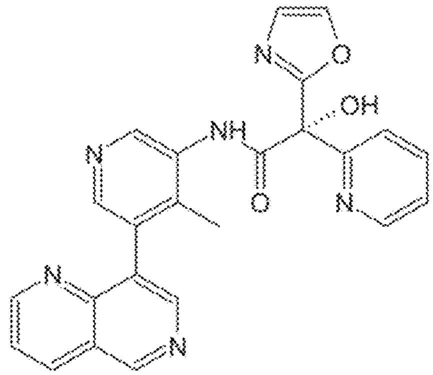 | -8.2 | -8.2 |
| BT-108-54 | 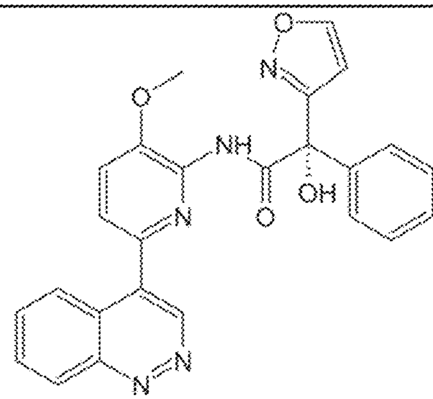 | -9.1 | -8.8 |
| BT-108-55 | 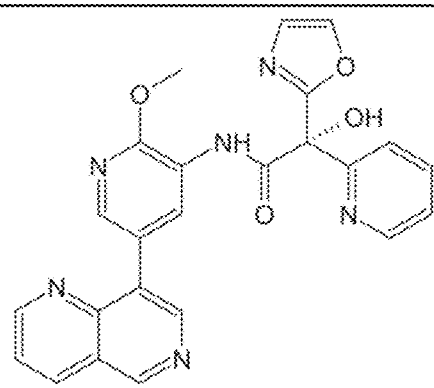 | -8.8 | -8.6 |
| BT-108-56 | 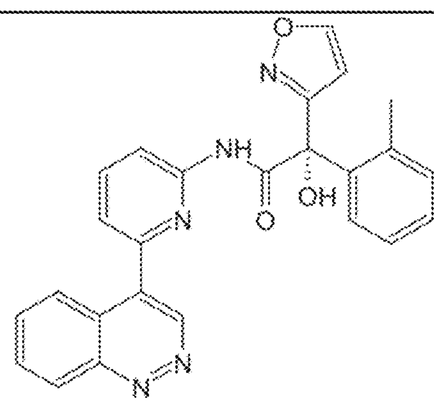 | -9.4 | -9.2 |

| ID | Structure | Affinity (kcal/mol) | |
|---|---|---|---|
| | | LANCL2 | LANCL3 |
| BT-108-57 | 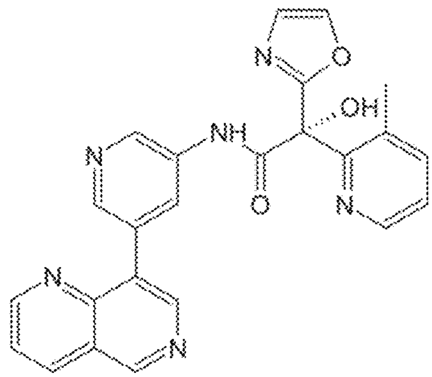 | -8.9 | -9.7 |
| BT-108-58 | 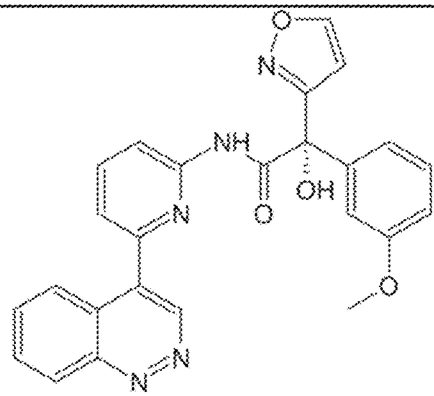 | -8.9 | -8.7 |
| BT-108-59 | 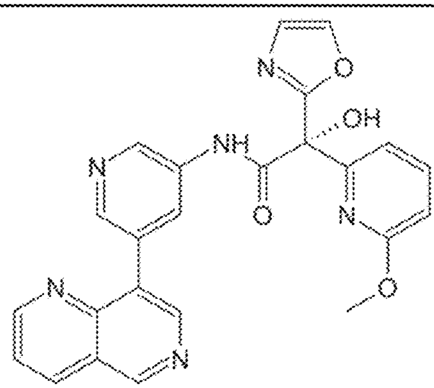 | -8.6 | -8.3 |
| BT-108-60 | 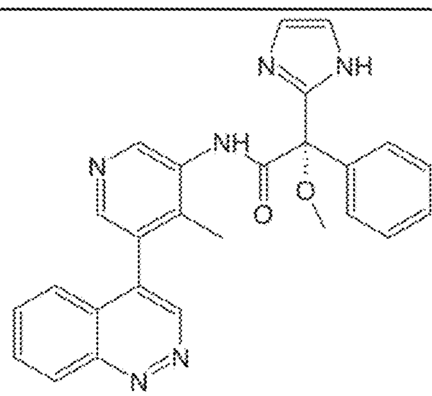 | -9.9 | -8.1 |

| ID | Structure | Affinity (kcal/mol) | |
|---|---|---|---|
| | | LANCL2 | LANCL3 |
| BT-108-61 | 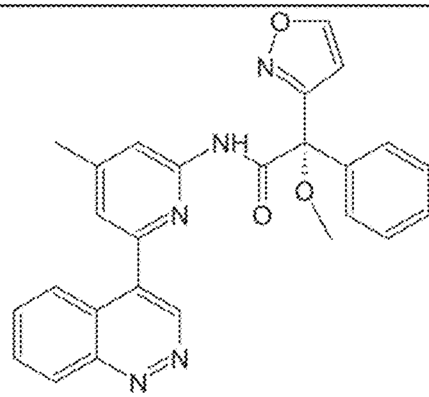 | -9.2 | -8.5 |
| BT-108-62 | 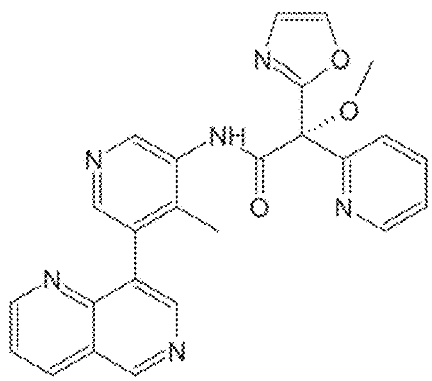 | -8.1 | -8.4 |
| BT-108-63 | 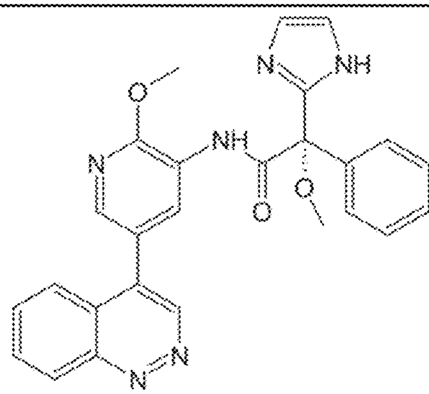 | -9.8 | -9.0 |
| BT-108-64 | 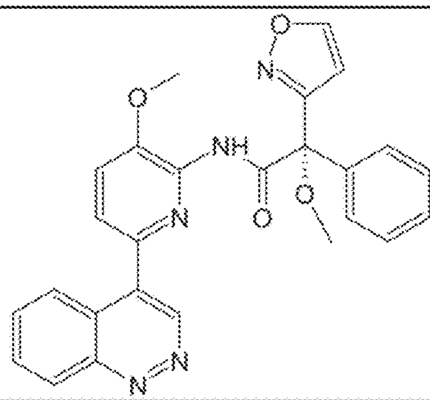 | -9.3 | -9.0 |

| ID | Structure | Affinity (kcal/mol) | |
|---|---|---|---|
| | | LANCL2 | LANCL3 |
| BT-108-65 | 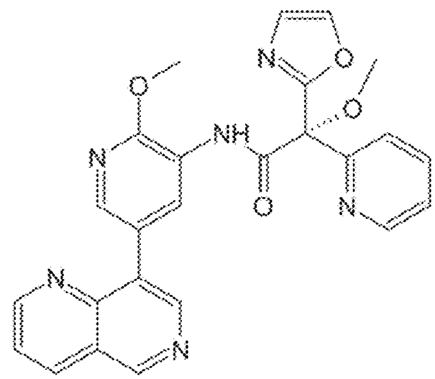 | -8.7 | -8.6 |
| BT-108-66 | 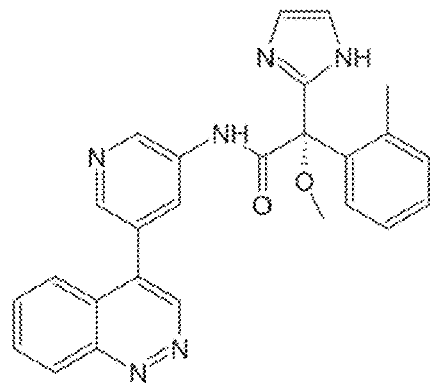 | -9.6 | -9.2 |
| BT-108-67 | 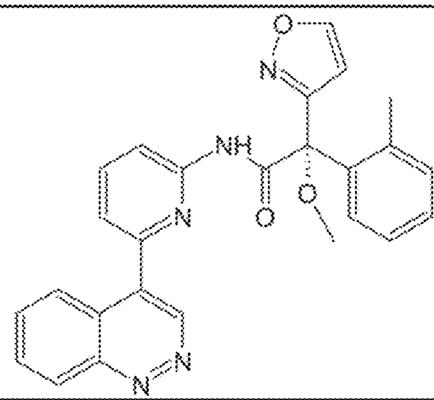 | -9.2 | -9.2 |
| BT-108-68 | 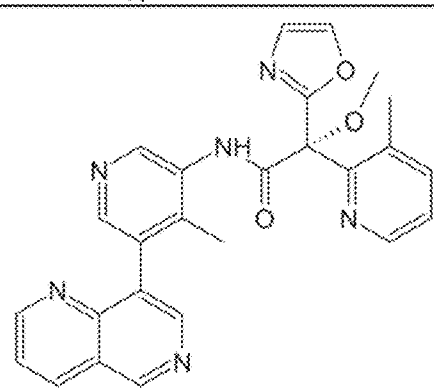 | -8.7 | -9.4 |

| ID | Structure | Affinity (kcal/mol) | |
|---|---|---|---|
| | | LANCL2 | LANCL3 |
| BT-108-69 | 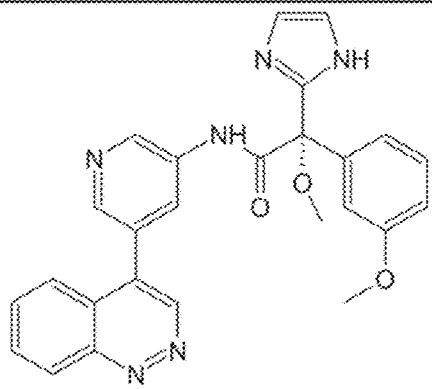 | -9.9 | -9.1 |
| BT-108-70 | 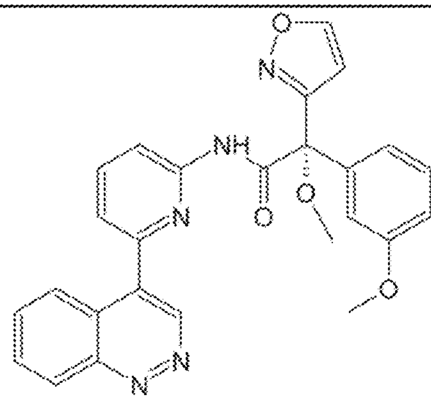 | -9.0 | -9.2 |

LANCL LIGANDS

FIELD OF THE INVENTION

The present invention relates to ligands of lanthionine synthetase C-like (LANCL) proteins, including LANCL2 and LANCL3, and methods of treating diseases and disorders with same.

BACKGROUND

The lanthionine synthetase C-like (LANCL) family of proteins is comprised of three signaling proteins (LANCL1, LANCL2, and LANCL3) that are at the interface of immunity and metabolism. While LANCL1 is localized to the central nervous system, LANCL2 and LANCL3 are more widely expressed throughout the body. LANCL3 is most highly expressed in immune cells, endocrine tissues, and squamous epithelial cells, as well as hepatocytes and fibroblasts. LANCL1 is a glutathione transferase that functions in the prevention of oxidative stress in part through regulation of SIRT proteins [1, 2]. LANCL2 has been characterized as the mammalian receptor for abscisic acid for the promotion of glycemic control and is differentially expressed in regulatory CD4+ T cells with its activity associated with increased stability and suppressive function of these cells [3-5]. Unlike LANCL1 and LANCL2, which are expressed on the plasma membrane, LANCL3 is associated with the mitochondria. As such, the loss of LANCL3 is associated with impaired mitochondrial metabolism as well as increased inflammatory responses in immune cells.

There are clear clinical needs for safe, efficacious treatments for diseases in which LANCL2 and LANCL3 are implicated. LANCL3 has been identified to be downregulated in unbiased transcriptomic studies of ulcerative colitis [6] and systemic lupus erythematosus [7], among others. Due to low efficacy and poor safety, current autoimmune treatments require frequent monitoring, shifting treatment paradigms, and complex delivery methods. Thus, new treatments capable of being dosed orally for long-term management of disease are needed. In infectious diseases, high mutation rates in various microbes necessitate the development of novel non-antimicrobial treatments that spare the use of antibacterials, antifungals, and antivirals. Further, new strains and epidemic infections create a lag period between the emergence of a pathogen and the availability of microbe-specific interventions, creating a need for novel host-targeted therapeutics. Given the epidemic of infectious and autoimmune diseases as a whole, the LANCL pathways have the potential to significantly impact millions of patients.

Natural compounds have been identified to bind to the LANCL family of proteins. In particular, abscisic acid ("ABA") is a natural compound found to bind to LANCL2 [5]. ABA has been shown to elicit anti-inflammatory effects and improvement of glycemic control dependent on signaling through LANCL2 [8, 9]. Binding domains for glutathione have been identified in LANCL1 [1]. Further, LANCL1 has been demonstrated to have affinity for other signaling proteins in vitro [10]. Previously, synthetic compounds, such as BT-11, have been developed to target LANCL2 (U.S. Pat. No. 9,556,146).

The present invention provides compounds that have been developed by novel medicinal chemistry approaches, and screened using in silico, in vitro, and in vivo techniques, to maximize their ability to bind to the LANCL family of proteins and thus to induce a beneficial response in various disease conditions.

SUMMARY OF THE INVENTION

The invention provides compounds of Formula (I):

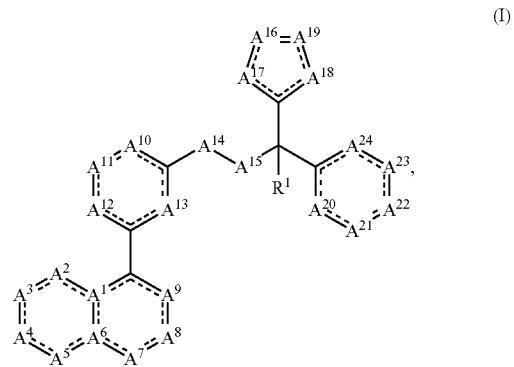

or a salt or ester thereof, wherein:
$A^1$ and $A^6$ are each C;
$A^2$, $A^3$, $A^4$, $A^5$, $A^7$, $A^8$, $A^9$, $A^{10}$, $A^{11}$, $A^{12}$, $A^{13}$, $A^{20}$, $A^{21}$, $A^{22}$, $A^{23}$, and $A^{24}$ are each independently N or $C(R^2)$;
$A^{14}$ and $A^{15}$ are each C(O) or $N(R^L)$, with the proviso that $A^{14}$ and $A^{15}$ are not both C(O) and are not both $N(R^L)$;
$A^{16}$, $A^{17}$, $A^{18}$, and $A^{19}$ are each independently selected from O, $N(R^2)$, S, N, and $C(R^2)$, with the proviso that one and only one of $A^{16}$, $A^{17}$, $A^{18}$, and $A^{19}$ is O, $N(R^2)$, or S;
- - - represents delocalized pi bonds;
$R^1$, $R^2$, and $R^L$ in each instance are independently hydrogen, halogen, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, thiol, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkyl sulfinyl, optionally substituted cycloalkyl sulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

In some versions, $A^8$ is N. In some versions, at least one of $A^{11}$ and $A^{13}$ is N. In some versions, $A^{17}$ is N, $A^{18}$ is $N(R^2)$, or $A^{17}$ is N and $A^{18}$ is $N(R^2)$. In some versions, $R^1$ is hydroxyl or optionally substituted alkyloxy. In some versions:

each optionally substituted alkyl, optionally substituted alkyloxy, optionally substituted alkylthio, optionally substituted alkylsulfinyl, optionally substituted alkylsulfonyl, optionally substituted alkylsulfonyloxy, and optionally substituted alkyloxycarbonyl, when substituted, is independently substituted with one to three substituent(s) selected from the group consisting of cycloalkyl, alkylene optionally containing one or two heteroatom(s), hydroxyl, oxo, alkyloxy optionally substituted with a substituent group A at one to three position(s), thiol, alkylthio, halogen, nitro, cyano, carboxyl, alkyloxycarbonyl, optionally substituted amino, optionally substituted carbamoyl, acyl, aryl optionally substituted with a substituent group B at one to three position(s), heteroaryl optionally substituted with a substituent group C at one to three position(s), an optionally substituted non-aromatic heterocyclic ring group optionally substituted with a substituent group C at one to three position(s), aryloxy optionally substituted with a substituent group B at one to three position(s), and alkylsulfonyl;

each optionally substituted alkenyl, optionally substituted alkynyl, optionally substituted alkenyloxy, optionally substituted alkynyloxy, optionally substituted alkenylthio, optionally substituted alkynylthio, optionally substituted alkenyloxycarbonyl, optionally substituted alkynyloxycarbonyl, optionally substituted cycloalkyl, optionally substituted cycloalkenyl, optionally substituted cycloalkyloxy, optionally substituted cycloalkenyloxy, optionally substituted cycloalkylthio, optionally substituted cycloalkenylthio, optionally substituted cycloalkyl sulfinyl, optionally substituted cycloalkenyl sulfinyl, optionally substituted cycloalkyl sulfonyl, optionally substituted cycloalkenyl sulfonyl, optionally substituted cycloalkylsulfonyloxy, optionally substituted cycloalkenylsulfonyloxy, and optionally substituted alkylene optionally containing one or two heteroatom(s), when substituted, is independently substituted with one or more substituent(s) selected from the group consisting of alkyl optionally substituted with a substituent group D at one to three position(s), cycloalkyl, hydroxyl, oxo, alkyloxy optionally substituted with a substituent group A at one to three position(s), thiol, alkylthio, halogen, nitro, cyano, carboxyl, alkyloxycarbonyl, optionally substituted amino, optionally substituted carbamoyl, acyl, acyloxy, aryl optionally substituted with a substituent group B at one to three position(s), heteroaryl optionally substituted with a substituent group C at one to three position(s), non-aromatic heterocyclic group optionally substituted with a substituent group C at one to three position(s), aryloxy optionally substituted with a substituent group C at one to three position(s), and alkyl sulfonyl;

each optionally substituted aryl, optionally substituted aryloxy, optionally substituted aryloxycarbonyl, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, and optionally substituted non-aromatic heterocyclic group, when substituted, are each independently substituted with one or more substituent(s) selected from the group consisting of alkyl optionally substituted with a substituent group D at one to three position(s), oxo, cycloalkyl, alkenyl, alkynyl, hydroxyl, alkyloxy optionally substituted with a substituent group A at one to three position(s), aryloxy optionally substituted with a substituent group B at one to three position(s), thiol, alkylthio, halogen, nitro, cyano, carboxyl, alkyloxycarbonyl, acyl, alkylsulfonyl, optionally substituted amino, optionally substituted carbamoyl, aryl optionally substituted with a substituent group B at one to three position(s), heteroaryl optionally substituted with a substituent group C at one to three position(s), and non-aromatic heterocyclic group optionally substituted with a substituent group C at one to three position(s);

each optionally substituted amino, optionally substituted carbamoyl, and optionally substituted sulfamoyl, when substituted, is independently substituted with one or two substituent(s) selected from the group consisting of alkyl, alkenyl, alkynyl, cycloalkyl, cycloalkynyl, aryl, heteroaryl, acyl, alkyloxycarbonyl, alkenyloxycarbonyl, alkynyloxycarbonyl, alkyl sulfonyl, alkenyl sulfonyl, alkynylsulfonyl, aryl sulfonyl, and heteroarylsulfonyl;

each substituent group A is independently selected from the group consisting of halogen and phenyl optionally substituted with one to three substituent(s) selected from substituent group B;

each substituent group B is independently selected from the group consisting of halogen, alkyl, alkyloxy, cyano, and nitro;

each substituent group C is independently selected from the group consisting of halogen and alkyl; and each substituent group D is independently selected from the group consisting of halogen and alkyloxy.

Additional embodiments are described elsewhere herein.

The compounds provided herein are ligands of LANCL3 and LANCL2.

Exemplary compounds include BT-108-1, BT-108-2, BT-108-3, BT-108-4, BT-108-5, BT-108-6, BT-108-7, BT-108-8, BT-108-9, BT-108-10, BT-108-11, BT-108-12, BT-108-13, BT-108-14, BT-108-15, BT-108-16, BT-108-17, BT-108-18, BT-108-19, BT-108-20, BT-108-21, BT-108-22, BT-108-23, BT-108-24, BT-108-25, BT-108-26, BT-108-27, BT-108-28, BT-108-29, BT-108-30, BT-108-31, BT-108-32, BT-108-33, BT-108-34, BT-108-35, BT-108-36, BT-108-37, BT-108-38, BT-108-39, BT-108-40, BT-108-41, BT-108-42, BT-108-43, BT-108-44, BT-108-45, BT-108-46, BT-108-47, BT-108-48, BT-108-49, BT-108-50, BT-108-51, BT-108-52, BT-108-53, BT-108-54, BT-108-55, BT-108-56, BT-108-57, BT-108-58, BT-108-59, BT-108-60, BT-108-61, BT-108-62, BT-108-63, BT-108-64, BT-108-65, BT-108-66, BT-108-67, BT-108-68, BT-108-69, and BT-108-70 as shown in FIGS. 1A-1R and 2A-2F, as well as salts of any of the foregoing.

The invention also provides methods of treating a condition in an animal with a compound as described herein. The methods comprise administering an effective amount of the compound to the animal. The condition may comprise at least one of an inflammatory disease, a metabolic disease, an autoimmune disease, cancer, and an infectious disease. In some versions, the condition comprises inflammatory conditions of the liver, such as nonalcoholic fatty liver disease, nonalcoholic steatohepatitis, and cirrhosis. In some versions, the condition comprises inflammatory conditions of the bile duct, such as primary biliary cholangitis, primary sclerosing cholangitis. In some versions, the condition comprises inflammatory bowel disease, such as Crohn's disease and ulcerative colitis. In some versions, the condition comprises lupus, such as systemic lupus erythematosus, lupus nephritis, and cutaneous lupus. In some versions, the condition comprises arthritis, such as rheumatoid arthritis. In some versions, the condition comprises hyperglycemia, such as type 1 diabetes, type 2 diabetes, and prediabetes, and, optionally, resulting complications such as atherosclerosis and diabetic kidney disease. In some versions, the condition comprises psoriasis. In some versions, the condition comprises multiple sclerosis.

The objects and advantages of the invention will appear more fully from the following detailed description of the preferred embodiment of the invention made in conjunction with the accompanying drawings.

DETAILED DESCRIPTION OF THE INVENTION

Figure 1A:
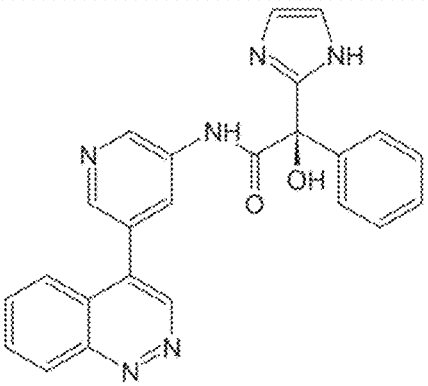
FIGS. 1A-1R. Computational prediction of binding of selected compounds to LANCL2 and LANCL3 in kcal/mol.
Figure 1A:
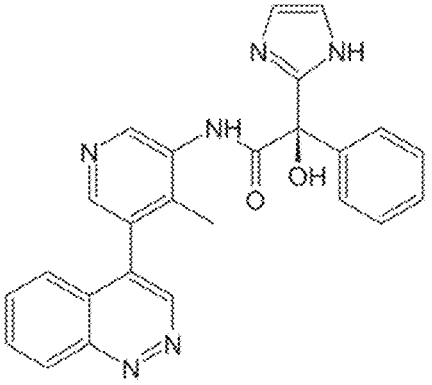
Figure 1A:
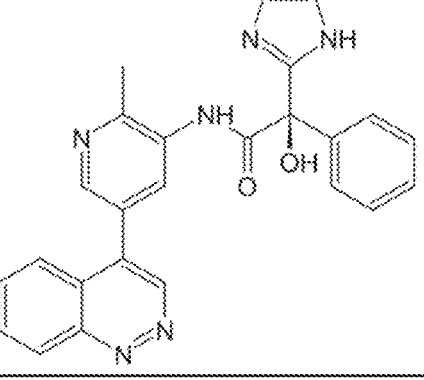
Figure 1A:
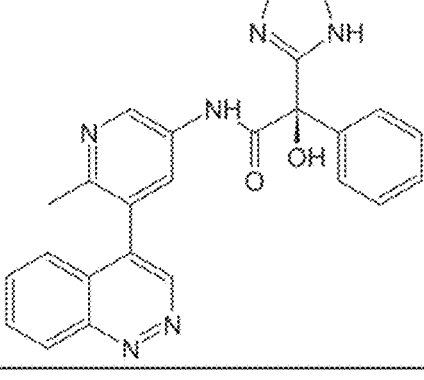
Figure 1B:
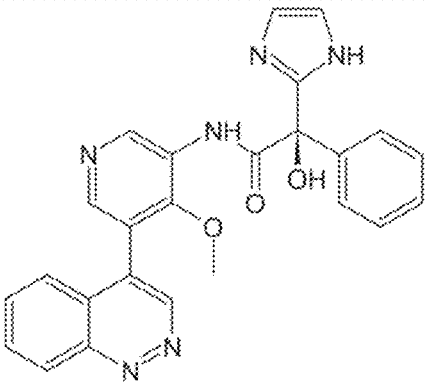
Figure 1B:
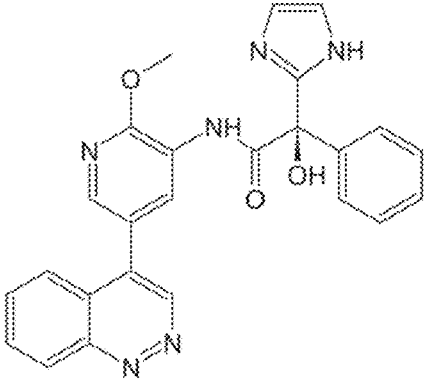
Figure 1B:
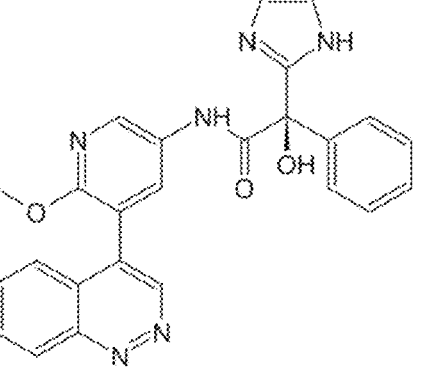
Figure 1B:
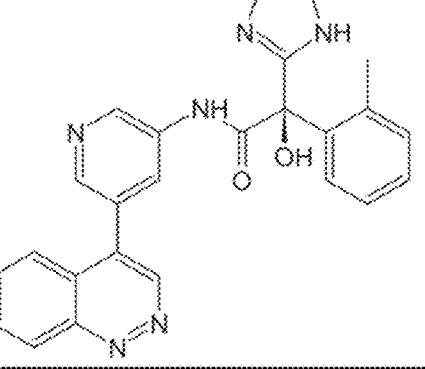
Figure 1C:
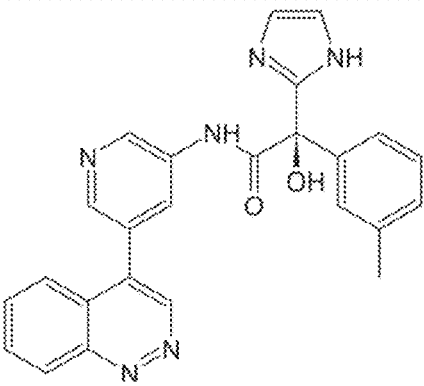
Figure 1C:
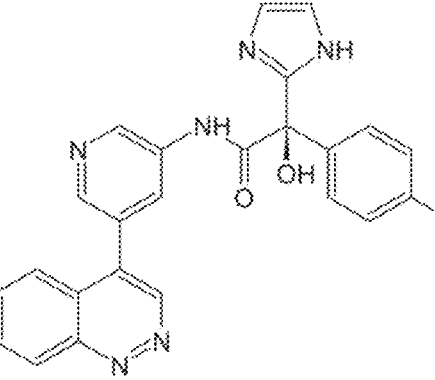
Figure 1C:
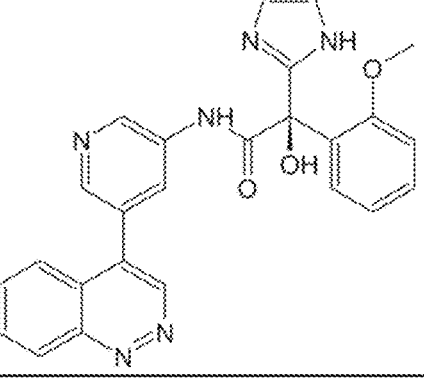
Figure 1C:
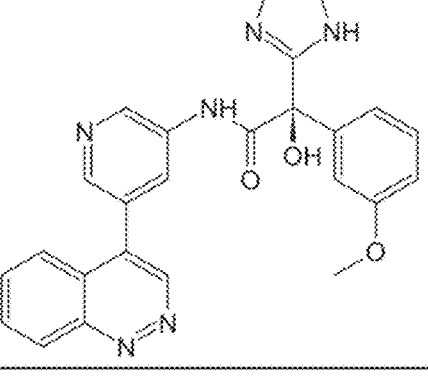
Figure 1D:
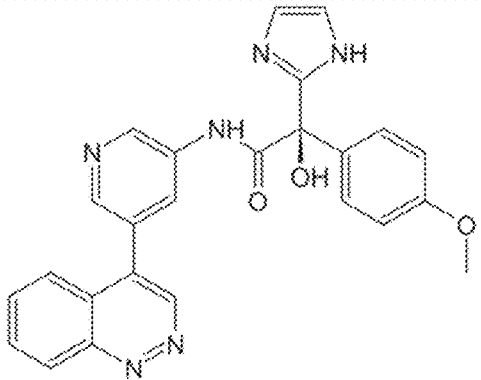
Figure 1D:
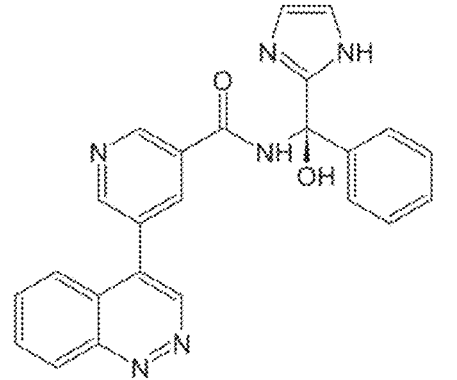
Figure 1D:
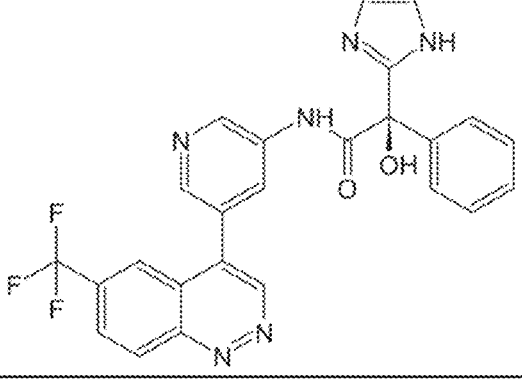
Figure 1D:
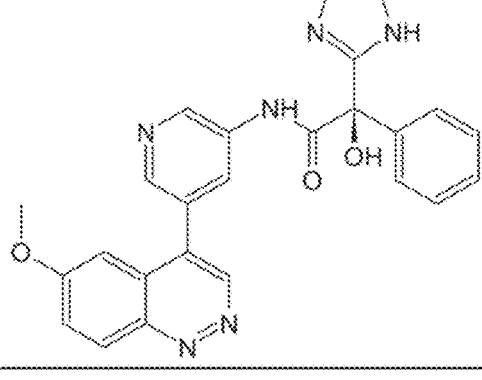
Figure 1E:
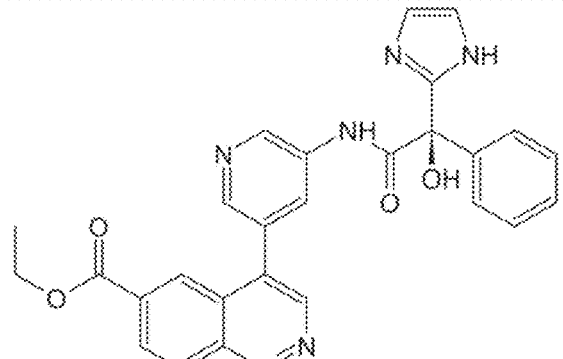
Figure 1E:
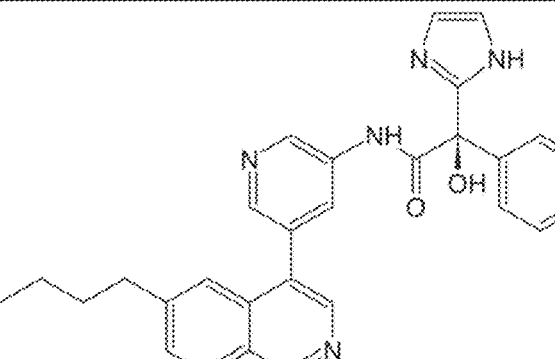
Figure 1E:
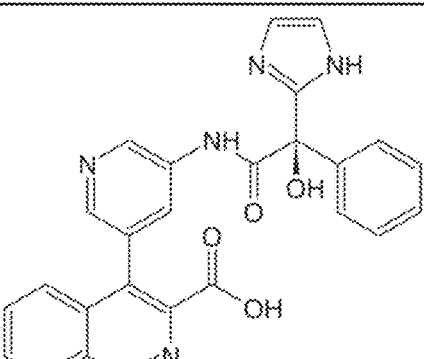
Figure 1E:
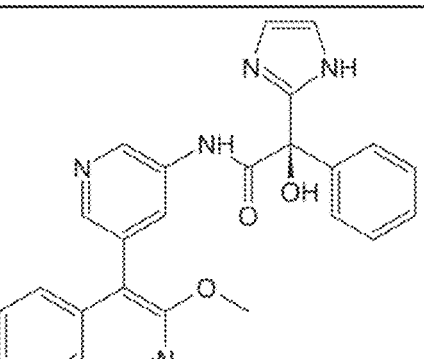
Figure 1F:
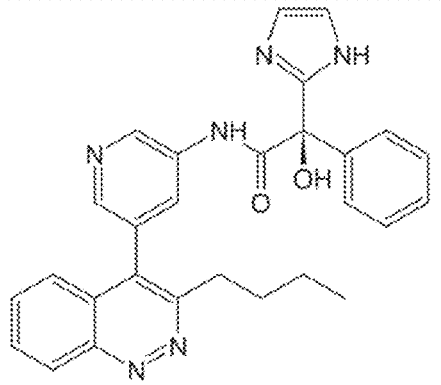
Figure 1F:
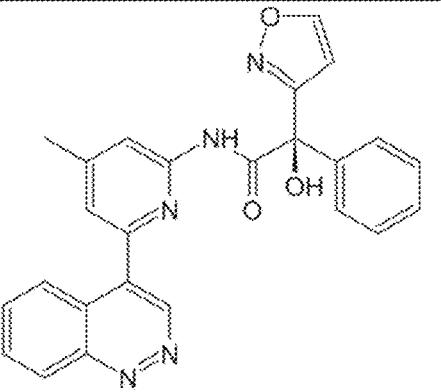
Figure 1F:
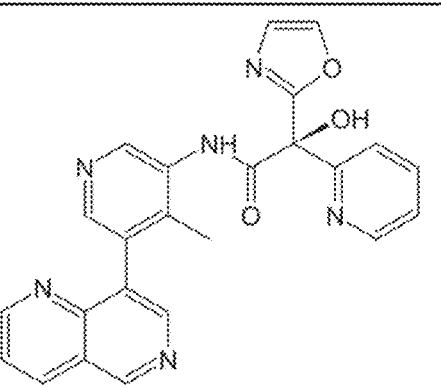
Figure 1F:
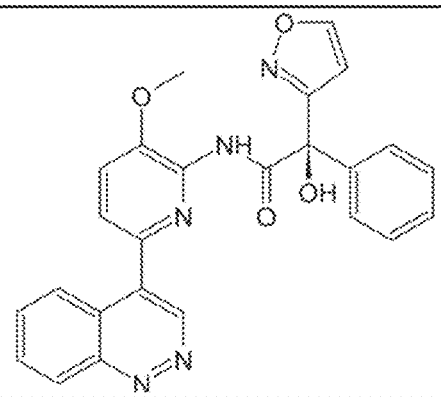
Figure 1G:
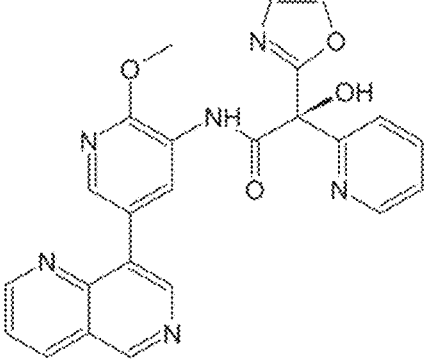
Figure 1G:
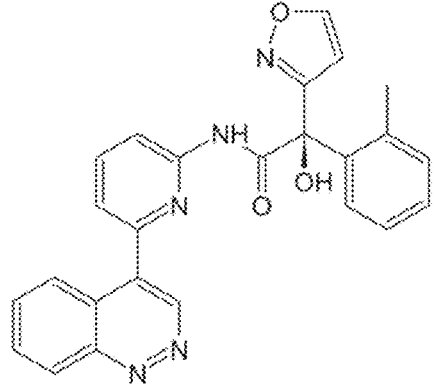
Figure 1G:
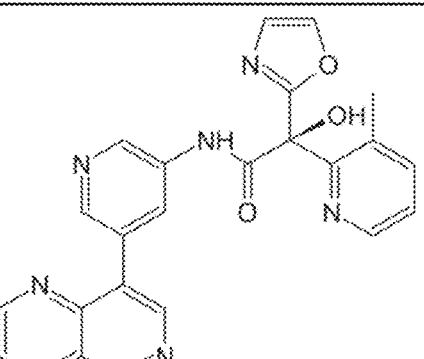
Figure 1G:
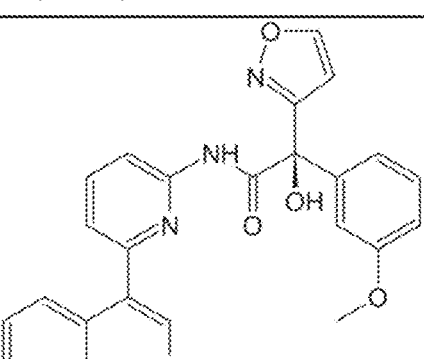
Figure 1H:
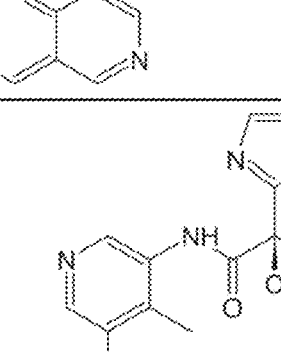
Figure 1H:
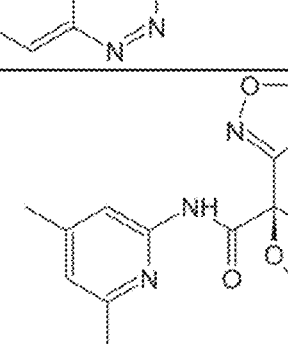
Figure 1H:
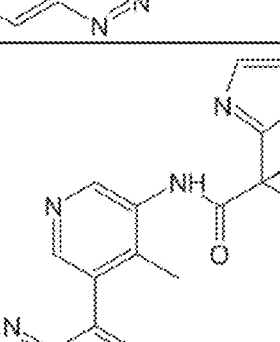
Figure 1H:
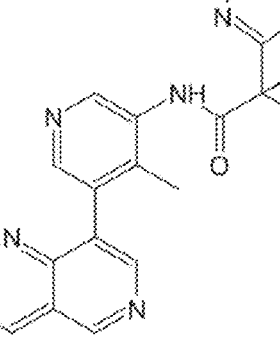
Figure 1I:
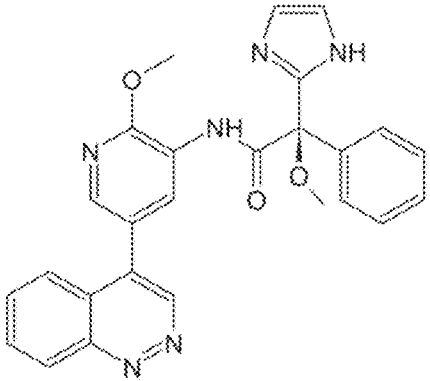
Figure 1I:
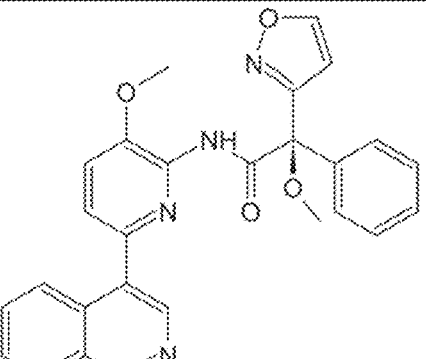
Figure 1I:
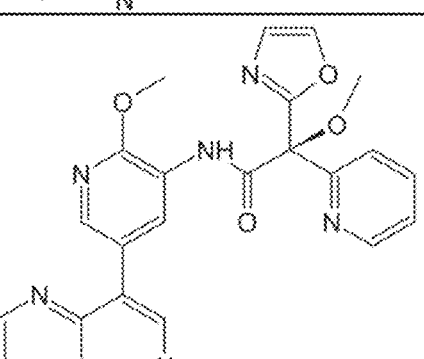
Figure 1I:
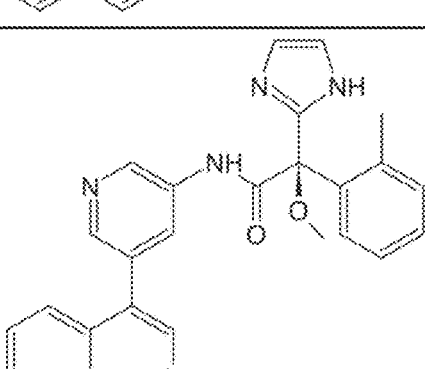
Figure 1K:
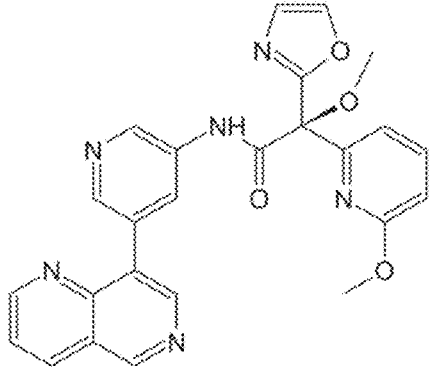
Figure 1K:
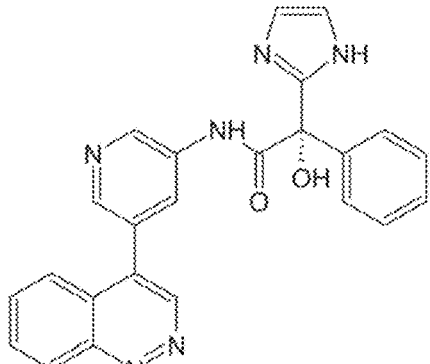
Figure 1K:
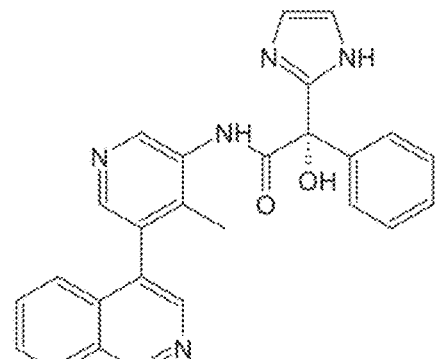
Figure 1K:
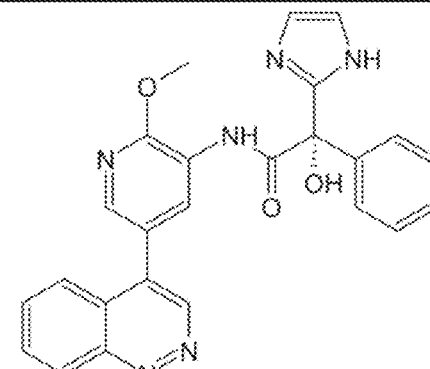
Figure 1L:
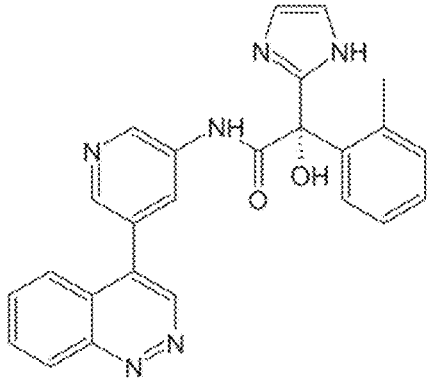
Figure 1L:
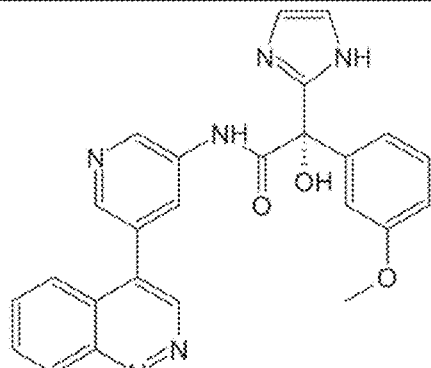
Figure 1L:
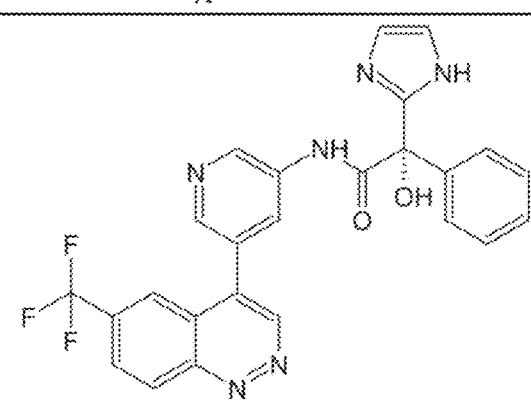
Figure 1L:
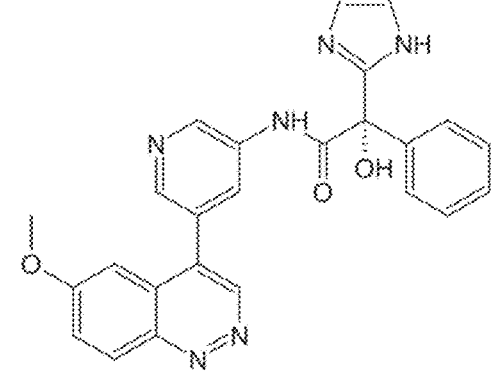
Figure 1N:
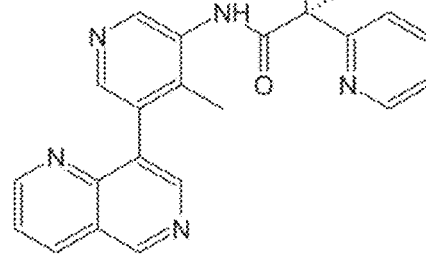
Figure 1N:
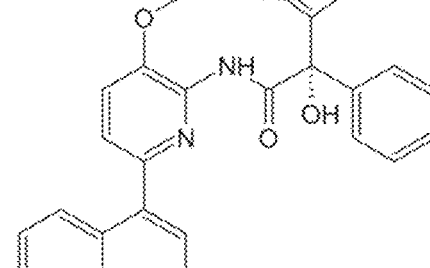
Figure 1N:
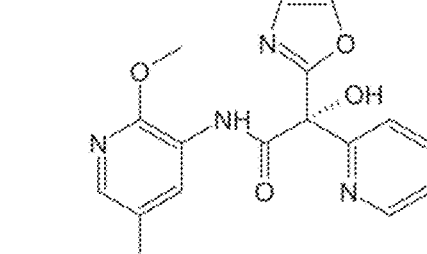
Figure 1N:
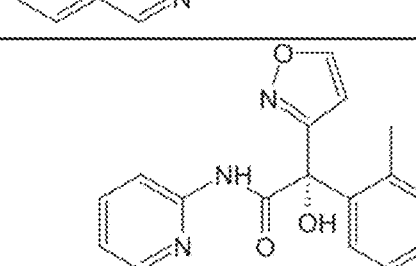
Figure 1O:
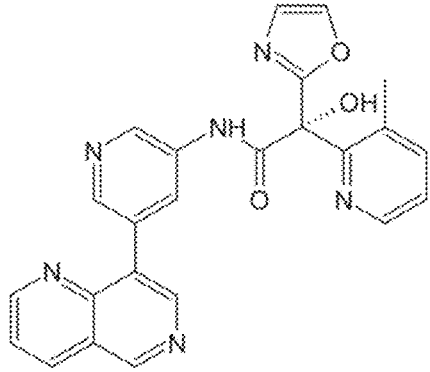
Figure 1O:
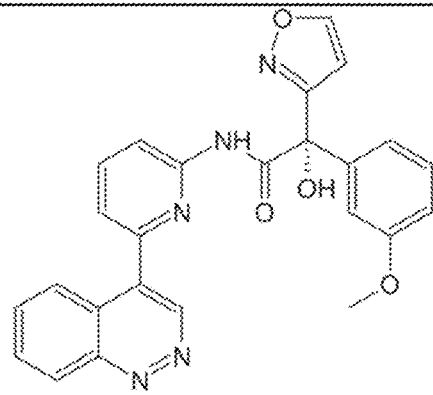
Figure 1O:
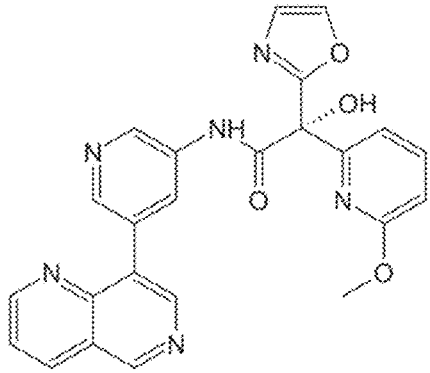
Figure 1O:
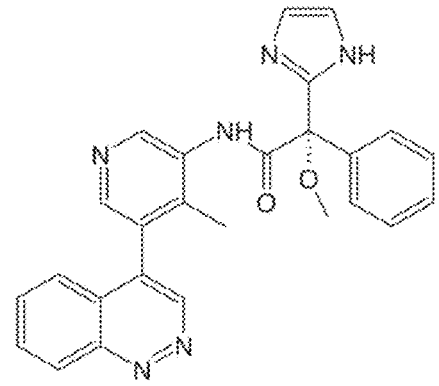
Figure 1P:
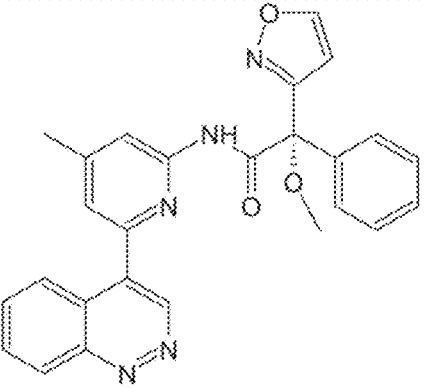
Figure 1P:
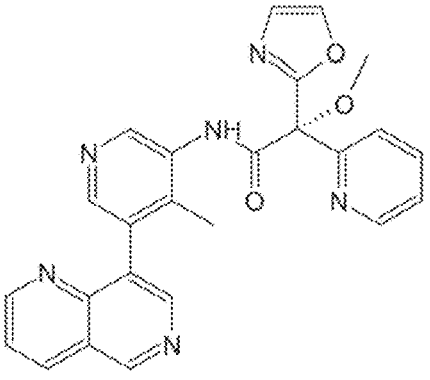
Figure 1P:
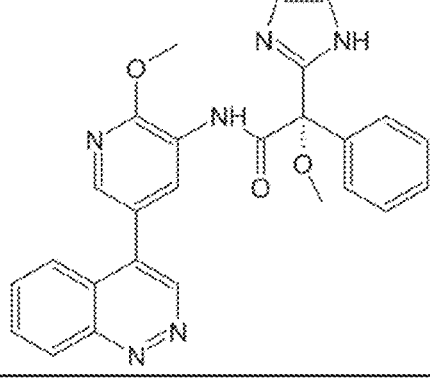
Figure 1P:
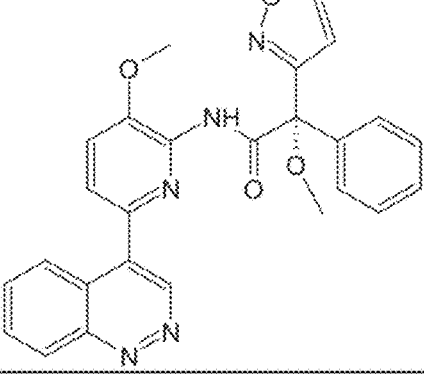
Figure 1Q:
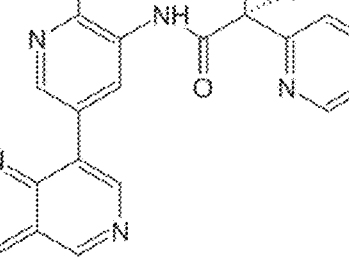
Figure 1Q:
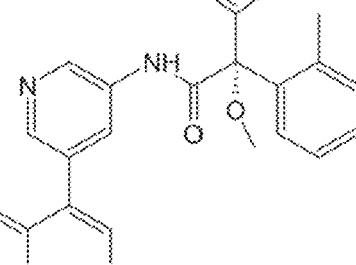
Figure 1Q:
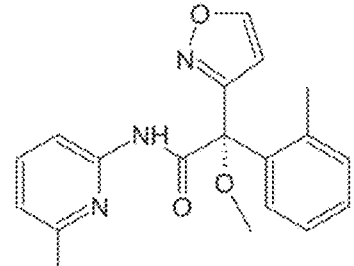
Figure 1Q:
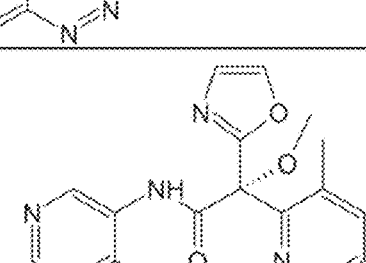
Figure 1R:
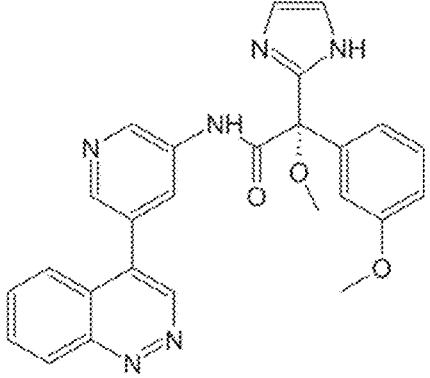
Figure 1R:
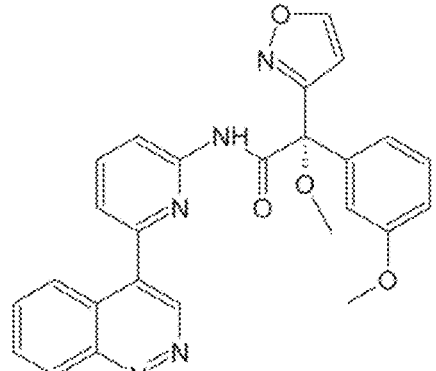

Unless otherwise stated, the following definitions are used throughout the present application.

Enantiomer: Optical isomer; chemical classification of molecules based on their ability to rotate the plain of polarization clockwise (+) or anti-clockwise (−).

Substantially pure: Having a purity of at least 90% by weight, preferably at least 95% by weight such as at least 98%, 99% or about 100% by weight.

The term "halogen" refers to fluorine, chlorine, bromine, and iodine. Fluorine, chlorine, and bromine are preferred.

The term "hetero atom" refers to an oxygen atom, a sulfur atom, and a nitrogen atom.

The term "alkyl" includes a monovalent straight or branched hydrocarbon group having one to eight carbon atom(s). Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. C1-C6 alkyl is preferred. C1-C4 alkyl or C1-C3 alkyl is further preferred. When a number of carbons is specified, it means "alkyl" having the carbon number within the range.

The term "alkenyl" includes a monovalent straight or branched hydrocarbon group having two to eight carbon atoms and one or more double bond(s). Examples include vinyl, allyl, 1-propenyl, 2-butenyl, 2-pentenyl, 2-hexenyl, 2-heptenyl, 2-octenyl, and the like. C2-C6 alkenyl is preferred. C2-C4 or C2-C3 alkenyl is further preferred.

The term "alkynyl" includes a monovalent straight or branched hydrocarbon group having two to eight carbon atoms and one or more triple bond(s). Examples include ethynyl, 1-propynyl, 2-propynyl, 2-butynyl, 2-pentynyl, 2-hexynyl, 2-heptynyl, 2-octynyl, and the like. C2-C6 alkynyl is preferred. C2-C4 or C2-C3 alkynyl is further preferred.

The term "cycloalkyl" includes a cycloalkyl having three to eight carbon atoms. Examples include cyclopropyl, cyclobutyl, cyclopentyl, cyclohexyl, cycloheptyl, cyclooctyl, and the like. C3-C6 cycloalkyl is preferred.

The term "cycloalkenyl" includes a cycloalkenyl having three to eight carbon atoms. Examples include cyclopropе- nyl, cyclobutenyl, cyclopentenyl, cyclohexenyl, cycloheptenyl, cyclooctentyl, and the like. C3-C6 cycloalkenyl is preferred.

The term "alkyloxy" includes a group wherein an oxygen atom is substituted with one "alkyl" as described herein. Examples include methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like. C1-C6 alkyloxy is preferred. C1-C4 alkyloxy or C1-C3 alkyloxy is further preferred. When a number of carbons is specified, it means "alkyloxy" having the carbon number within the range.

The term "alkenyloxy" includes a group wherein an oxygen atom is substituted with one "alkenyl" as described herein. Examples include vinyloxy, allyloxy, 1-propenyloxy, 2-butenyloxy, 2-pentenyloxy, 2-hexenyloxy, 2-heptenyloxy, 2-octenyloxy, and the like. C2-C6 alkenyloxy is preferred. Moreover, C2-C4 or C2-C3 alkenyloxy is further preferred. When a number of carbons is specified, it means "alkenyloxy" having the carbon number within the range.

The term "alkynyloxy" includes a group wherein an oxygen atom is substituted with one "alkynyl" as described herein. Examples include ethynyloxy, 1-propynyloxy, 2-propynyloxy, 2-butynyloxy, 2-pentynyloxy, 2-hexynyloxy, 2-heptynyloxy, 2-octynyloxy, and the like. C2-C6 alkynyloxy is preferred. C2-C4 or C2-C3 alkynyloxy is further preferred. When a number of carbons is specified, it means "alkynyloxy" having the carbon number within the range.

The term "cycloalkyloxy" includes a group wherein an oxygen atom is substituted with one "cycloalkyl" as described herein. Examples include cyclopropyloxy, cyclobutyloxy, cyclopentyloxy, cyclohexyloxy, cycloheptyloxy, and cyclooctyloxy. C3-C6 cycloalkyloxy is preferred. When a number of carbons is specified, it means "cycloalkyloxy" having the carbon number within the range.

The term "cycloalkenyloxy" includes a group wherein an oxygen atom is substituted with one "cycloalkenyl" as described herein. Examples include cyclopropenyloxy, cyclobutenyloxy, cyclopentenyloxy, cyclohexenyloxy, cycloheptenyloxy, and cyclooctenyloxy. C3-C6 cycloalkenyloxy is preferred. When a number of carbons is specified, it means "cycloalkenyloxy" having the carbon number within the range.

The term "alkylthio" includes a group wherein a sulfur atom is substituted with one "alkyl" as described herein. Examples include methylthio, ethylthio, n-propylthio, isopropylthio, n-butylthio, isobutylthio, sec-butylthio, tert-butylthio, n-pentylthio, isopentylthio, 2-pentylthio, 3-pentylthio, n-hexylthio, isohexylthio, 2-hexylthio, 3-hexylthio, n-heptylthio, n-octylthio, and the like. C1-C6 Alkylthio is preferred. C1-C4 alkylthio is further preferred. C1-C3, C1-C2, or C1 alkylthio is further preferred. When a number of carbons is specified, it means "alkylthio" having the carbon number within the range.

The term "alkenylthio" includes a group wherein a sulfur atom is substituted with one "alkenyl" as described herein. Examples include vinylthio, allylthio, 1-propenylthio, 2-butenylthio, 2-pentenylthio, 2-hexenylthio, 2-heptenylthio, 2-octenylthio, and the like. C2-C6 Alkenylthio is preferred. C2-C4 or C2-C3 alkylthio is further preferred. When a number of carbons is specified, it means "alkenylthio" having the carbon number within the range.

The term "alkynylthio" includes a group wherein a sulfur atom is substituted with one "alkynyl" as described herein. Examples include ethynylthio, 1-propynylthio, 2-propynylthio, 2-butynylthio, 2-pentynylthio, 2-hexynylthio, 2-heptynylthio, 2-octynylthio, and the like. C2-C6 alkynylthio is preferred. C2-C4 or C2-C3 alkynylthio is further preferred. When a number of carbons is specified, it means "alkynylthio" having the carbon number within the range.

The term "alkylsulfinyl" includes a group wherein sulfinyl is substituted with one "alkyl" as described herein. Examples include methylsulfinyl, ethylsulfinyl, n-propylsulfinyl, isopropylsulfinyl, n-butylsulfinyl, isobutylsulfinyl, sec-butyl sulfinyl, tert-butylsulfinyl, n-pentylsulfinyl, isopentylsulfinyl, 2-pentylsulfinyl, 3-pentylsulfinyl, n-hexylsulfinyl, isohexylsulfinyl, 2-hexylsulfinyl, 3-hexyl sulfinyl, n-heptylsulfinyl, n-octylsulfinyl, and the like. C1-C6 alkylsulfinyl is preferred. C1-C4 or C1-C3 alkylsulfinyl is further preferred.

The term "alkylsulfonyl" includes a group wherein sulfonyl is substituted with one "alkyl" as described herein. Examples include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl, and the like. C1-C6 alkylsulfonyl is preferred. C1-C4 or C1-C3 alkylsulfonyl is further preferred.

The term "alkylsulfonyloxy" includes a group wherein an oxygen atom is substituted with one "alkylsulfonyl" as described herein. Examples include methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, n-pentylsulfonyloxy, isopentylsulfonyloxy, 2-pentylsulfonyloxy, 3-pentylsulfonyloxy, n-hexylsulfonyloxy, isohexylsulfonyloxy, 2-hexylsulfonyloxy, 3-hexylsulfonyloxy, n-heptylsulfonyloxy, n-octylsulfonyloxy, and the like. C1-C6 alkylsulfonyl is preferred. C1-C4 or C1-C3 alkylsulfonyl is further preferred.

The term "cycloalkylthio" includes a group wherein a sulfur atom is substituted with one "cycloalkyl" as described herein. Examples include cyclopropylthio, cyclobutylthio, cyclopentylthio, cyclohexylthio, cycloheptylthio, cyclooctylthio, and the like. C3-C6 cycloalkylthio is preferred. When a number of carbons is specified, it means "cycloalkylthio" having the carbon number within the range.

The term "cycloalkylsulfinyl" includes a group in which sulfinyl is substituted with one "cycloalkyl" as described herein. Examples include cyclopropylsulfinyl, cyclobutylsulfinyl, cyclopentylsulfinyl, cyclohexylsulfinyl, cycloheptylsulfinyl, and cyclooctylsulfinyl. C3-C6 cycloalkylsulfinyl is preferred.

The term "cycloalkylsulfonyl" includes a group in which sulfonyl is substituted with one "cycloalkyl" as described herein. Examples include cyclopropylsulfonyl, cyclobutylsulfonyl, cyclopentylsulfonyl, cyclohexylsulfonyl, cycloheptylsulfonyl, and cyclooctylsulfonyl. C3-C6 cycloalkylsulfonyl is preferred.

The term "cycloalkylsulfonyloxy" includes a group in which an oxygen atom is substituted with one "cycloalkylsulfonyl" as described herein. Examples include cyclopropylsulfonyloxy, cyclobutylsulfonyloxy, cyclopentyl sulfonyloxy, cyclohexyl sulfonyloxy, cycloheptylsulfonyloxy, and cyclooctylsulfonyloxy. C6-C3 cycloalkylsulfonyloxy is preferred.

The term "cycloalkenylthio" includes a group in which a sulfur atom is substituted with one "cycloalkenyl" as described herein. Examples include cyclopropenylthio, cyclobutenylthio, cyclopentenylthio, cyclohexenylthio, cycloheptenylthio, and cyclooctenylthio. C3-C6 cycloalkenylthio is preferred. When a number of carbons is specified, it means "cycloalkenylthio" having the carbon number within the range.

The term "cycloalkenylsulfinyl" includes a group in which sulfinyl is substituted with one "cycloalkenyl" as described herein. Examples include cyclopropenylsulfinyl, cyclobutenylsulfinyl, cyclopentenyl sulfinyl, cyclohexenylsulfinyl, cycloheptenylsulfinyl, and cyclooctenylsulfinyl. C3-C6 cycloalkenylsulfinyl is preferred.

The term "cycloalkenylsulfonyl" includes a group in which sulfonyl is substituted with one "cycloalkenyl" as described herein. Examples include cyclopropenylsulfonyl, cyclobutenylsulfonyl, cyclopentenylsulfonyl, cyclohexenylsulfonyl, cycloheptenylsulfonyl, and cyclooctenylsulfonyl. C3-C6 cycloalkenylsulfonyl is preferred.

The term "cycloalkenylsulfonyloxy" includes a group in which an oxygen atom is substituted with one "cycloalkenylsulfonyl" described as described herein. Examples include cyclopropenylsulfonyloxy, cyclobutenylsulfonyloxy, cyclopentenylsulfonyloxy, cyclohexenylsulfonyloxy, cycloheptenylsulfonyloxy, and cyclooctenylsulfonyloxy. C3-C6 cycloalkenylsulfonyloxy is preferred.

The term "alkyloxycarbonyl" includes a group in which carbonyl is substituted with one "alkyloxy" as described herein. Examples include methyloxycarbonyl, ethyloxycarbonyl, n-propyloxycarbonyl, isopropyloxycarbonyl, n-butyloxycarbonyl, tert-butyloxycarbonyl, and n-pentyloxycarbonyl. C1-C6, C1-C4, or C1-C3 alkyloxycarbonyl is preferred. C1-C2 alkyloxycarbonyl is further preferred.

The term "alkenyloxycarbonyl" includes a group in which carbonyl is substituted with one "alkenyloxy" as described herein. Examples include vinyloxycarbonyl, allyloxycarbonyl, 1-propenyloxycarbonyl, 2-butenyloxycarbonyl, and 2-pentenyloxyarbonyl. C2-C6, C2-C4, or C2-C3 alkyloxycarbonyl is preferred.

The term "alkynyloxycarbonyl" includes a group in which carbonyl is substituted with one "alkynyloxy" as described herein. Examples include ethynyloxycarbonyl, 1-propynyloxycarbonyl, 2-propynyloxycarbonyl, 2-butynyloxyarbonyl, and 2-pentynyloxycarbonyl. C2-C6, C2-C4, or C2-C3 alkynyloxycarbonyl is preferred.

The term "acyl" includes alkylcarbonyl wherein the part of alkyl is "alkyl" as described herein, alkenylcarbonyl wherein the part of alkenyl is "alkenyl" as described herein, alkynylcarbonyl wherein the part of alkynyl is "alkynyl" as described herein, cycloalkylcarbonyl wherein the part of cycloalkyl is "cycloalkyl" as described herein, arylcarbonyl wherein the part of aryl is "aryl" as described herein, heteroarylcarbonyl wherein the part of heteroaryl is "heteroaryl" as described herein, and non-aromatic heterocyclic-carbonyl wherein the part of non-aromatic heterocyclic group is "non-aromatic heterocyclic group" as described herein. "Alkyl," "alkenyl," "alkynyl," "cycloalkyl," "aryl," "heteroaryl," and "non-aromatic heterocyclic group" may be substituted respectively with substituent groups exemplified in "optionally substituted alkyl," "optionally substituted alkenyl," "optionally substituted alkynyl," "optionally substituted cycloalkyl," "optionally substituted aryl," "optionally substituted heteroaryl," and "optionally substituted non-aromatic heterocyclic group" as described herein. Examples of the acyl group include acetyl, propionyl, butyroyl, cyclohexylcarbonyl, benzoyl, pyridinecarbonyl, and the like.

The term "optionally substituted amino" includes an amino group which may be substituted with one or two group(s) of "alkyl" as described herein, "alkenyl" as described herein, "alkynyl" as described herein, "cycloalkyl" as described herein, "cycloalkynyl" as described herein, "aryl" as described herein, "heteroaryl" as described herein, "acyl" as described herein, "alkyloxycarbonyl" as described herein, "alkenyloxycarbonyl" as described herein, "alkynyloxycarbonyl" as described herein, "alkyl sulfonyl," "alkenyl sulfonyl," "alkynylsulfonyl," "aryl sulfonyl," and/or "heteroarylsulfonyl" as described herein. Examples of the optionally substituted amino group include amino, methylamino, dimethylamino, ethylamino, diethylamino, ethylmethylamino, benzylamino, acetylamino, benzoylamino, methyloxycarbonylamino, and methanesulfonylamino. Amino, methylamino, dimethylamino, ethylmethylamino, diethylamino, acetylamino, and methanesulfonylamino are preferred.

The term "optionally substituted carbamoyl" includes an aminocarbonyl group wherein the part of optionally substituted amino is "optionally substituted amino" as described herein. Examples of the optionally substituted carbamoyl group includes carbamoyl, N-methylcarbamoyl, N,N-dimethyl carbamoyl, N-ethyl-N-methylcarbamoyl, N,N-diethylcarbamoyl, N-phenylcarbamoyl, N-benzylcarbamoyl, N-acetylcarbamoyl, and N-methylsulfonylcarbamoyl etc. Carbamoyl, N-methylcarbamoyl, N,N-dimethylcarbamoyl, and N-methylsulfonylcarbamoyl etc. are preferred.

The term "optionally substituted sulfamoyl" includes an aminosulfonyl group wherein the part of optionally substituted amino is "optionally substituted amino" as described herein. Examples of the optionally substituted sulfamoyl group include sulfamoyl, N-methylsulfamoyl, N,N-dimethylsulfamoyl, N-ethyl-N-methyl sulfamoyl, N,N-diethylsulfamoyl, N-phenylsulfamoyl, N-benzylsulfamoyl, N-acetylsulfamoyl, and N-methylsulfonylsulfamoyl etc. Sulfamoyl, N-methylsulfamoyl, N,N-dimethylsulfamoyl, and N-methylsulfonylsulfamoyl etc. are preferred.

The term "alkylene" means a straight or branched alkylene group having one to eight carbon atom(s). Examples include methylene, ethylene, 1-methylethylene, trimethylene, 1-methyltrimethylene, pentamethylene, hexamethylene, and the like. C1-C4 or C1-3 alkylenes are preferred. C1-C2 or C1 alkylene is further preferred.

The term "aryl" includes an aromatic monocyclic or aromatic fused cyclic hydrocarbons. It may be fused with "cycloalkyl" as described herein, "cycloalkenyl" as described herein or "non-aromatic heterocyclic group" as described herein at any possible position. Both of monocyclic ring and fused ring may be substituted at any position. Examples include phenyl, 1-naphthyl, 2-naphthyl, anthryl, tetrahydronaphthyl, 1,3-benzodioxolyl, 1,4-benzodioxanyl etc. Phenyl, 1-naphthyl, and 2-naphthyl are preferred. Phenyl is further preferred.

The term "non-aromatic heterocyclic group" includes a 5- to 7-membered non-aromatic heterocyclic ring containing one or more of heteroatom(s) selected independently from oxygen, sulfur, and nitrogen atoms or a multicyclic ring formed by fusing the two or more rings thereof. Examples include pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., 2-imidazolinyl), pyrazolidinyl (e.g., 1-pyrazolidinyl, 2-pyrazolidinyl), pyrazolinyl (e.g., 1-pyrazolinyl, 2-pyrazolinyl, 3-pyrazolinyl), piperidyl (e.g., piperidino, 2-piperidyl), piperazinyl (e.g., 1-piperazinyl), indolinyl (e.g., 1-indolinyl), isoindolinyl, morpholinyl (e.g., morpholino, 3-morpholinyl) etc.

The term "heteroaryl" includes a 5- to 6-membered aromatic ring containing one or more of heteroatom(s) selected independently from oxygen, sulfur, and nitrogen atoms. It may be fused with "cycloalkyl" as described herein, "aryl" as described herein, "non-aromatic heterocyclic group" as described herein, or other heteroaryl at any possible position. The heteroaryl group may be substituted at any position whenever it is a monocyclic ring or a fused ring. Examples include pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolizinyl (e.g., 2-indolizinyl, 6-indolizinyl), isoindolinyl (e.g., 2-isoindolinyl), indolyl (e.g., 1-indolyl, 2-indolyl, 3-indolyl), indazolyl (e.g., 3-indazolyl), purinyl (e.g., 8-purinyl), quinolizinyl (e.g., 2-quinolizinyl), isoquinolyl (e.g., 3-isoquinolyl), quinolyl (e.g., 2-quinolyl, 5-quinolyl), phthalazinyl (e.g., 1-phthalazinyl), naphthyridinyl (e.g., 2-naphthyridinyl), quinolinyl (e.g., 2-quinolinyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzoimidazolyl (e.g., 2-benzoimidazolyl), benzoisoxazolyl (e.g., 3-benzoisoxazolyl), benzooxazolyl (e.g., 2-benzooxazolyl), benzooxadiazolyl (e.g., 4-benzooxadiazolyl), benzoisothiazolyl (e.g., 3-benzoisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), and benzodioxolyl (e.g., 1,3-benzodioxolyl), etc.

The term "aryloxy" includes a group in which an oxygen atom is substituted with one "aryl" as described herein. Examples include phenyloxy and naphthyloxy, etc.

The term "arylthio" includes a group in which a sulfur atom is substituted with one "aryl" as described herein. Examples include phenylthio and naphthylthio, etc.

The term "arylsulfinyl" includes a group in which sulfinyl is substituted with one "aryl" as described herein. Examples include phenylsulfinyl and naphthylsulfinyl, etc.

The term "arylsulfonyl" includes a group in which sulfonyl is substituted with one "aryl" as described herein. Examples include phenylsulfonyl and naphthylsulfoinyl, etc.

Examples of "arylsulfonyloxy" include phenylsulfonyloxy and naphthylsulfonyloxy, etc.

The term "aryloxycarbonyl" includes a group in which carbonyl is substituted with one "aryloxy" as described herein. Examples include phenyloxycarbonyl, 1-naphthyloxycarbonyl and 2-naphthyloxycarbonyl, etc.

The term "heteroaryloxy" includes a group in which an oxygen atom is substituted with one "heteroaryl" as described herein. Examples include pyrrolyloxy, furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, pyridazinyloxy, tetrazolyloxy, oxadiazolyloxy, thiadiazolyloxy, indolizinyloxy, isoindolinyloxy, indolyloxy, indazolyloxy, purinyloxy, quinolizinyloxy, isoquinolyloxy, quinolyloxy, phthalazinyloxy, naphthyridinyloxy, quinolinyloxy, quinazolinyloxy, cinnolinyloxy, pteridinyloxy, carbazolyloxy, phenanthridinyloxy, acridinyloxy, dibenzofuranyloxy, benzoimidazolyloxy, benzoi soxazolyl oxy, benzooxazolyloxy, benzooxadiazolyloxy, benzoi sothiazolyloxy, benzothiazolyloxy, b enzofuryloxy, benzothienyloxy, dibenzothienyloxy, and benzodioxolyloxy. Preferred are furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, and pyridazinyloxy.

The term "heteroarylthio" includes a group in which a sulfur atom is substituted with one "heteroaryl" as described herein. Examples include pyrrolylthio, furylthio, thienylthio, imidazolylthio, pyrazolylthio, isothiazolylthio, isoxazolylthio, oxazolylthio, thiazolylthio, pyridylthio, pyrazinylthio, pyrimidinylthio, pyridazinylthio, tetrazolylthio, oxadiazolylthio, thiadiazolylthio, indolizinylthio, isoindolinylthio, indolylthio, indazolylthio, purinylthio, quinolizinylthio, isoquinolylthio, quinolylthio, phthalazinylthio, naphthyridinylthio, quinolinylthio, quinazolinylthio, cinnolinylthio, pteridinylthio, carbazolylthio, phenanthridinylthio, acridinylthio, dibenzofuranylthio, benzoimidazolylthio, benzoisoxazolylthio, benzooxazolylthio, benzooxadiazolylthio, benzoisothiazolylthio, benzothiazolylthio, benzofurylthio, benzothienylthio, dibenzothienylthio, and benzodioxolylthio, etc. Preferred are furylthio, thienylthio, imidazolylthio, pyrazolylthio, isothiazolylthio, isoxazolylthio, oxazolylthio, thiazolylthio, pyridylthio, pyrazinylthio, pyrimidinylthio, and pyridazinylthio.

The term "heteroarylsulfinyl" includes a group in which sulfinyl is substituted with one "heteroaryl" as described herein. Examples include pyrrolylsulfinyl, furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, pyridazinylsulfinyl, tetrazolylsulfinyl, oxadiazolylsulfinyl, thiadiazolylsulfinyl, indolizinylsulfinyl, isoindolylsulfinyl, indolylsulfinyl, indazolylsulfinyl, purinylsulfinyl, quinolizinylsulfinyl, isoquinolylsulfinyl, quinolylsulfinyl, phthalazinylsulfinyl, naphthyridinylsulfinyl, quinolinylsulfinyl, quinazolinylsulfinyl, cinnolinylsulfinyl, pteridinylsulfinyl, carbazolylsulfinyl, phenanthridinylsulfinyl, acridinylsulfinyl, dibenzofuranylsulfinyl, benzoimidazolylsulfinyl, benzoisoxazolylsulfinyl, benzooxazolylsulfinyl, benzooxadiazolylsulfinyl, benzoisothiazolylsulfinyl, benzothiazolylsulfinyl, benzofurylsulfinyl, benzothienylsulfinyl, dibenzothienylsulfinyl, and benzodioxolylsulfinyl. Furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, and pyridazinylsulfinyl are preferred.

The term "heteroarylsulfonyl" includes a group in which sulfonyl is substituted with one "heteroaryl" as described herein. Examples include pyrrolylsulfonyl, furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, pyridazinylsulfonyl, tetrazolylsulfonyl, oxadiazolylsulfonyl, thiadiazolylsulfonyl, indolizinylsulfonyl, isoindolylsulfonyl, indolylsulfonyl, indazolylsulfonyl, purinylsulfonyl, quinolizinylsulfonyl, isoquinolylsulfonyl, quinolylsulfonyl, phthalazinylsulfonyl, naphthilidinylsulfonyl, quinolinylsulfonyl, quinazolinylsulfonyl, cinnolinylsulfonyl, pteridinylsulfonyl, carbazolylsulfonyl, phenanthridinylsulfonyl, acridinylsulfonyl, dibenzofuranylsulfonyl, benzoimidazolylsulfonyl, benzoisoxazolylsulfonyl, benzooxazolylsulfonyl, benzooxadiazolylsulfonyl, benzoisothiazolylsulfonyl, benzothiazolylsulfonyl, benzofurylsulfonyl, benzothienylsulfonyl, dibenzothienylsulfonyl, and benzodioxolylsulfonyl, etc. Furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, and pyridazinylsulfonyl are preferred.

The term "heteroarylsulfonyloxy" includes a group in which an oxygen atom is substituted with one "heteroarylsulfonyl" as described herein. Examples include pyrrolylsulfonyloxy, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, pyridazinylsulfonyloxy, tetrazolylsulfonyloxy, oxadiazolylsulfonyloxy, thiadiazolylsulfonyloxy, indolizinylsulfonyloxy, isoindolylsulfonyloxy, indolylsulfonyloxy, indazolylsulfonyloxy, purinylsulfonyloxy, quinolizinylsulfonyloxy, isoquinolylsulfonyloxy, quinolylsulfonyloxy, phthalazinylsulfonyloxy, naphthilidinylsulfonyloxy, quinolinyl sulfonyloxy, quinazolinylsulfonyloxy, cinnolinylsulfonyloxy, pteridinylsulfonyloxy, carbazolylsulfonyloxy, phenanthridinylsulfonyloxy, acridinylsulfonyloxy, dibenzofuranylsulfonyloxy, benzoimidazolylsulfonyloxy, benzoisoxazolylsulfonyloxy, benzooxazolylsulfonyloxy, benzooxadiazolylsulfonyloxy, benzoisothiazolylsulfonyloxy, benzothiazolylsulfonyloxy, benzofurylsulfonyloxy, benzothienylsulfonyloxy, dibenzothienylsulfonyloxy, and benzodioxolylsulfonyloxy, etc. Furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, and pyridazinylsulfonyloxy are preferred.

The term "aromatic carbocyclic ring" includes an aromatic monocyclic or aromatic fused carbocyclic ring. Examples include a benzene ring, a naphthalene ring, and an anthracene ring. A benzene ring is preferred.

The term "aromatic heterocyclic ring" includes an aromatic monocyclic or aromatic fused heterocyclic ring. Examples include a pyrrole ring, a furan ring, a thiophen ring, a pyrazole ring, an imidazole ring, an isothiazole ring, an isoxazole ring, an oxazole ring, a thiazole ring, a pyrazine ring, a pyrimidine ring, a pyridazine ring, a tetrazole ring, an oxadiazole ring, a thiadiazole ring, an indolizine ring, an isoindole ring, an indole ring, an indazole ring, a purine ring, a quinolizine ring, an isoquinoline ring, a quinoline ring, a phthalazine ring, a naphthyridine ring, a quinazoline ring, a cinnoline ring, a pteridine ring, a carbazole ring, a phenanthridine ring, an acridine ring, a dibenzofuran ring, a benzimidazole ring, a benzisoxazole ring, a benzoxazole ring, a benzoxadiazole ring, a benzisothiazole ring, a benzothiazole ring, a benzofuran ring, a benzothiophene ring, a dibenzothiophene ring, and a benzodixolane ring. Preferred are a pyridine ring, a furan ring, and a thiophen ring.

The term "C1-C6 alkylene" includes a straight or branched alkylene group having one to six carbon atom(s). Examples include —CH$_2$—, —CH(CH$_3$)—, —C(CH$_3$)$_2$—, —CH$_2$CH$_2$—, —CH(CH$_3$)CH$_2$—, —C(CH$_3$)$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, and —CH$_2$CH$_2$CH$_2$CH$_2$CH$_2$CH$_2$—. Preferred are —CH$_2$—, —CH$_2$CH$_2$—, —CH$_2$CH$_2$CH$_2$—, and —CH$_2$CH$_2$CH$_2$CH$_2$—.

The term "alkylene optionally containing one or two heteroatom(s)" of "optionally substituted alkylene optionally containing one or two heteroatom(s)" includes a straight or branched alkylene group having one to six carbon atoms, optionally containing one or two heteroatom(s) which may be substituted with "alkyl" as described herein. Examples include —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$O—, —OCH$_2$—, —CH$_2$O—, —OCH$_2$CH$_2$—, —CH$_2$S—, —CH$_2$CH$_2$S—, —SCH$_2$CH$_2$—, —CH$_2$CH$_2$OCH$_2$CH$_2$—, —OCH$_2$CH$_2$O—, —OCH$_2$O—, —NHCH$_2$—, —N(CH$_3$)CH$_2$—, —N$^+$(CH$_3$)$_2$CH$_2$—, —NHCH$_2$CH$_2$CH$_2$—, and —N(CH$_3$)CH$_2$CH$_2$CH$_2$—, etc. Preferred are —CH$_2$—, —CH$_2$CH$_2$—, —CH$_2$CH$_2$CH$_2$—, —CH$_2$CH$_2$CH$_2$CH$_2$—, —OCH$_2$CH$_2$O—, —OCH$_2$O—, and —N(CH$_3$)CH$_2$CH$_2$CH$_2$—.

The term "alkenylene optionally containing one or two heteroatom(s)" of "optionally substituted alkenylene optionally containing one or two heteroatom(s)" includes a straight or branched alkenylene group having two to six carbon atoms, optionally containing one or two heteroatom(s) which may be substituted with "alkyl" as described herein. Examples include —CH=CHCH=CH—, —CH=CHO—, —OCH=CH—, —CH=CHS—, —SCH=CH—, —CH=CHNH—, —NHCH=CH—, —CH=CH—CH=N—, and —N=CH—CH=CH—. Preferred are, —CH=CHCH=CH—, —CH=CHCH=N—, and —N=CHCH=CH—.

The term "alkynylene optionally containing one or two heteroatom(s)" includes a straight or branched alkynylene group having two to six carbon atoms, optionally containing one or two heteroatom(s) which may be substituted with "alkyl" as described herein. Examples include —C≡CCH$_2$—, —CH$_2$C≡CCH$_2$—, —CH$_2$C≡CCH$_2$O—, —OCH$_2$CCH—, —CH$_2$C≡CCH$_2$S—, —SCH$_2$C≡CH—, —CH$_2$C≡CCH$_2$NH—, —NHCH$_2$C≡CH—, —CH$_2$C≡CCH$_2$N(CH$_3$)—, and —N(CH$_3$)CH$_2$C≡CH—. Especially, —CH$_2$C≡CCH$_2$—, and —OCH$_2$C≡CH— are preferred.

The term "3- to 8-membered nitrogen-containing non-aromatic heterocyclic ring" includes a ring of any of the formulas described as such in U.S. Pat. No. 8,143,285, which is incorporated herein by reference in its entirety.

The term "3- to 8-membered nitrogen-containing aromatic heterocyclic ring" includes a 3- to 8-membered aromatic heterocyclic ring containing one or more of nitrogen atom(s), and further optionally an oxygen atom and/or sulfur atom in the ring. Examples include pyrrolyl (e.g., 1-pyrrolyl, 2-pyrrolyl, 3-pyrrolyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), and thiadiazolyl (e.g., 1,3,4-thiadiazolyl).

The term "4- to 8-membered nitrogen-containing heterocyclic ring containing one or two nitrogen atom(s)" means a ring of any of the formulas described as such in U.S. Pat. No. 8,143,285, which is incorporated herein by reference in its entirety.

The term "oxo" refers to an =O group.

"Optionally substituted" is used interchangeably herein with "substituted or unsubstituted."

In the present specification, examples of substituents in "optionally substituted alkyl," "optionally substituted alkyloxy," "optionally substituted alkylthio," "optionally substituted alkylsulfinyl," "optionally substituted alkylsulfonyl," "optionally substituted alkylsulfonyloxy," and "the optionally substituted alkyloxycarbonyl" include cycloalkyl, alkylene optionally containing one or two heteroatom(s), hydroxyl, oxo, alkyloxy optionally substituted with a substituent group A at one to three position(s), thiol, alkylthio, halogen, nitro, cyano, carboxyl, sulfino (—SO$_2$H), alkyloxycarbonyl, optionally substituted amino, optionally substituted carbamoyl, acyl, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), an optionally substituted non-aromatic heterocyclic ring group (e.g., morpholinyl, pyrrolidinyl, piperazinyl) which may be substituted with a substituent group C at one to three position(s), aryloxy (e.g., phenyloxy) optionally substituted with a substituent group B at one to three position(s), alkylsulfonyl, and the like. The above-referenced "optionally substituted" moieties can be substituted with one to three of the above-referenced substituent(s) at any possible position.

In the present specification, examples of substituents in "optionally substituted alkenyl," "optionally substituted alkynyl," "optionally substituted alkenyloxy," "optionally substituted alkynyloxy," "optionally substituted alkenylthio," "optionally substituted alkynylthio," "optionally substituted alkenyloxycarbonyl," "optionally substituted alkynyloxycarbonyl," "optionally substituted cycloalkyl," "optionally substituted cycloalkenyl," "optionally substituted cycloalkyloxy, "optionally substituted cycloalkenyloxy," "optionally substituted cycloalkylthio," "optionally substituted cycloalkenylthio," "optionally substituted cycloalkylsulfinyl," "optionally substituted cycloalkenylsulfinyl," "optionally substituted cycloalkylsulfonyl," "optionally substituted cycloalkenylsulfonyl," "optionally substituted cycloalkylsulfonyloxy," "optionally substituted cycloalkenylsulfonyloxy," "optionally substituted alkenyloxycarbonyl," "optionally substituted alkylene," "optionally substituted C1-C6 alkylene," "optionally substituted alkylene optionally containing one or two heteroatom(s)," "optionally substituted alkenylene," "optionally substituted alkenylene optionally containing one or two heteroatom(s)," "optionally substituted alkynylene," and "optionally substituted alkynylene optionally containing one or two heteroatom(s)" include alkyl (such as dialkyl) optionally substituted with a substituent group D at one to three position(s), cycloalkyl, hydroxyl, oxo, alkyloxy optionally substituted with a substituent group A at one to three position(s), thiol, alkylthio, halogen, nitro, cyano, carboxyl, sulfino, alkyloxycarbonyl, optionally substituted amino, optionally substituted carbamoyl, acyl acyloxy, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), non-aromatic heterocyclic group (e.g., morpholinyl, pyrrolidinyl, piperazinyl) optionally substituted with a substituent group C at one to three position(s), aryloxy (e.g., phenyloxy) optionally substituted with a substituent group C at one to three position(s), alkylsulfonyl, and the like. The above-referenced "optionally substituted" moieties can be substituted with one or more of the above-referenced substituent(s) at any possible position.

In the present specification, examples of substituents in "optionally substituted aryl," "optionally substituted phenoxy," "optionally substituted aryloxy," "optionally substituted phenylthio," "optionally substituted arylthio," "optionally substituted arylsulfinyl," "optionally substituted aryl sulfonyl," "optionally substituted arylsulfonyloxy," "optionally substituted heteroaryl," "optionally substituted heteroaryloxy," "optionally substituted heteroarylthio," "optionally substituted heteroarylsulfinyl," "optionally substituted heteroarylsulfonyl," "optionally substituted heteroarylsulfonyloxy," "optionally substituted non-aromatic heterocyclic group," "optionally substituted C6 arene-1,4-diamine-N$^1$,N$^4$-diyl," and substituted C6 arene-1,4-diamine-N$^1$,N$^4$-diyl," include alkyl optionally substituted with a substituent group D at one to three position(s), cycloalkyl, alkenyl, alkynyl, hydroxyl, alkyloxy optionally substituted with a substituent group A at one to three position(s), aryloxy (e.g., phenoxy) optionally substituted with a substituent group B at one to three position(s), thiol, alkylthio, halogen, nitro, cyano, carboxyl, sulfino, alkyloxycarbonyl, acyl, alkylsulfonyl, optionally substituted amino, optionally substituted carbamoyl, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), non-aromatic heterocyclic group (e.g., morpholinyl, pyrrolidinyl, piperazinyl) optionally substituted with a substituent group C at one to three position(s), and the like. The above-referenced "optionally substituted" moieties can be substituted with one or more of the above-referenced substituent(s) at any possible position.

Substituent group A is comprised of halogen and phenyl optionally substituted with one to three substituent(s) selected from the Substituent group B.

Substituent group B is comprised of halogen, alkyl, alkyloxy, cyano, and nitro.

Substituent group C is comprised of halogen and alkyl.

Substituent group D is comprised of halogen and alkyloxy.

In versions in which any R group (e.g., $R^1$, $R^2$, and/or $R^L$) is designated as "not hydrogen," the R group is independently selected from the group consisting of halogen, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, thiol, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

For any R group defined as "not hydrogen," the R group can further be defined as "not hydrogen or halogen." In cases in which the R group is further defined as "not hydrogen or halogen," the R group is independently selected from the group consisting of optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, thiol, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

Unless otherwise defined, the term "substituted" refers to a moiety comprising any substituent described herein.

In some versions, at least one substituent in any pair of substituents ($R^2$ groups) of constituent ring atoms, unless explicitly specified otherwise, is a non-cyclic moiety. In some versions, at least one substituent in any pair of substituents of constituent ring atoms, unless explicitly specified otherwise, is independently hydrogen, halogen, or optionally substituted C1-C6 alkyl. In some versions, at least one substituent in any pair of substituents of constituent ring atoms, unless explicitly specified otherwise, is independently hydrogen or halogen. In some versions, at least one substituent in any pair of substituents of constituent ring atoms, unless explicitly specified otherwise, is hydrogen. "Vicinal" in this context refers to any two substituents bonded to adjacent constituent ring atoms.

In the course of the methods of the present invention, a therapeutically effective amount of a compound of the invention can be administered to an animal, including mammals and humans, in many ways. While in the preferred embodiment, the compounds of the invention are administered orally, parenterally, or topically, other forms of administration such as through medical compounds or aerosols are also contemplated.

For oral administration, the effective amount of compounds may be administered in, for example, a solid, semi-solid, liquid, or gas state. Specific examples include tablet, capsule, powder, granule, solution, suspension, syrup, and elixir agents. However, the compounds are not limited to these forms.

To formulate the compounds of the invention into tablets, capsules, powders, granules, solutions, or suspensions, the compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, cyclodextrins, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the compounds of the present invention may be administered rectally or by injection. For rectal administration, a suppository may be used. The suppository may be prepared by mixing the compounds of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection, the compounds of the present invention may be injected hypodermically, intracutaneously, intravenously, or intramuscularly. Medicinal drugs for such injection may be prepared by dissolving, suspending or emulsifying the compounds of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

To formulate the compounds of the invention into suspensions, syrups, or elixirs, a pharmaceutically suitable solvent may be used. Included among these is the non-limiting example of water.

For topical administration, topical formulations can be in a form of gel, cream, lotion, liquid, emulsion, ointment, spray, solution, suspension, and patches. Inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

The compounds of the invention may also be used together with an additional compound having other pharmaceutically suitable activity to prepare a medicinal drug. A drug, either containing a compound of the invention as a stand-alone compound or as part of a composition, may be used in the treatment of subjects in need thereof.

The compounds of the invention may also be administered in the form of an aerosol or inhalant prepared by charging the compounds in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

The compounds of the invention may be administered as a pharmaceutical composition, such as tablets, capsules, solutions, or emulsions. Administration of other forms of the compounds described in this invention, including but not limited to esters thereof, pharmaceutically suitable salts thereof, metabolites thereof, structurally related compounds thereof, analogs thereof, and combinations thereof, in a single dose or a multiple dose, are also contemplated by the present invention.

The compounds of the invention may also be administered as a nutritional additive, either as a food or nutraceutical supplement.

The term "treating" refers to the full or partial reduction of a condition or any aspect, complication, or symptom thereof. Examples include eliminating the condition, reducing the severity of the condition, reducing the number of symptoms or complications of the condition, eliminating a particular symptom or complication of the condition, reducing the severity of one or more symptoms or complications of the condition, or eliciting any other change in the condition of the patient that improves the therapeutic outcome.

The term "preventing" refers to the full or partial prophylaxis of a condition or any aspect, complication or symptom thereof. Examples include prophylactically eliminating the condition, prophylactically reducing the severity of the condition, prophylactically reducing the number of symptoms or complications of the condition, prophylactically eliminating a particular symptom or complication of the condition, prophylactically reducing the severity of one or more symptoms or complications of the condition, or prophylactically eliciting any other change in the condition of the patient that improves the therapeutic outcome.

The compounds described in this invention are preferably used and/or administered in the form of a composition. In some versions, the composition comprises a single enantiomer of any compound provided herein. In some versions, the composition comprises a racemic mixture of any compound provided herein. Suitable compositions are, preferably, a pharmaceutical composition, a foodstuff, or a food supplement. These compositions provide a convenient form in which to deliver the compounds. Compositions of the invention may comprise an antioxidant in an amount effective to increase the stability of the compounds with respect to oxidation or solubility.

The amount of compound that is administered in the method of the invention or that is for administration in the use of the invention is any suitable amount. Examples include from 1 ng/kg body weight to 20 g/kg body weight, such as from 1 µg/kg body weight to 1 g/kg body weight or from 0.5 mg/kg body weight to 50 mg/kg body weight of compound per day. Suitable compositions can be formulated accordingly. Those of skill in the art of dosing of biologically active agents will be able to develop particular dosing regimens for various subjects based on known and well understood parameters.

A preferred composition according to the invention is a pharmaceutical composition, such as in the form of tablets, pills, capsules, caplets, multiparticulates (including granules, beads, pellets and micro-encapsulated particles), powders, elixirs, syrups, suspensions, and solutions. Pharmaceutical compositions will typically comprise a pharmaceutically acceptable diluent or carrier. Pharmaceutical compositions are preferably adapted for administration parenterally or orally. Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the compounds on the subject.

Pharmaceutically acceptable carriers suitable for use in such compositions are well known in the art of pharmacy.

The compositions of the invention may contain 0.01-99% by weight of the compounds of the invention. The compositions of the invention are generally prepared in unit dosage form. Examples of unit dosages of the compounds of the invention include from 0.1 mg to 2000 mg, such as 50 mg to 1000 mg. The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like.

In general, the term "carrier" represents a composition with which the compounds described may be mixed, be it a pharmaceutical carrier, foodstuff, nutritional supplement, or dietary aid. The materials described above may be considered carriers for the purposes of the invention. In certain embodiments of the invention, the carrier has little to no biological activity on the compounds of the invention.

Dose: The methods of the present invention can comprise administering a therapeutically effective amount of compound to an animal in need thereof. The effective amount of compound depends on the form of the compound administered, the duration of the administration, the route of administration (e.g., oral or parenteral), the age of the animal, and the condition of the animal, including mammals and humans. Exemplary amounts range from 1 ng/kg/day to 20 g/kg/day, such as 50 µg/kg/day to 5 g/kg/day or 0.5 to 50 mg/kg/day. The effective amount of compound is most effective in treating or preventing the condition when administered for periods ranging from about 1 to 1000 days or longer, such as from 7 to 300 days or from 30 to 90 days. The effective amount of compound may be continued beyond these periods for maintenance of beneficial responses in chronic diseases.

When the effective amount of the compound of the present invention is administered in a nutritional, therapeutic, medical, or veterinary composition, an exemplary dose ranges from about 0.001 to 10.0% wt/wt to the food or nutraceutical product.

When practiced, the methods of the invention can be by way of administering the compounds to a subject via any acceptable administration route using any acceptable form, as is described above, and allowing the body of the subject to distribute the compounds to the target tissues and cells through natural processes. As is described above, administering can likewise be by direct injection to a site (e.g., organ, tissue) containing a target cell (i.e., a cell to be treated).

The amount to be administered will vary depending on the subject, stage of disease or disorder, age of the subject, general health of the subject, and various other parameters known and routinely taken into consideration by those of skill in the medical arts. As a general matter, a sufficient amount of compound will be administered in order to make a detectable change in the amount of inflammation systemically or in any particular tissue or site in the body. Reduction of inflammation may be related to amount of pain experienced by the subject, insulin, anti-nuclear antigen antibodies, TNFα, or C-reactive protein levels in the blood, the percent of regulatory T-cells in the blood, or concentration of calprotectin in feces.

The methods of the present invention can provide treatments for reducing inflammation by affecting the metabolism of immune cells. The methods can reduce inflammation systemically (i.e., throughout the subject's body) or locally (e.g., at the site of administration or the site of inflammatory cells, including but not limited to T cells and macrophages). In treating or preventing inflammation through immunometabolism, one effect that may be observed is a shift in the metabolism of glucose. In particular, the shift may be from the production of lactate from pyruvate towards the entrance into the tricarboxylic acid cycle that is tied with immunoinflammatory actions. More specifically, this shift in metabolism can be associated with an increase in the proportion of CD4+CD25+FOXP3+ or other regulatory CD4+ T-cells relative to effector CD4+ T-cells such as IL17+ Th17 or IFNγ+ Th1 effector cells. Another observed effect may be decreased cellular proliferation resulting from the combination of decreased anaerobic metabolism and increased immune checkpoint pathways. Another effect of shifts in metabolism triggered therapeutically may be decreased expression of inflammatory chemokines such as MCP-1, IL-8, or CXCL9 resulting from altered processing and storage of fatty acids. The methods can thus also be considered methods of affecting or altering the immune response of a subject to whom the therapy is administered, thereby intercepting inflammation, disease, and pathology.

The methods of the present invention can provide methods of reducing inflammation. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood monocytes or macrophages and lymphocytes infiltrating a given tissue. Another may be the increase in regulatory immune cell populations, such as $CD4^+CD25^+FoxP3^+$ regulatory T-cells, or an increase in regulatory properties of lymphocytes or macrophages (e.g. increased interleukin 4 (IL-4) or IL-10 or decreased TNF-α and IL-6). Another may be the decreased presence of inflammatory genes and/or adhesion molecules. The methods can thus also be considered methods of affecting or altering the immune response of a subject to whom the therapy is administered. The subject may have any condition in which the immunomodulation of T cells or downregulation of cellular adhesion molecules is a desired outcome.

The invention provides methods of treating inflammatory or immune-mediated disease. The inflammatory or immune-mediated disease can include any disease described in Dattatreya et al. 2011 (Dattatreya et al., A Brief Review on Immune Mediated Diseases. *J Clin Cell Immunol* 2011, S11. DOI: 10.4172/2155-9899.S11-001 ISSN:2155-9899 JCCI) and Shurin et al. 2007 (Shurin M R, Smolkin Y S. Immune-mediated diseases: where do we stand? Adv Exp Med Biol. 2007; 601:3-12.), among others.

The invention provides methods of treating inflammatory diseases with the compounds described herein. The inflammatory diseases can comprise chronic inflammatory diseases. Non-limiting examples of chronic inflammatory diseases includes metabolic syndrome, obesity, prediabetes, cardiovascular disease, type 2 diabetes, nonalcoholic fatty liver disease, nonalcoholic steatohepatitis, cirrhosis, asthma, allergies, chronic granulomatous disease, graft versus host disease, and tumor necrosis factor receptor associated periodic syndrome; muscle wasting, such as amyotrophic lateral sclerosis, Duchenne muscular dystrophy, scoliosis, and progressive muscular atrophy; and others.

The invention provides methods of treating other inflammatory diseases such as acute colonic diverticulitis and radiation-induced inflammation of the gastrointestinal tract with the compounds described herein. Non-limiting examples of radiation-induced inflammation of the gastrointestinal tract include radiation proctitis, radiation enteritis, and radiation proctosigmoiditis.

The invention provides methods of treating chronic and/or inflammatory respiratory diseases. Non-limiting examples of chronic and/or inflammatory respiratory diseases include chronic obstructive pulmonary disease and idiopathic pulmonary fibrosis.

The invention provides methods of treating inflammatory conditions of the liver. Non-limiting examples of inflammatory conditions of the liver include nonalcoholic fatty liver disease, nonalcoholic steatohepatitis, and cirrhosis.

The invention provides methods of treating inflammatory conditions of the bile duct. Non-limiting examples of inflammatory conditions of the bile duct include primary biliary cholangitis and primary sclerosing cholangitis.

The invention provides methods of inhibiting inflammation in the GI tract, wherein relevant components of the GI tract can include the stomach, small intestine, large intestine, and rectum.

The invention provides methods of treating chronic and/or inflammatory central nervous diseases. Non-limiting examples of chronic and/or inflammatory central nervous diseases include Alzheimer's disease, Parkinson's disease, neuroinflammation resulting from stroke, traumatic brain injury, or spinal cord injury.

The invention provides methods of treating autoimmune diseases, such as inflammatory autoimmune diseases, with the compounds described herein. Non-limiting examples of autoimmune diseases include inflammatory bowel disease (IBD) (e.g., Crohn's disease and ulcerative colitis), irritable bowel syndrome (IBS), lupus, rheumatoid arthritis, Sjogren's syndrome, systemic scleroderma, type 1 diabetes, psoriasis, autoimmune encephalitis, multiple sclerosis, sarcoidosis, Guillain-Barre syndrome, Grave's disease, antiphospholipid syndrome and cancer-immunotherapy-induced autoimmune diseases, among others. Non-limiting examples of cancer-immunotherapy-induced autoimmune diseases include cancer immunotherapy-induced rheumatic diseases. Non-limiting examples of multiple sclerosis include relapsing-remitting multiple sclerosis, secondary progressive multiple sclerosis, and primary progressive multiple sclerosis. Non-limiting examples of lupus include systemic lupus erythematosus, lupus nephritis, and cutaneous lupus. Systemic lupus erythematosus is an autoimmune disease in which the immune system reacts to nuclear antigens and forms immune complexes that can aggregate or cause damage to multiple organ systems including skin, joints, kidneys, brain, the heart and cardiovascular systems and other organs. The invention also provides methods of treating inflammation associated with autoimmune diseases.

The compounds of the invention can be used to treat or ameliorate the complications arising from type 1 diabetes or other autoimmune diseases. Type 1 diabetes is an autoimmune disease characterized as a chronic condition in which the pancreas produces little to no insulin as a result of immunological destruction of insulin-producing beta cells within pancreatic islets. The insulin deficiency leads to chronic hyperglycemia that can cause organ damage, shortened lifespan, and reduced quality of life. The disease is also referred to as juvenile diabetes or insulin-dependent diabetes.

The invention provides methods of treating allergic diseases. Examples of allergic diseases include hay fever (seasonal allergies), sinusitis, asthma, eczema, hives, anaphylaxis.

The invention provides methods of treating metabolic diseases with the compounds described herein. Non-limiting examples of such metabolic diseases include hyperglycemia. Non-limiting examples of hyperglycemia include type 1 diabetes, type 2 diabetes, and prediabetes, and maturity onset diabetes of the young (MODY). Non-limiting examples of complications from hyperglycemia include diabetic nephropathy, diabetic retinopathy, chronic pain, diabetic neuropathy, diabetic kidney disease, deep vein thrombosis, and atherosclerosis.

The invention provides methods of treating an infectious disease with the compounds described herein. Non-limiting examples of such infectious diseases include viral infections, bacterial infections, and fungal infections.

Non-limiting examples of viral infections include infections from viruses in the family adenoviridae, such as adenovirus; viruses in the family herpesviridae such as herpes simplex, type 1, herpes simplex, type 2, varicella-zoster virus, epstein-barr virus, human cytomegalovirus, human herpesvirus, and type 8; viruses in the family papillomaviridae such as human papillomavirus; viruses in the family polyomaviridae such as BK virus and JC virus; viruses in the family poxviridae such as smallpox; viruses in the family hepadnaviridae such as hepatitis B virus; viruses in the family parvoviridae such as human bocavirus and parvovirus B19; viruses in the family astroviridae such as human astrovirus; viruses in the family caliciviridae such as norwalk virus; viruses in the family picornaviridae such as coxsackievirus, hepatitis A virus, poliovirus, and rhinovirus; viruses in the family coronaviridae such as acute respiratory syndrome virus; viruses in the family flaviviridae such as hepatitis C virus, yellow fever virus, dengue virus, and West Nile virus, viruses in the family togaviridae such as rubella virus; viruses in the family hepeviridae such as hepatitis E virus; viruses in the family retroviridae such as human immunodeficiency virus (HIV); viruses in the family orthomyxoviridae such as influenza virus; viruses in the family arenaviridae such as guanarito virus, junin virus, lassa virus, machupo virus, and sabia virus; viruses in the family bunyaviridae such as Crimean-Congo hemorrhagic fever virus; viruses in the family filoviridae such as ebola virus and marburg virus; coronavirus (COVID-19); viruses in the family paramyxoviridae such as measles virus, mumps virus, parainfluenza virus, respiratory syncytial virus, human metapneumovirus, hendra virus, and nipah virus; viruses in the family rhabdoviridae such as rabies virus; unassigned viruses such as hepatitis D virus; and viruses in the family reoviridae such as rotavirus, orbivirus, coltivirus, and banna virus, among others.

Non-limiting examples of bacterial infections include infections with the bacteria described above, in addition to *Bacillus anthracis, Bacillus cereus, Bordetella pertussis, Borrelia burgdorferi, Brucella abortus, Brucella canis, Brucella melitensis, Brucella suis Campylobacter jejuni Chlamydia pneumoniae, Chlamydia trachomatis, Chlamydophila psittaci, Clostridium botulinum, Clostridium difficile, Clostridium perfringens, Clostridium tetani, Corynebacterium diphtherias, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Yersinia pestis, Yersinia enterocolitica, Yersinia pseudotuberculosis*, and other species from the genera of the above-mentioned organisms.

Non-limiting examples of fungal infections include infection with fungi of the genus *Aspergillus*, such as *Aspergillus fumigatus*, which cause aspergillosis; fungi of the genus *Blastomyces*, such as *Blastomyces dermatitidis*, which cause blastomycosis; fungi of the genus *Candida*, such as *Candida albicans*, which cause candidiasis; fungi of the genus *Coccidioides*, which cause coccidioidomycosis (valley fever); fungi of the genus *Cryptococcus*, such as *Cryptococcus neoformans* and *Cryptococcus gattii*, which cause cryptococcosis; dermatophytes fungi, which cause ringworm; fungi that cause fungal keratitis, such as *Fusarium* species, *Aspergillus* species, and *Candida* species; fungi of the genus *Histoplasma*, such as *Histoplasma capsulatum*, which cause histoplasmosis; fungi of the order Mucorales, which cause mucormycosis; fungi of the genus *Saccharomyces*, such as *Saccharomyces cerevisiae*; fungi of the genus *Pneumocystis*, such as *Pneumocystis jirovecii*, which cause pneumocystis pneumonia; and fungi of the genus *Sporothrix*, such as *Sporothrix schenckii*, which cause sporotrichosis.

The invention also provides methods of treating cancer with the compounds described herein. Non-limiting examples of such cancers include colorectal cancer, familial adenomatous polyposis (PAP), throat cancer, thyroid cancer, gastric cancer, cancers of the gastrointestinal tract, pancreatic cancer, Hodgkin lymphoma, non-Hodgkin lymphoma, acute myeloid leukemia, hepatocellular cancer, gastrointestinal stromal tumors, acute lymphoblastic leukemia, chronic myeloproliferative disorders, hypereosinophilic syndrome, mastocytosis, among others.

The depiction or definition of any moiety or compound provided herein encompasses any tautomer of the moiety or compound, unless the context clearly dictates otherwise.

The depiction or definition of any moiety or compound provided herein encompasses any salt of the moiety or compound, unless the context clearly dictates otherwise.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Molecular Modeling

Example 1

Molecular Modeling of LANCL Ligands

Using previously described ligands of LANCL2, including abscisic acid, we determined the existence of a high affinity binding site in LANCL2. We identified a binding pocket with similar biochemistry in the structure of LANCL3. Using the shape, residues and polarity of these binding pockets, we developed a novel scaffold. Derivatives of this scaffold were then docked in silico to the LANCL2 and LANCL3 structures.

Methods

Virtual Screening. To provide additional insights into preliminary scaffolds, ligand databases were docked onto LANCL2 and LANCL3 using AutoDock Vina at each of the two sites using cuboid search grid of size (58×40×40 angstrom) to provide predicted binding affinities and conformations of ligands. Binding affinity was normalized to molecular weight of the ligand. Top ligands were selected for further examination of binding pose.

Compound generation. From the identified residues and predicted biochemical interactions, structures were generated for high affinity LANCL ligands. In silico medicinal chemistry approaches were utilized to generate a library of derivatives. Structure files were generated in .pdbqt format.

Analysis. Compounds were preliminarily ranked by lowest predicted binding affinity normalized to molecular weight representing the most favorable binding pose through a minimization of total intermolecular energy, total internal energy and torsional free energy. Compounds were then prioritized based on favorable distances to critical binding residues on LANCL2 and LANCL3.

Results

From the virtual screening and optimization of new chemical entities (NCEs), the highest affinity LANCL-binding NCEs were largely comprised of compounds with a terminal cinnoline ring system. In general, binding affinities were observed to be increased in compounds that contained lipophilic substituents at $A^3$, nonpolar substituents at $A^{13}$ or $A^{24}$, and/or polar substituents at $A_{10}$ or $A_{21}$. The binding affinities of selected family members are provided in FIGS. 1A, 1B, 1C, 1D, 1E, 1F, 1G, 1H, 1I, 1J, 1K, 1L, 1M, 1N, 1O, 1P, 1Q, and 1R. The predicted binding affinities in the respective lowest energy binding configuration ranged from −8.0 kcal/mol to −10.5 kcal/mol. The highest binding compound in this class of NCEs was observed to be N-(5-(6-trifluoromethylcinnolin-4-yl) pyridin-3-yl)-2-hydroxy-2-(1H-imidazol-2-yl)-2-phenylacetamide, termed BT-108-15. Other compounds with similarly high affinity for both LANCL2 and LANCL3 included BT-108-1 (N-(5-(cinnolin-4-yl) pyridin-3-yl)-2-hydroxy-2-(1H-imidazol-2-yl)-2-phenylacetamide) and BT-108-12 (N-(5-(cinnolin-4-yl)pyridin-3-yl)-2-hydroxy-2-(1H-imidazol-2-yl)-2-(3-methoxyphenyl)acetamide). BT-108-2 (N-(5-(cinnolin-4-yl)-4-methylpyridin-3-yl)-2-hydroxy-2-(1H-imidazol-2-yl)-2-phenylacetamide) showed substantially increased predicted affinity for LANCL2 compared to LANCL3. In contrast, BT-108-16 (N-(5-(6-methoxycinnolin-4-yl) pyridin-3-yl)-2-hydroxy-2-(1H-imidazol-2-yl)-2-phenylacetamide) showed greater affinity for LANCL3 compared to LANCL2. In general, minimal differences were present between stereoisomers, although exceptions did exist. Based on binding results and predicted physicochemical properties compounds were selected from this class for synthesis.

Medicinal Chemistry

Example 2

BT-108-1

Figure 2A:
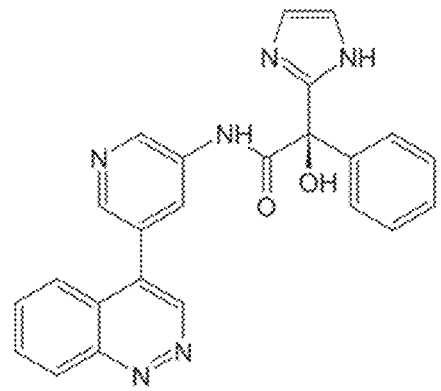
FIGS. 2A-2F. Exemplary compounds of the invention: BT-108-1 (FIG. 2A); BT-108-2 (FIG. 2B); BT-108-6 (FIG. 2C); BT-108-8 (FIG. 2D); BT-108-12 (FIG. 2E); BT-108-15 (FIG. 2F).

The synthesis of BT-108-1 (FIG. 2A) was a five step process as detailed below.

Bispinacolatodiboron and potassium acetate were charged to a stirred solution of 5-bromopyridin-3-amine in 1, 4-dioxane. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-aminopyridin-3-yl)boronic acid.

A stirred solution of 4-chlorocinnoline, 5-aminopyridin-3-yl)boronic acid and potassium carbonate in water/1,4-dioxane (8:2 V) was purged with nitrogen gas. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-(cinnolin-4-yl)pyridin-3-amine.

TEA was added to a solution of 5-(cinnolin-4-yl)pyridin-3-amine and 2-oxo-2-phenylacetic acid in THF at 0-5° C. The reaction mass was stirred followed by addition of T3P in ethyl acetate. After completion, the reaction mass was quenched with water and extracted with ethyl acetate to afford N-(5-(cinnolin-4-yl) pyridin-3-yl)-2-oxo-2-phenylacetamide.

p-Toluene sulfonic acid was added to a solution of 1H-imidazole in triethyl orthoformate and stirred at 130° C. Excess triethyl orthoformate was removed by vacuum distillation, followed by addition of sodium carbonate to afford 1-(diethoxymethyl)-1H-imidazole.

A stirred solution of 1-(diethoxymethyl)-1H-imidazole in THF was cooled to −60 to −65° C. n-BuLi in hexane was added to the solution and stirred at same temperature. N-(5-(cinnolin-4-yl) pyridin-3-yl)-2-oxo-2-phenylacetamide dissolved in THF was added to the solution and stirred at same temperature. Crude product was purified by reverse phase column chromatography followed by lyophilization overnight to afford N-(5-(cinnolin-4-yl) pyridin-3-yl)-2-hydroxy-2-(1H-imidazol-2-yl)-2-phenylacetamide.

1H NMR (401 MHz, DMSO): δ 12.03 (s, 1H), 11.12 (s, 1H), 9.41 (s, 1H), 9.12 (s, 1H), 8.59 (d, J=7.8 Hz, 2H), 8.47 (s, 1H), 8.03 (q, J=8.0 Hz, 2H), 7.94 (t, J=7.5 Hz, 1H), 7.57 (d, J=7.6 Hz, 2H), 7.33 (m, J=7.1 Hz, 4H), 7.02 (d, J=62.2 Hz, 2H).

Example 3

BT-108-2

Figure 2B:
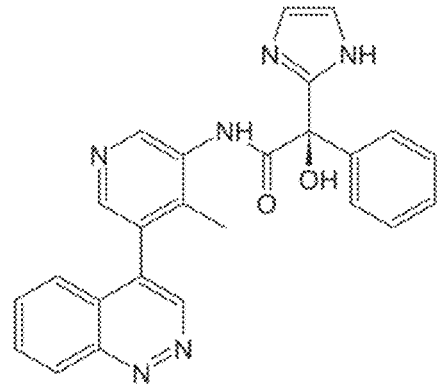

The synthesis of BT-108-2 (FIG. 2B) was a five step process as detailed below.

Bispinacolatodiboron and potassium acetate were charged to a stirred solution of 5-bromo-4-methylpyridin-3-amine in 1,4-dioxane. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford (4-methylpyridin-3-amine-5-yl)boronic acid.

A stirred solution of 4-chlorocinnoline, (4-methylpyridin-3-amine-5-yl)boronic acid and potassium carbonate in water/1,4-dioxane (8:2 V) was purged with nitrogen gas. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-(cinnolin-4-yl)-4-methylpyridin-3-amine.

TEA was added to a solution of 5-(cinnolin-4-yl)-4-methylpyridin-3-amine and 2-(1-benzylimidazol-2-yl)-2-oxoacetic acid in THF at 0-5° C. The reaction mass was stirred followed by addition of T3P in ethyl acetate. After completion, the reaction mass was quenched with water and extracted with ethyl acetate to afford N-(5-(cinnolin-4-yl)-4-methylpyridin-3-yl)-2-oxo-2-(1-benzylimidazol-2-yl)acetamide.

A stirred solution of bromophenylmagnesium in THF was cooled to −78° C. N-(5-(cinnolin-4-yl)-4-methylpyridin-3-yl)-2-oxo-2-(1-benzylimidazol-2-yl)acetamide dissolved in THF was added to the solution and heated to rt. After completion, the reaction mass was quenched and extracted with ethyl acetate to afford N-(5-(cinnolin-4-yl)-4-methylpyridin-3-yl)-2-hydroxy-2-(1-b enzylimidazol-2-yl)-2-phenylacetamide.

Palladium-charcoal under hydrogen was added to N-(5-(cinnolin-4-yl)-4-methylpyridin-3-yl)-2-hydroxy-2-(1-benzylimidazol-2-yl)-2-phenylacetamide at stirred at rt. After completion, the reaction mass was quenched and extracted with ethyl acetate. Crude product was purified by reverse phase column chromatography followed by lyophilization overnight to afford N-(5-(cinnolin-4-yl)-4-methylpyridin-3-yl)-2-hydroxy-2-(1H-imidazol-2-yl)-2-phenylacetamide.

Example 4

BT-108-6

Figure 2C:
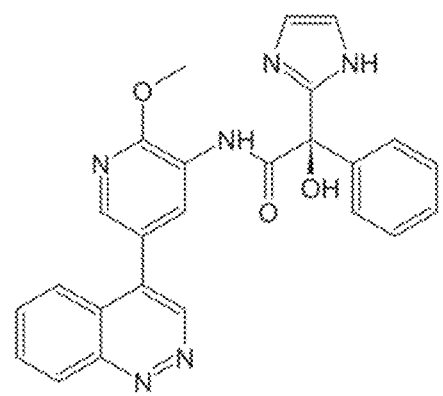

The synthesis of BT-108-6 (FIG. 2C) was a five step process as detailed below.

Bispinacolatodiboron and potassium acetate were charged to a stirred solution of 5-bromo-2-methoxypyridin-3-amine in 1, 4-dioxane. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford (2-methoxypyridin-3-amine-5-yl)boronic acid.

A stirred solution of 4-chlorocinnoline, (2-methoxypyridin-3-amine-5-yl)boronic acid and potassium carbonate in water/1,4-dioxane (8:2 V) was purged with nitrogen gas. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-(cinnolin-4-yl)-2-methoxypyridin-3-amine.

TEA was added to a solution of 5-(cinnolin-4-yl)-2-methoxypyridin-3-amine and 2-(1-benzylimidazol-2-yl)-2-oxoacetic acid in THF at 0-5° C. The reaction mass was stirred followed by addition of T3P in ethyl acetate. After completion, the reaction mass was quenched with water and extracted with ethyl acetate to afford N-(5-(cinnolin-4-yl)-2-methoxypyridin-3-yl)-2-oxo-2-(1-benzylimidazol-2-yl)acetamide.

A stirred solution of bromophenylmagnesium in THF was cooled to −78° C. N-(5-(cinnolin-4-yl)-2-methoxypyridin-3-yl)-2-oxo-2-(1-benzylimidazol-2-yl)acetamide dissolved in THF was added to the solution and heated to rt. After completion, the reaction mass was quenched and extracted with ethyl acetate to afford N-(5-(cinnolin-4-yl)-2-methoxypyridin-3-yl)-2-hydroxy-2-(1-benzylimidazol-2-yl)-2-phenylacetamide.

Palladium-charcoal under hydrogen was added to N-(5-(cinnolin-4-yl)-2-methoxypyridin-3-yl)-2-hydroxy-2-(1-benzylimidazol-2-yl)-2-phenylacetamide at stirred at rt. After completion, the reaction mass was quenched and extracted with ethyl acetate. Crude product was purified by reverse phase column chromatography followed by lyophilization overnight to afford N-(5-(cinnolin-4-yl)-2-methoxypyridin-3-yl)-2-hydroxy-2-(1H-imidazol-2-yl)-2-phenylacetamide.

Example 5

BT-108-8

Figure 2D:
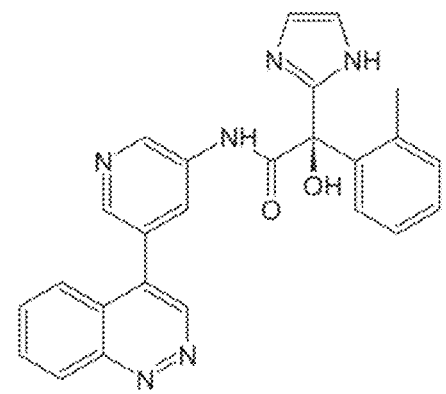

The synthesis of BT-108-8 (FIG. 2D) was a five step process as detailed below.

Bispinacolatodiboron and potassium acetate were charged to a stirred solution of 5-bromopyridin-3-amine in 1, 4-dioxane. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-aminopyridin-3-yl)boronic acid.

A stirred solution of 4-chlorocinnoline, 5-aminopyridin-3-yl)boronic acid and potassium carbonate in water/1,4-dioxane (8:2 V) was purged with nitrogen gas. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-(cinnolin-4-yl)pyridin-3-amine.

Oxalyl chloride and a catalytic amount of DMF was added to a solution of 2-oxo-2-(o-tolyl)acetic acid in DCM at 0-5° C. The reaction mass was stirred at rt. After completion, the reaction mass was evaporated completely under N2 atmosphere.

Sodium hydride was added to a solution of 5-(cinnolin-4-yl)pyridin-3-amine in THF at 0-5° C. and stirred at 0-5° C. The acid chloride product from the previous step was dissolved in THF and added to the reaction mass. The reaction mass was allowed to stir at rt. After completion, the reaction was quenched with water and extracted with ethyl acetate. Organic layer was dried over anhydrous sodium sulfate and concentrated under reduced pressure to afford N-(5-(cinnolin-4-yl)pyridin-3-yl)-2-oxo-2-(o-tolyl)acetamide.

A stirred solution of 1-(diethoxymethyl)-1H-imidazole in THF was cooled to −60 to −65° C. n-BuLi in hexane was added to the solution and stirred at same temperature. N-(5-(cinnolin-4-yl)pyridin-3-yl)-2-oxo-2-(o-tolyl)acetamide dissolved in THF was added to the solution and stirred at same temperature. Crude product was purified by reverse phase column chromatography followed by lyophilization overnight to afford N-(5-(cinnolin-4-yl)pyridin-3-yl)-2-hydroxy-2-(1H-imidazol-2-yl)-2-(o-tolyl)acetamide. 1H NMR (400 MHz, DMSO-d6): δ 11.86 (s, 1H), 10.69 (s, 1H), 9.42 (s, 1H), 9.15 (d, J=2.0 Hz, 1H), 8.62-8.55 (m, 2H), 8.48 (t, J=2.0 Hz, 1H), 8.06-8.00 (m, 2H), 7.98-7.90 (m, 1H), 7.25-7.05 (m, 4H), 6.98-6.90 (m, 2H), 6.86 (d, J=7.2 Hz, 1H), 2.18 (s, 3H).

Example 6

BT-108-12

Figure 2E:
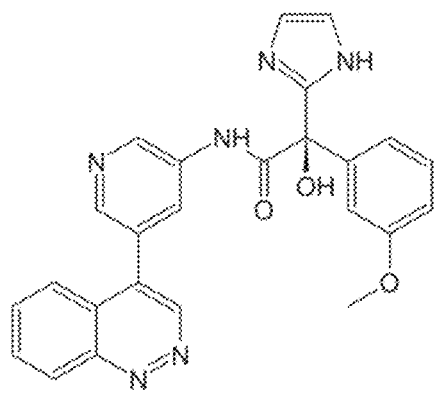

The synthesis of BT-108-12 (FIG. 2E) was a five step process as detailed below.

Bispinacolatodiboron and potassium acetate were charged to a stirred solution of 5-bromopyridin-3-amine in 1, 4-dioxane. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-aminopyridin-3-yl)boronic acid.

A stirred solution of 4-chlorocinnoline, 5-aminopyridin-3-yl)boronic acid and potassium carbonate in water/1,4-dioxane (8:2 V) was purged with nitrogen gas. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-(cinnolin-4-yl)pyridin-3-amine.

Oxalyl chloride and a catalytic amount of DMF was added to a solution of 2-(3-methoxyphenyl)-2-oxoacetic acid in DCM at 0-5° C. The reaction mass was stirred at rt. After completion, the reaction mass was evaporated completely under N2 atmosphere.

Sodium hydride was added to a solution of 5-(cinnolin-4-yl)pyridin-3-amine in THF at 0-5° C. and stirred at 0-5° C. The acid chloride product from the previous step was dissolved in THF and added to the reaction mass. The reaction mass was allowed to stir at rt. After completion, the reaction was quenched with water and extracted with ethyl acetate. Organic layer was dried over anhydrous sodium sulfate and concentrated under reduced pressure to afford N-(5-(cinnolin-4-yl)pyridin-3-yl)-2-(3-methoxyphenyl)-2-oxoacetamide.

A stirred solution of 1-(diethoxymethyl)-1H-imidazole in THF was cooled to −60 to −65° C. n-BuLi in hexane was added to the solution and stirred at same temperature. N-(5-(cinnolin-4-yl)pyridin-3-yl)-2-(3-methoxyphenyl)-2-oxoacetamide dissolved in THF was added to the solution and stirred at same temperature. Crude product was purified by reverse phase column chromatography followed by lyophilization overnight to afford N-(5-(cinnolin-4-yl)pyridin-3-yl)-2-hydroxy-2-(1H-imidazol-2-yl)-2-(3-methoxyphenyl)acetamide. 1H NMR (400 MHz, DMSO-d6): δ 12.02 (s, 1H), 11.13 (s, 1H), 9.41 (s, 1H), 9.12 (d, J=1.6 Hz, 1H), 8.62-8.58 (m, 2H), 8.46 (s, 1H), 8.08-8.00 (m, 2H), 7.98-7.90 (m, 1H), 7.35-7.20 (m, 2H), 7.20-6.90 (m, 4H), 6.90-6.85 (m, 1H), 3.72 (s, 3H).

Example 7

BT-108-15

Figure 2F:
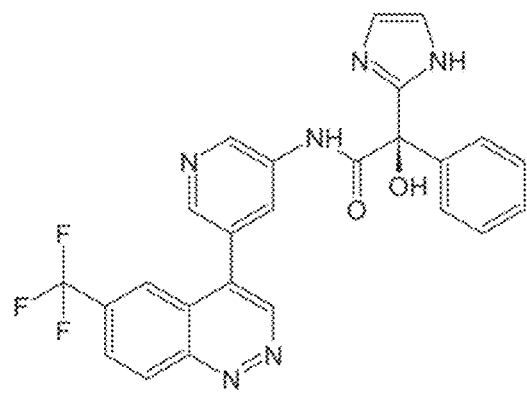

The synthesis of BT-108-15 (FIG. 2F) was a four step process as detailed below.

Bispinacolatodiboron and potassium acetate were charged to a stirred solution of 5-bromopyridin-3-amine in 1, 4-dioxane. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-aminopyridin-3-yl)boronic acid.

A stirred solution of 4-chloro-6-(trifluoromethyl)cinnoline, 5-aminopyridin-3-yl)boronic acid and potassium carbonate in water/1,4-dioxane (8:2 V) was purged with nitrogen gas. After adding PdCl2(dppf), the reaction mixture was purged with nitrogen gas. The reaction mass was heated to 80° C. After completion of reaction, mixture was cooled to 25° C.-30° C., filtered through celite bed and washed with ethyl acetate to afford 5-(6-trifluoromethylcinnolin-4-yl)pyridin-3-amine.

TEA was added to a solution of 5-(6-trifluoromethylcinnolin-4-yl)pyridin-3-amine and 2-oxo-2-phenylacetic acid in THF at 0-5° C. The reaction mass was stirred followed by addition of T3P in ethyl acetate. After completion, the reaction mass was quenched with water and extracted with ethyl acetate to afford N-(5-(6-trifluoromethylcinnolin-4-yl)pyridin-3-yl)-2-oxo-2-phenylacetamide.

A stirred solution of 1-(diethoxymethyl)-1H-imidazole in THF was cooled to −60 to −65° C. n-BuLi in hexane was added to the solution and stirred at same temperature. N-(5-(6-trifluoromethylcinnolin-4-yl) pyridin-3-yl)-2-oxo-2-phenylacetamide dissolved in THF was added to the solution and stirred at same temperature. Crude product was purified by reverse phase column chromatography followed by lyophilization overnight to afford N-(5-(6-trifluoromethylcinnolin-4-yl)pyridin-3-yl)-2-hydroxy-2-(1H-imidazol-2-yl)-2-phenylacetamide.

Experimental Studies

Example 8

Immunological Evaluation of LANCL3 In Vitro in CD4+ T Cells Introduction

CD4+ T cells are central to the pathogenesis of many autoimmune diseases and the amplification of inflammatory responses that can contribute to organ damage. As such, the trafficking and differentiation of these cells is an effective option for the amelioration of symptoms and prevention of flares in autoimmune disease.

Methods

Cell culture. Spleens were excised from wild-type and LANCL3−/− C57BL/6 mice. Spleens were crushed between the frosted ends of microscope slides and filtered to provide a cellular suspension. Red blood cells were lysed through hypotonic lysis. Remaining cells were washed and filtered. CD4+ T cells were enriched within the suspension using magnetic sorting based negative selection. For 6 hours, cells were stimulated with phorbol 12-myristate-13-acetate (PMA) and ionomycin.

Immunological analysis. Cells were collected from 96 well plates and stained with a cocktail of antibodies for immunophenotyping by flow cytometry. Data was captured on a BD FACS Celesta and analyzed using FACSDiva.

Results

Figure 3A:
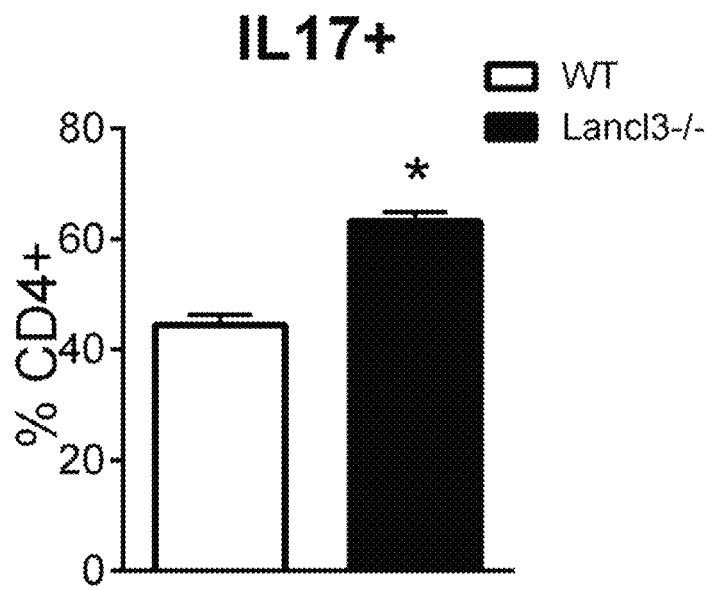
FIGS. 3A and 3B. Immunological evaluation of loss of LANCL3 in CD4+ T cells. Percentages of IL17+ (FIG. 3A) and FOXP3+ (FIG. 3B) CD4+ T cells were measured by flow cytometry after in vitro stimulation of wild-type and LANCL3−/− cells with PMA/I. Statistical significance (P<0.05) is marked by asterisks.
Figure 3B:
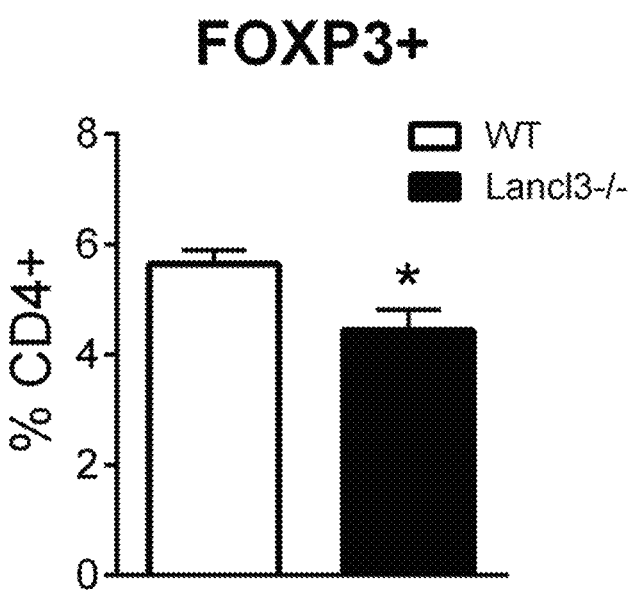

Increased proportions of IL17+ CD4+ T cells and decreased proportions of FOXP3+ CD4+ T cells were observed in samples from LANCL3−/− mice when compared to wild-type mice (FIGS. 3A and 3B), suggesting a bias for inflammatory subsets with the loss of LANCL3.

Example 9

Immunometabolic Evaluation of LANCL3 In Vitro in Bone Marrow Derived Dendritic Cells (BMDC) and Bone Marrow Derived Macrophages (BMDM)

Introduction

As a critical cell type in the innate immune response, macrophages and dendritic cells have a diverse spectrum of functions as both tissue resident cells and cells recruited to sites of inflammation from the blood. In both sites of inflammation and germinal centers, dendritic cells are key cell type involved in the processing and presentation of antigens. Based on their polarization, dendritic cells and macrophages can serve as phagocytes, activators of other immune cells, and resolvers of inflammation, among other functions. The immune functions of LANCL3 are unknown in dendritic cells and macrophages.

Methods

Cell culture. Bone marrow was flushed from the femur and tibia of wild-type and LANCL3−/− C57BL/6 mice. Bone marrow was then resuspended and filtered to provide a cellular suspension. Red blood cells were lysed through hypotonic lysis. Remaining cells were washed and filtered. Isolated cells were incubated in the presence of GM-CSF for 7 days to differentiate cells into dendritic cells. Cells were harvested, plated within 96 well plates. Cells were treated with oligomycin and rotenone/antimycin A in accordance with the Real-Time ATP Rate assay and analyzed by extracellular flux analyzer for mitochondrial ATP production. Separately, wild-type and LANCL3−/− bone marrow was differentiated into macrophages by incubation with M-CSF. BMDM were plated in 96 well plates following harvesting and stimulated with LPS (100 ng/mL) for 6 h. Expression of TNF and IL10 was assessed by flow cytometry.

Results

Figure 4:
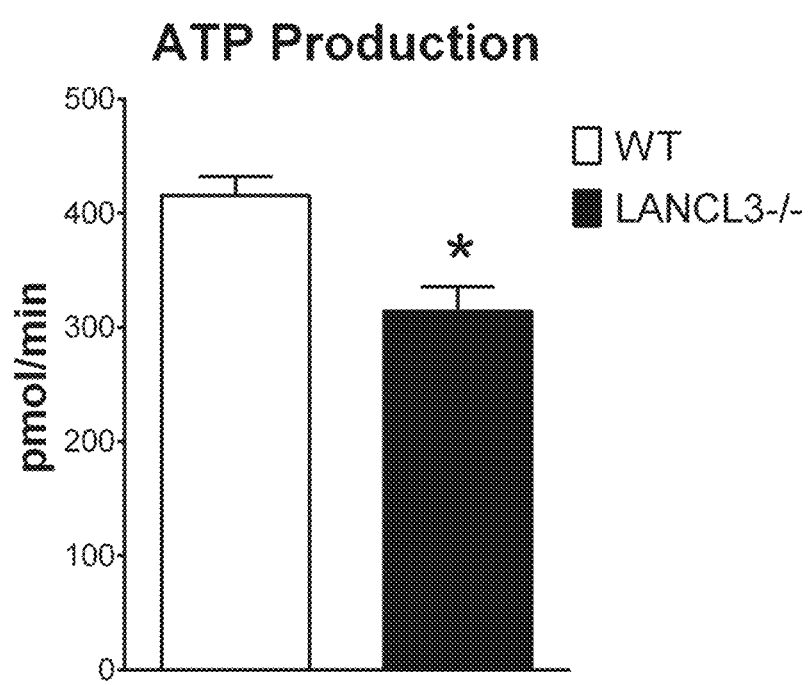
FIG. 4. Immunometabolic evaluation of loss of LANCL3 in bone marrow derived dendritic cells (BMDC). Mitochondrial ATP production rate in wild-type and LANCL3−/− BMDC. Statistical significance (P<0.05) is marked by asterisks.
Figure 5A:
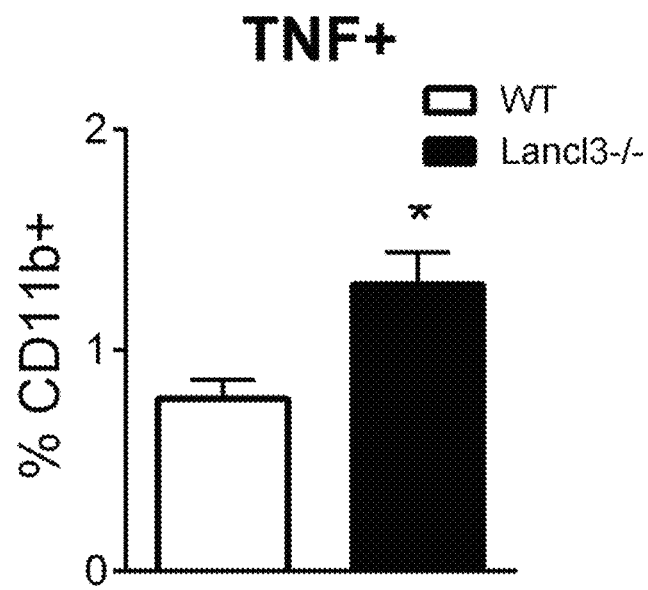
FIGS. 5A and 5B. Immunological evaluation of loss of LANCL3 in bone marrow derived macrophages (DMDM). Percentages of TNF+ and IL10+ cells by flow cytometry after in vitro stimulation of wild-type and LANCL3−/− cells with LPS. Statistical significance (P<0.05) is marked by asterisks.
Figure 5B:
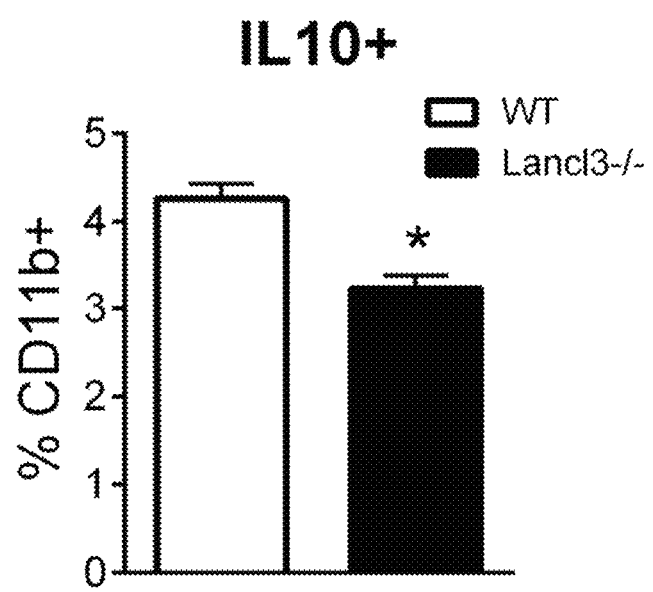

LANCL3−/− BMDC displayed a significantly lower rate of ATP production from the mitochondria in comparison to wild-type BMDC (FIG. 4). Increased TNF+ and decreased IL10+ BMDM were observed in LANCL3−/− samples following LPS stimulation in comparison to wild-type BMDM (FIGS. 5A and 5B).

Example 10

Loss of LANCL3 in an Acute Model of IBD

Introduction

Inflammatory bowel disease is a multifactorial disease with many disease processes initiated by actions or dysfunction of the epithelial barrier. A prominent and accepted animal model of the disease is induced by the administration of dextran sulfate sodium (DSS) in the drinking water of mice. Intake of DSS acts to disrupt and destroy the epithelial barrier in the distal gastrointestinal tract, in particular the colon. The disruption of the epithelial barrier allows for infiltration of the microbiome in the colonic mucosa and the ensuing recruitment and activation of immune cells, resulting in observed rectal inflammation and bleeding.

Methods

DSS model. Wild-type and C57BL/6 mice were given DSS in drinking water for seven days to induce disruption of the epithelial layer. At project initiation, mice were 8 weeks of age. Mice were scored daily for symptoms of disease (diarrhea, rectal bleeding, rectal inflammation, overall behavior).

Results

Figure 6:
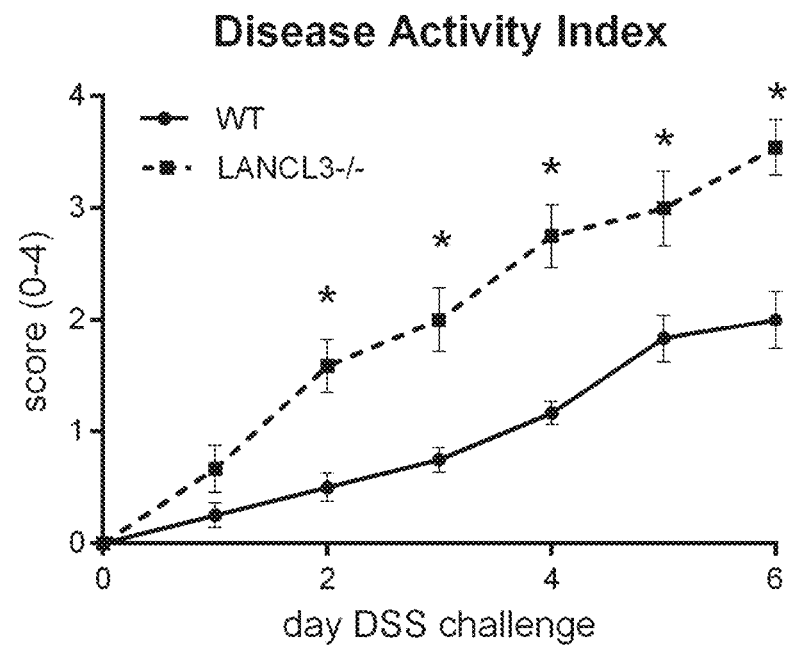
FIG. 6. Evaluation of loss of LANCL3 in a DSS model of colitis. Disease severity index over 7 days of DSS challenge in wild-type and LANCL3−/− mice. Statistical significance (P<0.05) is marked by asterisks.

LANCL3−/− mice were observed to present with significantly worsened disease when compared to wild-type (FIG. 6). In addition to higher peak disease, LANCL3−/− mice were quicker to develop rectal bleeding in comparison to wild-type.

Example 11

Loss of LANCL3 in a Model of Diet-Induced Obesity

Introduction

Obesity is a growing epidemic in the United States and worldwide. Resulting from poor diet and inactivity, obesity is a major cause of prediabetes and type 2 diabetes, which affect between 20 and 30% of the adult population. Paramount in these conditions is impaired glycemic control which can result from numerous factors including poor insulin sensitivity, decreased metabolic activity in muscle and systemic inflammation.

Methods

HFD-induced model. Wild-type and LANCL3−/− C57BL/6 mice were placed on a high fat diet with 60% of calories derived from fat for 12 weeks. Mice were fasted for 4 hours then given an oral dose of glucose (2 g/kg). Blood glucose levels were measured a 0, 15, 30, 60, 90, and 120 minutes post-glucose by glucometer.

Results

Figure 7:
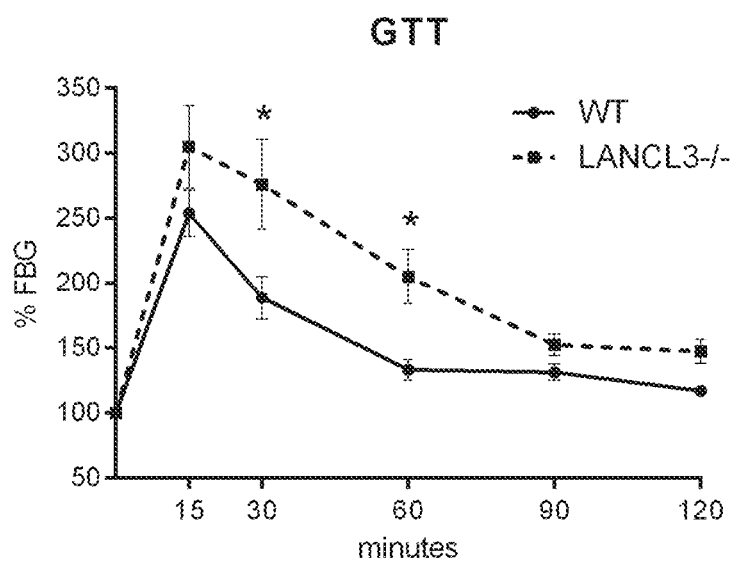
FIG. 7. Evaluation of loss of LANCL3 in a diet induced obesity model. Glucose tolerance test of wild-type and LANCL3−/− mice after 12 weeks of 60% kcal high-fat diet. Statistical significance (P<0.05) is marked by asterisks.

The loss of LANCL3 resulted in impaired glucose homeostasis (FIG. 7). LANCL3−/− mice experienced higher peak glucose levels and had a slower return to basal levels when compared to wild-type mice.

Example 12

Loss of LANCL3 in a Model of Experimental Autoimmune Encephalomyelitis

Introduction

MS afflicts over 700,000 people in the United States and 2.2 million worldwide. This widespread and debilitating illness results in decreased quality of life, with over 1.1 million DALYs, and significant healthcare related costs, over $28 billion yearly in the US. Despite advances and new therapies, no evidence of disease activity (NEDA) rates are 30-40%, yearly relapse rates for MS are still 30%, with only minimal effects on the progression of disease and time to disability. MS may result from deficiencies in both the immune and central nervous system which combine to result in the demyelination and damage to neurons.

Methods

Figure 8:
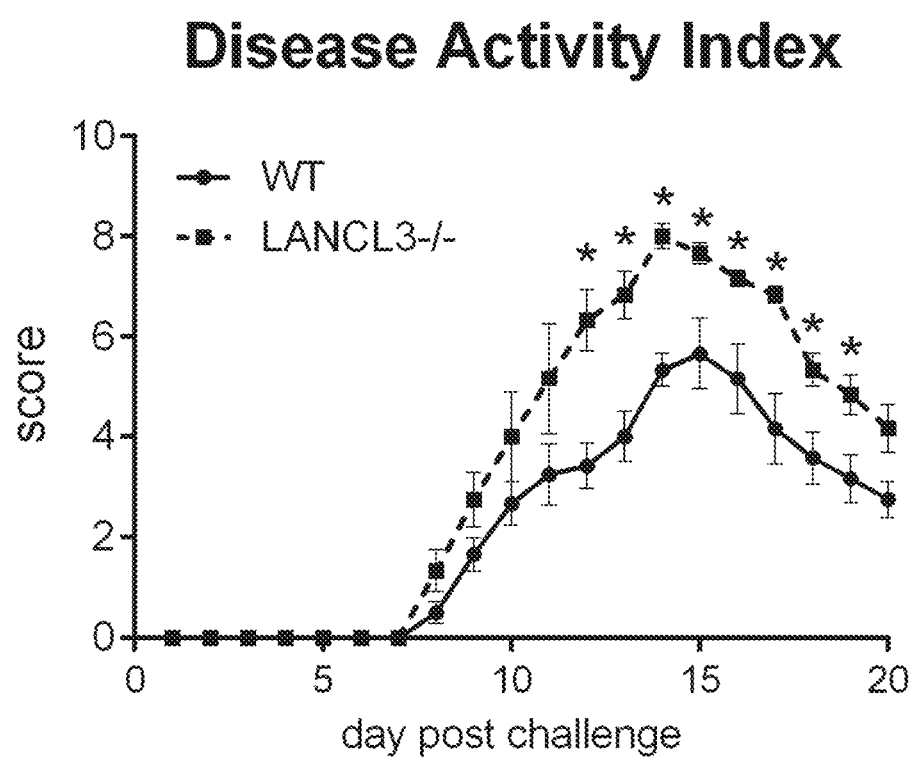
FIG. 8. Evaluation of loss of LANCL3 in an experimental autoimmune encephalomyelitis model. Disease severity index over 20 days post-immunization in wild-type and LANCL3−/− mice. Statistical significance (P<0.05) is marked by asterisks.

Mouse model. Wild-type and LANCL3−/− C57BL6 mice were challenged at 6- to 8-weeks of age with MOG immunization. Complete Freund's adjuvant (CFA) was prepared by suspension of heat-killed *Mycobacterium tuberculosis* (H37RA) at 10 mg/mL in incomplete Freund's adjuvant. MOG35-55 was resuspended in sterile nanopure water to a concentration of 2 mg/mL. CFA and MOG35-55 solution were emulsified in a 1:1 ratio using glass syringes and a near-closed three-way valve for 10 minutes. Emulsion was left to sit for 30 prior to immunization to ensure it is stable. Pertussis toxin was resuspended to a concentration of 2 µg/mL in PBS. MOG emulsion was administered to the left and right flank at 100 µL per site to each mouse. Pertussis toxin was administered by intraperitoneal injection (200 µL) on days 0 and 2 of the study to each mouse. Mice were scored (0-4) daily for disease activity (coordination, gait, paralysis).
Results
The loss of LANCL3 resulting in accelerated disease onset and greater peak disease severity by comparison of LANCL3−/− to WT (FIG. 8).

Example 13

Immunological Screening In Vitro in CD4+ T Cells

Figure 9A:
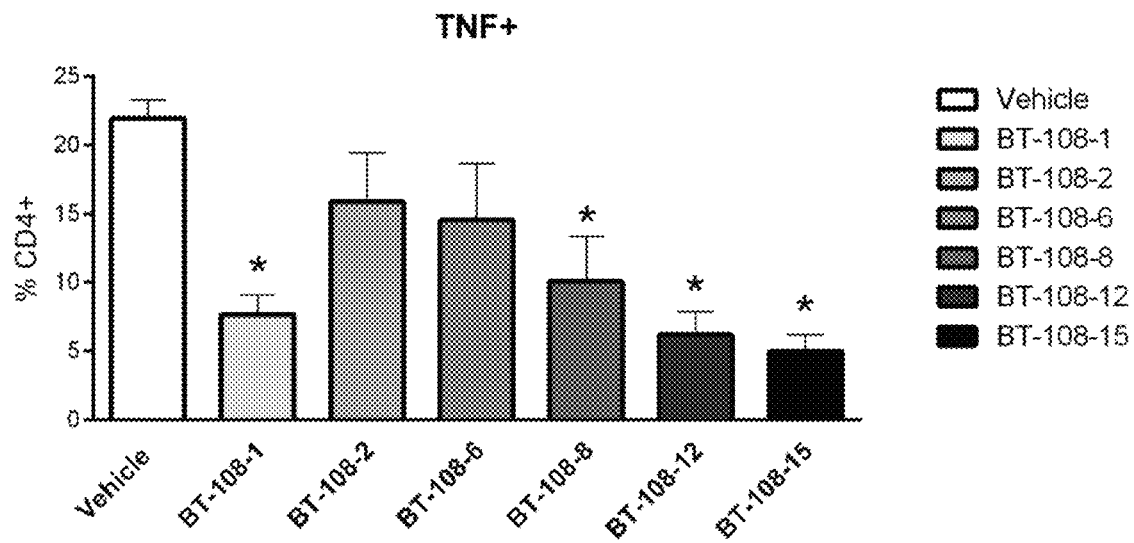
FIGS. 9A and 9B. Immunological validation of BT-108-1, BT-108-2, BT-108-6, BT-108-8, BT-108-12, and BT-108-15 activity in CD4+ T cells. Percentages of TNFα+ (FIG. 9A) and IFNγ+ (FIG. 9B) CD4+ T cells were measured by flow cytometry after in vitro treatment of cells with BT compounds at concentrations of 100 nanomolar. Statistical significance (P<0.05) is marked by asterisks.
Figure 9B:
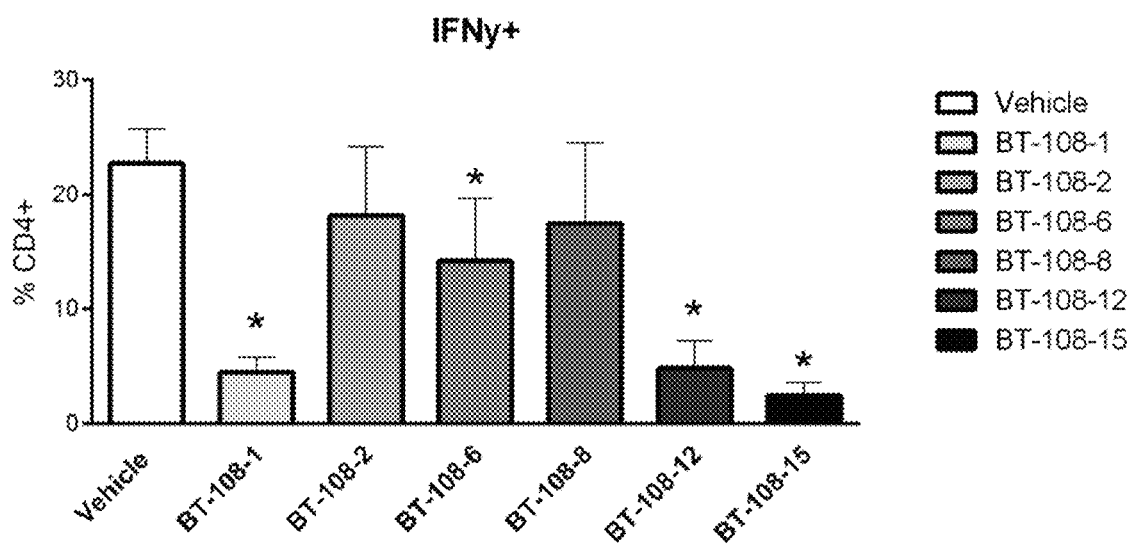

Introduction
CD4+ T cells are central to the pathogenesis of many autoimmune diseases and the amplification of inflammatory responses that can contribute to organ damage. As such, the trafficking and differentiation of these cells is an effective option for the amelioration of symptoms and prevention of flares in autoimmune disease. With the loss of LANCL3, CD4+ T cells produced greater amounts of inflammatory cytokines and have a higher likelihood of differentiating into effector subsets, such as Th17 and Th1.
Methods
Cell culture. Spleens were excised from C57BL/6 mice. Spleens were crushed between the frosted ends of microscope slides and filtered to provide a cellular suspension. Red blood cells were lysed through hypotonic lysis. Remaining cells were washed and filtered. CD4+ T cells were enriched within the suspension using magnetic sorting based negative selection. Cells were collected and plated within 96 well plates coated with anti-CD3/CD28 and cultured in the presence of BT-108-1, BT-108-2, BT-108-6, BT-108-8, BT-108-12, and BT-108-15 at 0 or 100 nanomolar for 24 h. During the last 6 h of culture, cells were stimulated with phorbol 12-myristate-13-acetate (PMA) and ionomycin.
Immunological analysis. Cells were collected from 96 well plates and stained with a cocktail of antibodies for immunophenotyping by flow cytometry. Culture supernatant was collected and assayed for cytokine concentrations by cytometric bead array. Data was captured on a BD FACS Celesta and analyzed using FACSDiva.
Results
The six tested LANCL ligands all decreased production of TNFα (FIG. 9A) and IFNγ (FIG. 9B) in CD4+ T cell culture. BT-108-1, BT-108-12, and BT-108-15 were observed to have the largest magnitude of response in TNF+ and IFNγ+ CD4+ T cells, providing a significant reduction at 100 nanomolar relative to vehicle control. Similar profiles were observed in both cytokines across the tested ligands.

Example 14

Figure 10A:
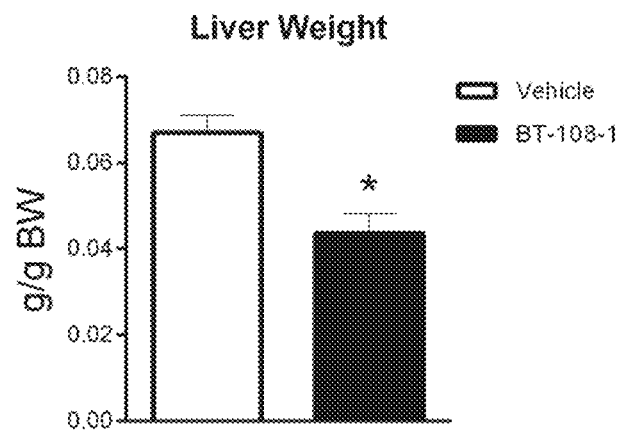
FIGS. 10A-10C. In vivo validation of BT-108-1 efficacy in a Western diet model of nonalcoholic steatohepatitis. Liver weight (FIG. 10A), fibrosis score (FIG. 10B) and liver triglycerides (FIG. 10C) after 12 weeks of Western diet with weekly carbon tetrachloride injections in vehicle and BT-108-1 (5 mg/kg) treated mice. Statistical significance (P<0.05) is marked by asterisks.
Figure 10B:
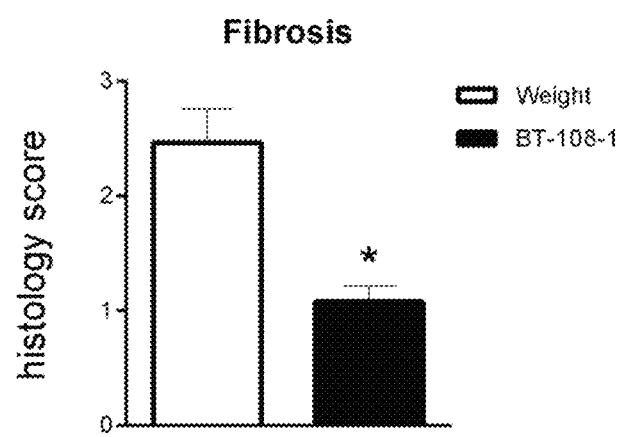
Figure 10C:
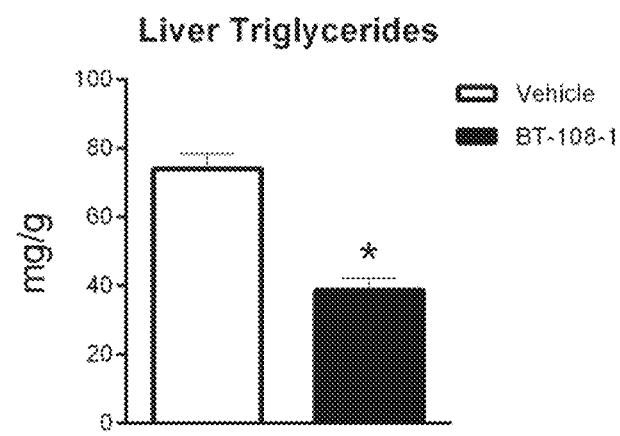

Use of BT-108-1 in a Model of Nonalcoholic Steatohepatitis and Diet-Induced Obesity Introduction
NASH is a progressive chronic liver disease that afflicts over 140 million people worldwide with total health care costs exceeding $8 billion annually in the US alone. No current therapeutics are approved for NASH. While a reversible condition, failure to effectively treat NASH results in higher risk of hepatocellular carcinoma, liver failure and cardiac death. With a multitude of hepatic and extrahepatic factors, NASH is a complex disease. Yet, many therapeutics in development fail to address all three main areas of dysregulation, comprised of metabolic, inflammatory, and fibrotic factors. NASH is a common comorbidity in obesity and type 2 diabetes. As such, many animal models use diet-induced obesity to result in glucose intolerance or impaired insulin sensitivity.
Methods
WD-induced model. C57BL/6 mice were placed on a Western diet consisting of a high-fat diet with addition of 23.1 g/L d-fructose and 18.9 g/L d-glucose to drinking water and weekly intraperitoneal injections of 0.2 µL/g CC14 to induce steatohepatitis [11]. Matching groups on control diet were included. Mice were treated daily, in a therapeutic manner after 8 weeks of diet. Treatment with BT-108-1 (5 mg/kg) or vehicle control occurred by oral gavage. Dosage was calculated based off mean body weights.
Analysis. Livers were excised and weighed. Sections of livers were excised and stored in buffered formalin for Sirius red staining or snap frozen for assessment of triglycerides. Severity of fibrosis was assessed by scoring of Sirius red stained liver.
Results
Oral BT-108-1 reduced body weight normalized liver weights (FIG. 10A), fibrotic scoring (FIG. 10B) and liver triglycerides (FIG. 10C) after 4 weeks of treatment, suggesting the potential to improve liver inflammation and fibrosis in the context of NASH.

Example 15

Use of BT-108-1 in a NOD Mouse Model of T1D

Figure 11A:
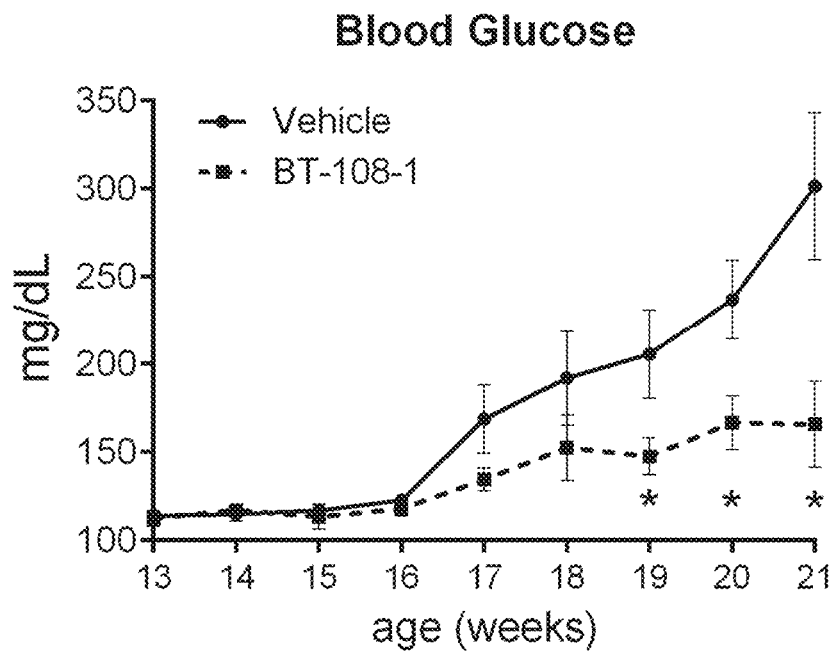
FIGS. 11A and 11B. In vivo validation of BT-108-1 efficacy in a NOD model of type 1 diabetes. Fasting blood glucose (FIG. 11A) and onset of hyperglycemia (FIG. 11B) in NOD mice treated with vehicle or BT-108-1 (10 mg/kg) by oral gavage daily. Statistical significance (P<0.05) is marked by asterisks.
Figure 11B:
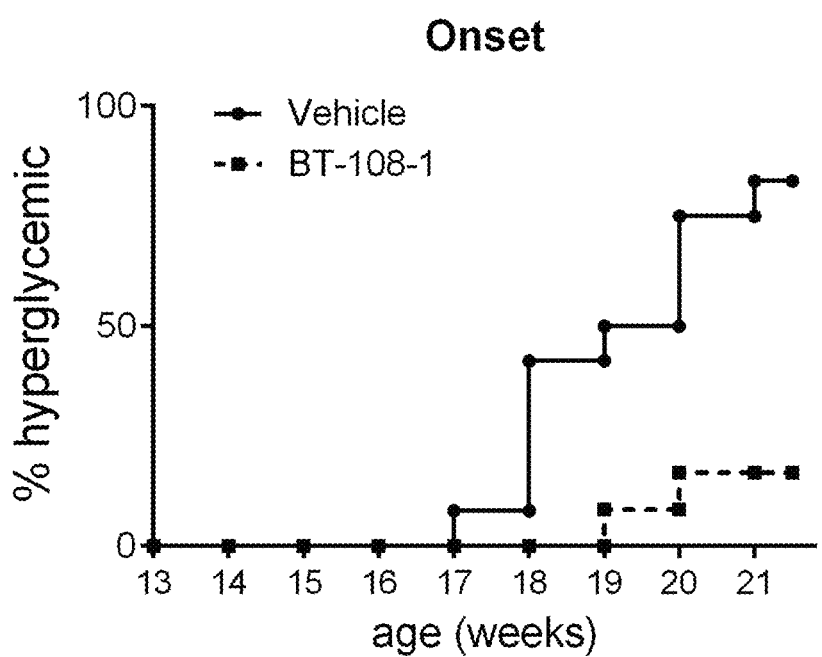

Introduction
Type 1 Diabetes (T1D) is an autoimmune disease in which the immune system destroys insulin-producing pancreatic cells necessitating life-long insulin therapy through injections or pumps. With current treatments, glycemic control is difficult resulting in prolonged periods of hyperglycemia and dysregulated glucose metabolism that contribute to organ damage and co-morbidities (blindness, kidney failure, cardiovascular disease, loss of extremities). Currently no treatments are approved for the prevention of disease progression at onset (i.e. restoring immunological tolerance to diabetes-associated antigens to allow regrowth of pancreatic beta cells) and very few are approved to assist in glycemic control. LANCL2 is a potent receptor that contributes to immune responses, cellular metabolism, and survival of cells. Based on observations in immunometabolic studies, parallel activation of LANCL3 may have an enhanced effect.
Methods
NOD model. Non-obese diabetic (NOD) ShiLt mice were used in this study. NOD mice have numerous genetic mutations that enable the spontaneous onset of hyperglycemia and pancreatic pathologies associated with T1D. Mice entered into the experiment at 9 weeks of age and were monitored for a 12-week period. Mice were treated daily with vehicle or 10 mg/kg BT-108-1 by oral gavage. Once weekly blood samples were collected from the tail vein to be tested for glucose concentration by glucometer.
Results
Oral BT-108-1 resulted in lower fasting blood glucose levels throughout the treatment period (FIG. 11A). Similarly, a lower proportion of mice treated with BT-108-1 developed hyperglycemia by the end of the study in comparison to vehicle treated controls (FIG. 11B).

Example 16

Use of BT-108-1 in a Mouse Model of Rheumatoid Arthritis

Introduction

Rheumatoid arthritis (RA) causes severe inflammation of joints leading to loss of mobility and intense pain. The underlying immunology of synovial inflammation is complex involving the interplay of myeloid cells, T cells, fibroblasts, and other structural cells of the synovium. High expression of TNF and IL-6 are central to the pathogenesis of RA, with additional contributions by IL-1β, IL-12, IL-17, IL-21, IL-23, MCP1, and TGF-β. Together these cytokines can lead to leukocytic recruitment, bone remodeling, pannus formation, oxidative stress and hyperplasia of the joint lining.

Methods

Models. Six-week-old C57Bl/6 mice were immunized with 200 μg of chicken collagen emulsified in complete Freund's adjuvant by intradermal injections at the base of the tail. Mice were treated with 5 mg/kg of BT-108-1 or vehicle, daily for four weeks.

Immunological analysis. Spleens were excised from mice. Tissues were crushed and filtered to provide a cellular suspension. Red blood cells were lysed. Cells were labeled with mixtures of extracellular (CD45, CD3, CD4, CD8, B220, CD19, CD138, CD21, CD24, CD1d, CD11b, CD86, CD80) and intracellular (BCL6, IL21, IL10, TNF) antibodies in a sequential live staining in 96-well plates in preparation for flow cytometry. Data was captured on a BD FACS Celesta and analyzed using FACSDiva.

Results

Figure 12A:
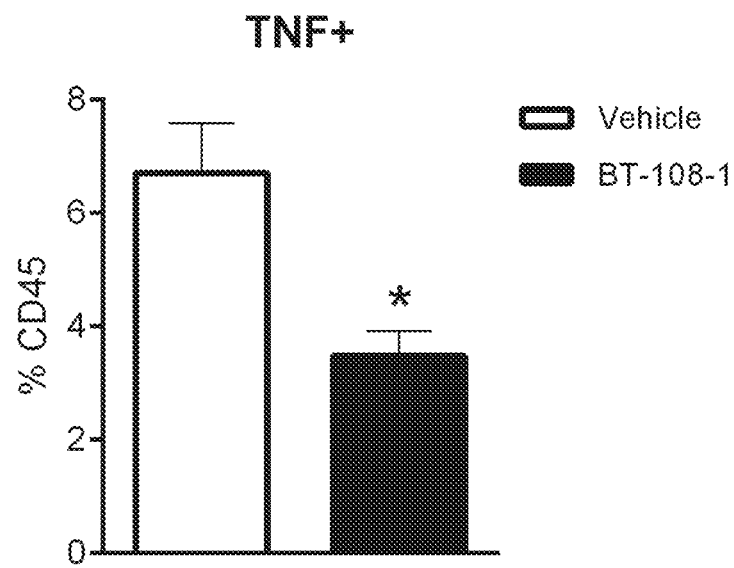
FIGS. 12A and 12B. In vivo validation of BT-108-1 efficacy in a collagen induced model of arthritis. Percentages of TNF+ (FIG. 12A) and IL17+ CD4+ T cells (FIG. 12B) in the spleens of collagen induced arthritis mice after 4 weeks of daily oral treatment with vehicle or BT-108-1 (5 mg/kg). Statistical significance (P<0.05) is marked by asterisks.
Figure 12B:
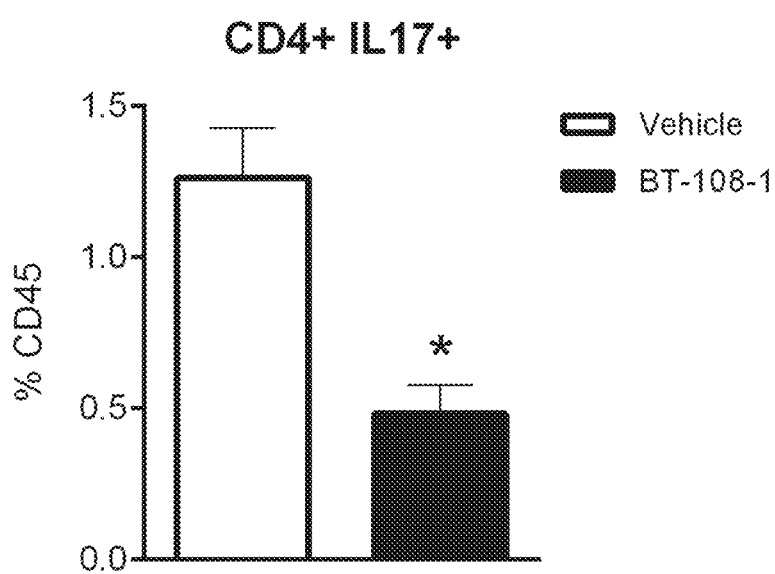

Oral BT-108-1 significantly reduced the proportion of TNF+ immune cells (FIG. 12A) and IL-17+ CD4+ T cells (FIG. 12B) in the spleens of mice with collagen induced arthritis in comparison to vehicle treated controls.

Example 17

Use of BT-108-1 in a Model of Psoriasis

Introduction

Psoriasis (PsO) afflicts over 7 million people in the United States and 15 million worldwide, with over 95 million worldwide afflicted by inflammatory skin diseases, inclusive of PsO, atopic dermatitis and rosacea. The resultant itchiness, effects on appearance, and persistent rashes have a significant impact on quality of life. In psoriasis, the most successful therapies have targeted Th17 cells and the IL-17/IL-23 axis. As such, demonstrating the ability of novel therapeutics to impact the differentiation of these cells, in vivo, is a critical mechanistic finding. Importantly, impacting Th17/Treg plasticity may indicate a mechanistic avenue for the maintenance of clinical responses by establishing a tolerogenic environment. Meanwhile Th17 cells are believed to be the most responsive to metabolic manipulation, suggesting a susceptibility to the immunometabolic effects of the LANCL pathways.

Methods

IMQ-induced model. C57BL/6 mice were anesthetized, shaved, and briefly exposed to depilatory cream on the surface of the back. Mice were given three days to recover from the procedure prior to entry to the study. After 3 days, mice were challenged with approximately 60 mg of 0.5% imiquimod cream daily by spreading cream over the shaved area. Mice were scored daily for erythema, scaling and skin thickness. Treatment with BT-108-1 (10 mg/kg) or vehicle control occurred by oral gavage. Dosage was calculated based off mean body weights.

Analysis. Spleens were excised and crushed by microscope slides. Red blood cells were hypotonically lysed from the resultant suspension. Samples were filtered, washed and centrifuged prior to staining. Th1 (Tbet+ IFNγ+), Th17 (RORγT+ IL17+), Treg (CD25+ FOXP3+ IL10+) and Tfh (BCL6+ IL21+) were quantified from CD3+ CD4+ T cells by flow cytometry.

Results

Figure 13A:
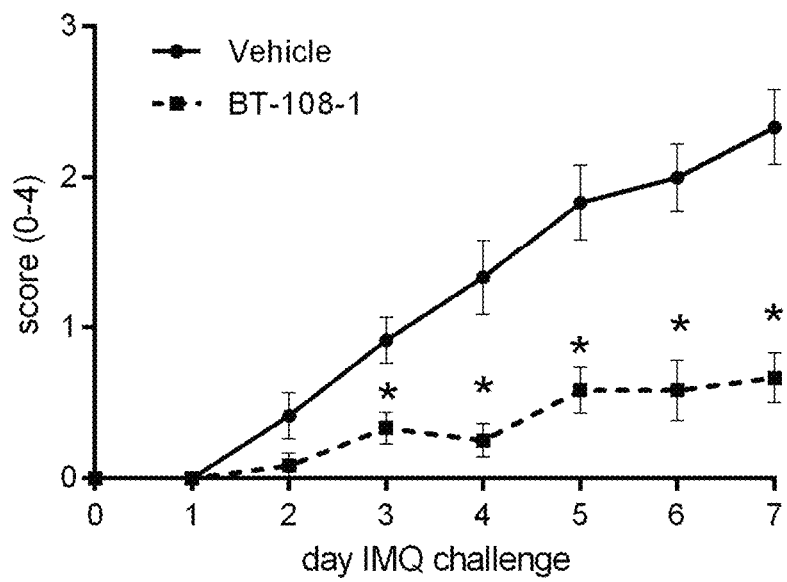
FIGS. 13A and 13B. In vivo validation of BT-108-1 efficacy in an imiquimod induced model of psoriasis. Composite scoring of skin (FIG. 13A) and percentage of CD4+ IL17+ cells in the spleen (FIG. 13B) of imiquimod-induced psoriasis mice after one week of daily oral treatment with vehicle or BT-108-1 (10 mg/kg). Statistical significance (P<0.05) is marked by asterisks.
Figure 13B:
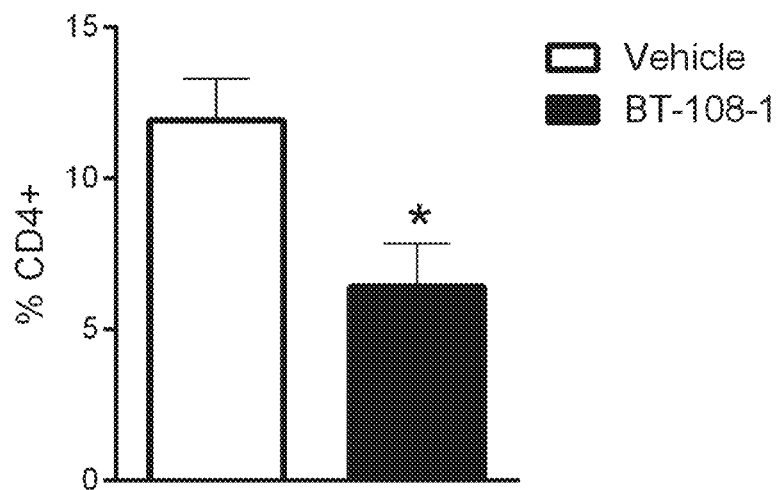

Oral BT-108-1 reduced severity of disease (FIG. 13A). Immunologically, BT-108-1 reduced Th17 cells in the spleen (FIG. 13B), suggesting the potential to improve psoriasis associated inflammation.

Example 18

Use of BT-108-1 in an Acute Model of IBD

Introduction

Inflammatory bowel disease is a multifactorial disease with many disease processes initiated by actions or dysfunction of the epithelial barrier [12]. A prominent and accepted animal model of the disease is induced by the administration of dextran sulfate sodium (DSS) in the drinking water of mice. Intake of DSS acts to disrupt and destroy the epithelial barrier in the distal gastrointestinal tract, in particular the colon. The disruption of the epithelial barrier allows for infiltration of the microbiome in the colonic mucosa and the ensuing recruitment and activation of immune cells. While CD4+ T cells are a major focus of development of therapeutics for IBD, recruitment of neutrophils in the intestinal lamina propria of IBD patients is one of the most predictive markers of response to treatment histologically. Loss of LANCL3 results in worsened disease severity.

Methods

DSS model. Mice were given DSS in drinking water for seven days to induce disruption of the epithelial layer. At project initiation, mice were 8 weeks of age and began dosing 24 hours after being placed on DSS. BT-108-1 was prepared within a 0.5% methylcellulose (12-15 cP) solution. Dosage used was 10 mg/kg delivered once daily. Dosage was calculated based off mean body weights for each gender. Oral dosage was delivered by orogastric gavage of dosage in 0.2 mL volume.

Flow Cytometry. Colons were collected into RPMI/FBS buffer containing collagenase (300 U/mL) and DNase (50 U/mL) for digestion. Tissues were digested for 60 minutes under stirring at 37° C. Resultant cellular suspensions were filtered through 100 μm strainers, centrifuged (300×g, 8 min), and washed in fresh RPMI. Following filtration of the resulting single cell suspensions, immune cells were purified by Percoll gradient of cell-containing 40% Percoll overlayed onto 70% Percoll solution. After centrifugation, interphase was collected and washed to obtain enriched colonic lamina propria cell fractions. Cells were labeled with mixtures of extracellular (CD45, CD3, CD4, CD8, CD19, NK1.1, F4/80, CD11b, Gr1) antibodies in a sequential live staining in 96-well plates. Data was acquired using a FACS Celesta flow cytometer with FACSDiva software.

Figure 14A:
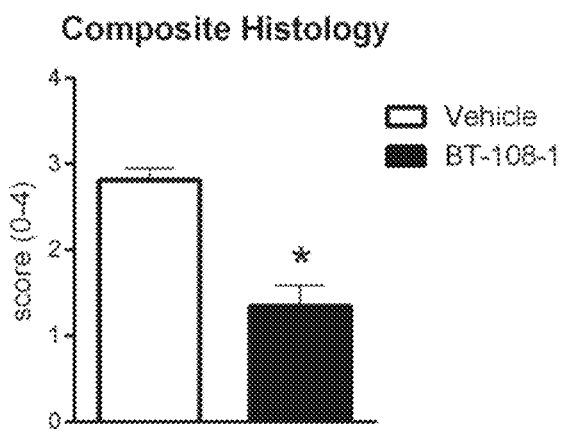
FIGS. 14A-14C. In vivo validation of BT-108-1 efficacy in a DSS model of colitis. Histological scores (FIG. 14A), and percentages of neutrophils (FIG. 14B) and CD4+ IL17+ T cells (FIG. 14C) in the colonic lamina propria after 7 days of DSS challenge in mice treated with vehicle or BT-108-1 (10 mg/kg) daily by oral gavage. Statistical significance (P<0.05) is marked by asterisks.
Figure 14B:
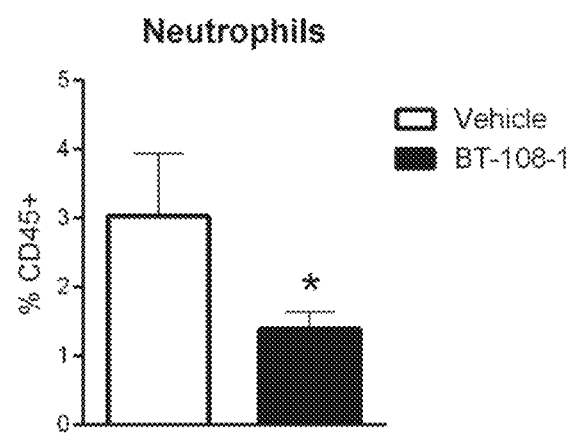
Figure 14C:
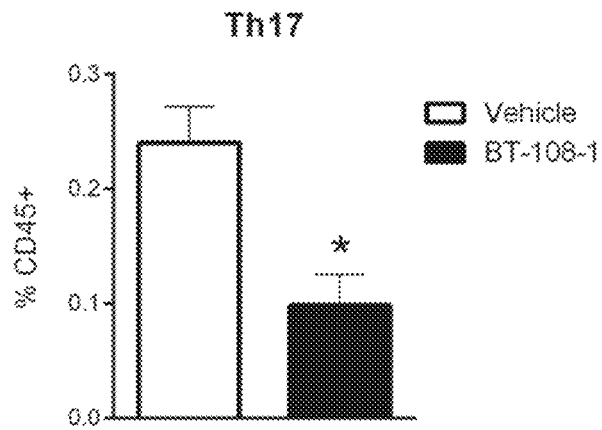

Histopathology. Colonic tissues were fixed in 10% formalin, paraffin embedded, and H&E stained. Sections were examined using an Olympus microscope. Histological score was assessed through a composite scoring system of leukocytic infiltration, epithelial erosion, and mucosal thickness.
Results Oral BT-108-1 treatment decreased the histopathology score in mice with DSS colitis relative to vehicle treated controls (FIG. 14A). Immunologically, BT-108-1 decreased the presence of neutrophils (FIG. 14B) and Th17 cells (FIG. 14C) in the colonic lamina propria.

Example 19

Use of BT-108-1 in a Genetic Mouse Model of SLE

Introduction

Systemic lupus erythematosus (SLE) is a systemic autoimmune disease that can cause damage to kidneys, cardiovasculature, and joints. SLE is a result of a complex interaction of genetic factors that results in immunological disease manifested primarily through a generation of autoantibodies. One preclinical model aimed at captured these complex factors is the NZB/W F1 model. The F1 cross of NZB and NZW mice results in mice with autoimmunity of progressive severity. This autoimmunity shares many common features with human SLE including the generation of anti-nuclear antibodies, kidney damage and elevated type I interferon responses.

Methods

NZB/W F1 model. Twenty-four-week-old, female NZB/W F1 mice will be randomized into vehicle or BT-108-1 treated arms based on baseline urine protein levels. BT-108-1 will be administered daily at 10 mg/kg for 12 weeks. Mice will be weighed on a weekly basis to update dosage formulation. Dosage will be calculated based off mean body weights.

Immunological analysis. Urine will be collected for assay for protein content to test for kidney function at baseline, 6, and 12 weeks of treatment. Spleens will be excised, crushed and filtered to provide a cellular suspension. Red blood cells will be lysed. Cells will be labeled with mixtures of extracellular and intracellular antibodies in a sequential live staining in 96-well plates in preparation for flow cytometry. Data was captured on a BD FACS Celesta and analyzed using FACSDiva.

Results

Oral BT-108-1 is expected to protect mice from the worsening of proteinuria grade. At 12 weeks of treatment, BT-108-1 treated mice would be expected to have a slight improvement of proteinuria relative to baseline on average. In comparison, vehicle treated mice would be expected to experience an approximate tripling of baseline levels. In the spleen, BT-108-1 treated mice would be expected to present with decreased proportions of CD4+ IL17+ and CD4+ IL21+ T cells relative to vehicle treated mice.

Example 20

Use of BT-108-1 in a Model of Experimental Autoimmune Encephalomyelitis

Introduction

MS afflicts over 700,000 people in the United States and 2.2 million worldwide. This widespread and debilitating illness results in decreased quality of life, with over 1.1 million DALYs, and significant healthcare related costs, over $28 billion yearly in the US. Despite advances and new therapies, no evidence of disease activity (NEDA) rates are 30-40%, yearly relapse rates for MS are still 30%, with only minimal effects on the progression of disease and time to disability. The pathogenesis of MS is thought to involve pathogenic Th17 cells, which are increased in the absence of LANCL3 and LANCL2. Loss of LANCL3 has been shown to increase disease severity in MS.

Methods

Mouse model. C57BL6 mice will be challenged at 6- to 8-weeks of age with MOG immunization. Complete Freund's adjuvant (CFA) will be prepared by suspension of heat-killed *Mycobacterium tuberculosis* (H37RA) at 10 mg/mL in incomplete Freund's adjuvant. MOG35-55 will be resuspended in sterile nanopure water to a concentration of 2 mg/mL. CFA and MOG35-55 solution will be emulsified in a 1:1 ratio using glass syringes and a near-closed three-way valve for 10 minutes. Emulsion will be left to sit for 30 prior to immunization to ensure it is stable. Pertussis toxin will be resuspended to a concentration of 2 µg/mL in PBS. MOG emulsion will be administered to the left and right flank at 100 per site to each mouse. Pertussis toxin will be administered by intraperitoneal injection (200 µL) on days 0 and 2 of the study to each mouse. Mice will be treated daily with BT-108-1 at 20 mg/kg. Treatment will be delivered by oral gavage. Mice will be scored (0-4) daily for disease activity (coordination, gait, paralysis).

Gene expression. Total RNA from spinal cord will be generated using the Qiagen RNeasy mini kit. cDNA will be generated using the BioRad iScript cDNA synthesis kit. Standard curves will be generated by serial dilution of purified product from a standard PCR reaction with Taq DNA polymerase followed by purification using the Qiagen MinElute PCR purification kit. Expression levels will be obtained from quantitative real-time PCR with SybrGreen supermix on a BioRad CFX96 Thermal cycler followed by normalization to expression of β-actin. Gene expression will be measured for inflammatory cytokines, IL-17, and TNF.

Results

Oral BT-108-1 is expected to decrease the disease activity scores of EAE mice relative to vehicle treated controls. BT-108-1 treated mice would be expected to have lower expression of IL17 and TNF in spinal cord samples relative to vehicle treatment.

REFERENCES

1. Chung, C. H., B. T. Kurien, P. Mehta, M. Mhatre, S. Mou, Q. N. Pye, C. Stewart, M. West, K. S. Williamson, J. Post, L. Liu, R. Wang, and K. Hensley, *Identification of lanthionine synthase C-like protein-1 as a prominent glutathione binding protein expressed in the mammalian central nervous system*. Biochemistry, 2007. 46(11): p. 3262-3269.
2. Xie, Z., B. Q. Cao, T. Wang, Q. Lei, T. Kang, C. Y. Ge, W. J. Gao, and H. Hui, *LanCL1 attenuates ischemia-induced oxidative stress by Sirt3-mediated preservation of mitochondrial function*. Brain Res Bull, 2018. 142: p. 216-223.
3. Leber, A., R. Hontecillas, V. Zoccoli-Rodriguez, and J. Bassaganya-Riera, *Activation of LANCL2 by BT-11 Ameliorates IBD by Supporting Regulatory T Cell Stability Through Immunometabolic Mechanisms*. Inflamm Bowel Dis, 2018. 24(9): p. 1978-1991.
4. Myers, S. A., A. Rhoads, A. R. Cocco, R. Peckner, A. L. Haber, L. D. Schweitzer, K. Krug, D. R. Mani, K. R. Clauser, O. Rozenblatt-Rosen, N. Hacohen, A. Regev, and S. A. Carr, *Streamlined Protocol for Deep Proteomic Profiling of FAC-sorted Cells and Its Application to*

*Freshly Isolated Murine Immune Cells.* Mol Cell Proteomics, 2019. 18(5): p. 995-1009.
5. Zocchi, E., R. Hontecillas, A. Leber, A. Einerhand, A. Carbo, S. Bruzzone, N. Tubau-Juni, N. Philipson, V. Zoccoli-Rodriguez, L. Sturla, and J. Bassaganya-Riera, *Abscisic Acid: A Novel Nutraceutical for Glycemic Control.* Front Nutr, 2017. 4: p. 24.
6. Taman, H., C. G. Fenton, I. V. Hensel, E. Anderssen, J. Florholmen, and R. H. Paulssen, *Transcriptomic Landscape of Treatment-Naive Ulcerative Colitis.* J Crohns Colitis, 2018. 12(3): p. 327-336.
7. Becker, A. M., K. H. Dao, B. K. Han, R. Kornu, S. Lakhanpal, A. B. Mobley, Q. Z. Li, Y. Lian, T. Wu, A. M. Reimold, N. J. Olsen, D. R. Karp, F. Z. Chowdhury, J. D. Farrar, A. B. Satterthwaite, C. Mohan, P. E. Lipsky, E. K. Wakeland, and L. S. Davis, *SLE peripheral blood B cell, T cell and myeloid cell transcriptomes display unique profiles and each subset contributes to the interferon signature.* PLoS One, 2013. 8(6): p. e67003.
8. Guri, A. J., R. Hontecillas, and J. Bassaganya-Riera, *Abscisic acid ameliorates experimental IBD by down-regulating cellular adhesion molecule expression and suppressing immune cell infiltration.* Clin Nutr, 2010. 29(6): p. 824-831.
9. Leber, A., R. Hontecillas, N. Tubau-Juni, V. Zoccoli-Rodriguez, B. Goodpaster, and J. Bassaganya-Riera, *Abscisic acid enriched fig extract promotes insulin sensitivity by decreasing systemic inflammation and activating LANCL2 in skeletal muscle.* Sci Rep, 2020. 10(1): p. 10463.
10. Zhang, W., L. Wang, Y. Liu, J. Xu, G. Zhu, H. Cang, X. Li, M. Bartlam, K. Hensley, G. Li, Z. Rao, and X. C. Zhang, *Structure of human lanthionine synthetase C-like protein 1 and its interaction with Eps8 and glutathione.* Genes Dev, 2009. 23(12): p. 1387-1392.
11. Tsuchida, T., Y. A. Lee, N. Fujiwara, M. Ybanez, B. Allen, S. Martins, M. I. Fiel, N. Goossens, H. I. Chou, Y. Hoshida, and S. L. Friedman, *A simple diet-and chemical-induced murine NASH model with rapid progression of steatohepatitis, fibrosis and liver cancer.* J Hepatol, 2018. 69(2): p. 385-395.
12. Abreu, M. T., *Toll-like receptor signalling in the intestinal epithelium: how bacterial recognition shapes intestinal function.* Nat Rev Immunol, 2010. 10(2): p. 131-144.

Exemplary Embodiments of the Invention

1. A compound of Formula (I):

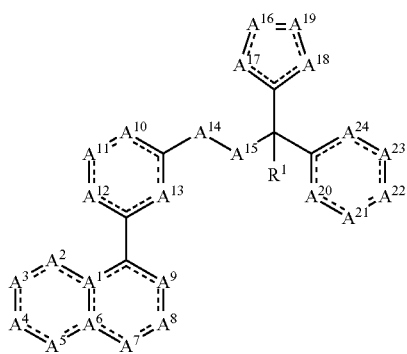

(I)

or a salt or ester thereof, wherein:
$A^1$ and $A^6$ are each C;
$A^2, A^3, A^4, A^5, A^7, A^8, A^9, A^{10}, A^{11}, A^{12}, A^{13}, A^{20}, A^{21}, A^{22}, A^{23}$, and $A^{24}$ are each independently N or $C(R^2)$;
$A^{14}$ and $A^{15}$ are each C(O) or $N(R^L)$, with the proviso that $A^{14}$ and $A^{15}$ are not both C(O) and are not both $N(R^L)$;
$A^{16}, A^{17}, A^{18}$, and $A^{19}$ are each independently selected from O, $N(R^2)$, S, N, and $C(R^2)$, with the proviso that one and only one of $A^{16}, A^{17}, A^{18}$, and $A^{19}$ is O, $N(R^2)$, or S;
- - - represents delocalized pi bonds;
$R^1$, $R^2$, and $R^L$ in each instance are independently hydrogen, halogen, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, thiol, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

2. The compound of embodiment 1, wherein $A^2$ is $C(R^2)$.
3. The compound of embodiment 2, wherein the $R^2$ of the $C(R^2)$ of $A^2$ is hydrogen or halogen.
4. The compound of embodiment 1, wherein $A^2$ is N.
5. The compound of any prior embodiment, wherein $A^3$ is $C(R^2)$.
6. The compound of embodiment 5, wherein the $R^2$ of the $C(R^2)$ of $A^3$ is hydrogen or halogen.
7. The compound of embodiment 5, wherein the $R^2$ of the $C(R^2)$ of $A^3$ is not hydrogen.
8. The compound of embodiment 5, wherein the $R^2$ of the $C(R^2)$ of $A^3$ is optionally substituted alkyl, optionally substituted alkyloxy, carboxyl, or optionally substituted alkyloxycarbonyl.
9. The compound of embodiment 5, wherein the $R^2$ of the $C(R^2)$ of $A^3$ is C1-C6 unsubstituted alkyl, trifluoromethyl, unsubstituted C1-C4 alkyloxy, carboxyl, or unsubstituted C1-C4 alkyloxycarbonyl.
10. The compound of any prior embodiment, wherein $A^4$ is $C(R^2)$.
11. The compound of embodiment 10, wherein the $R^2$ of the $C(R^2)$ of $A^4$ is hydrogen or halogen.
12. The compound of any prior embodiment, wherein $A^5$ is $C(R^2)$.
13. The compound of embodiment 12, wherein the $R^2$ of the $C(R^2)$ of $A^5$ is hydrogen or halogen.

14. The compound of any prior embodiment, wherein $A^7$ is $C(R^2)$.

15. The compound of embodiment 14, wherein the $R^2$ of the $C(R^2)$ of $A^7$ is hydrogen or halogen.

16. The compound of any one of embodiments 1-13, wherein $A^7$ is N.

17. The compound of any prior embodiment, wherein $A^8$ is N.

18. The compound of any prior embodiment, wherein $A^9$ is $C(R^2)$.

19. The compound of embodiment 18, wherein the $R^2$ of the $C(R^2)$ of $A^9$ is hydrogen or halogen.

20. The compound of embodiment 18, wherein the $R^2$ of the $C(R^2)$ of $A^9$ is not hydrogen.

21. The compound of embodiment 18, wherein the $R^2$ of the $C(R^2)$ of $A^9$ is optionally substituted alkyl, optionally substituted alkyloxy, carboxyl, or optionally substituted alkyloxycarbonyl.

22. The compound of embodiment 18, wherein the $R^2$ of the $C(R^2)$ of $A^9$ is C1-C6 unsubstituted alkyl, trifluoromethyl, unsubstituted C1-C4 alkyloxy, carboxyl, or unsubstituted C1-C4 alkyloxycarbonyl.

23. The compound of any prior embodiment, wherein $A^{10}$ is $C(R^2)$.

24. The compound of embodiment 23, wherein the $R^2$ of the $C(R^2)$ of $A^{10}$ is hydrogen or halogen.

25. The compound of embodiment 23, wherein the $R^2$ of the $C(R^2)$ of $A^{10}$ is not hydrogen.

26. The compound of embodiment 23, wherein the $R^2$ of the $C(R^2)$ of $A^{10}$ is optionally substituted alkyl, optionally substituted alkyloxy, carboxyl, or optionally substituted alkyloxycarbonyl.

27. The compound of embodiment 23, wherein the $R^2$ of the $C(R^2)$ of $A^{10}$ is C1-C6 unsubstituted alkyl, trifluoromethyl, unsubstituted C1-C4 alkyloxy, carboxyl, or unsubstituted C1-C4 alkyloxycarbonyl.

28. The compound of any prior embodiment, wherein $A^{11}$ is $C(R^2)$.

29. The compound of embodiment 28, wherein the $R^2$ of the $C(R^2)$ of $A^{11}$ is hydrogen or halogen.

30. The compound of embodiment 28, wherein the $R^2$ of the $C(R^2)$ of $A^{11}$ is not hydrogen.

31. The compound of embodiment 28, wherein the $R^2$ of the $C(R^2)$ of $A^{11}$ is optionally substituted alkyl, optionally substituted alkyloxy, carboxyl, or optionally substituted alkyloxycarbonyl.

32. The compound of embodiment 28, wherein the $R^2$ of the $C(R^2)$ of $A^{11}$ is C1-C6 unsubstituted alkyl, trifluoromethyl, unsubstituted C1-C4 alkyloxy, carboxyl, or unsubstituted C1-C4 alkyloxycarbonyl.

33. The compound of any one of embodiments 1-27, wherein $A^{11}$ is N.

34. The compound of any prior embodiment, wherein $A^{12}$ is $C(R^2)$.

35. The compound of embodiment 34, wherein the $R^2$ of the $C(R^2)$ of $A^{12}$ is hydrogen or halogen.

36. The compound of embodiment 34, wherein the $R^2$ of the $C(R^2)$ of $A^{12}$ is not hydrogen.

37. The compound of embodiment 34, wherein the $R^2$ of the $C(R^2)$ of $A^{12}$ is optionally substituted alkyl, optionally substituted alkyloxy, carboxyl, or optionally substituted alkyloxycarbonyl.

38. The compound of embodiment 34, wherein the $R^2$ of the $C(R^2)$ of $A^{12}$ is C1-C6 unsubstituted alkyl, trifluoromethyl, unsubstituted C1-C4 alkyloxy, carboxyl, or unsubstituted C1-C4 alkyloxycarbonyl.

39. The compound of any prior embodiment, wherein $A^{13}$ is $C(R^2)$.

40. The compound of embodiment 39, wherein the $R^2$ of the $C(R^2)$ of $A^{13}$ is hydrogen or halogen.

41. The compound of embodiment 39, wherein the $R^2$ of the $C(R^2)$ of $A^{13}$ is not hydrogen.

42. The compound of embodiment 39, wherein the $R^2$ of the $C(R^2)$ of $A^{13}$ is optionally substituted alkyl, optionally substituted alkyloxy, carboxyl, or optionally substituted alkyloxycarbonyl.

43. The compound of embodiment 39, wherein the $R^2$ of the $C(R^2)$ of $A^{13}$ is C1-C6 unsubstituted alkyl, trifluoromethyl, unsubstituted C1-C4 alkyloxy, carboxyl, or unsubstituted C1-C4 alkyloxycarbonyl.

44. The compound of any one of embodiments 1-38, wherein $A^{13}$ is N.

45. The compound of any prior embodiment, wherein $A^{14}$ is $N(R^L)$ and $A^{15}$ is $C(O)$.

46. The compound of any one of embodiments 1-44, wherein $A^{14}$ is $C(O)$ and $A^{15}$ is $N(R^L)$.

47. The compound of any prior embodiment, wherein $R^L$ is hydrogen or halogen.

48. The compound of any prior embodiment, wherein $A^{17}$ is N.

49. The compound of any prior embodiment, wherein $A^{16}$ is $C(R^2)$.

50. The compound of embodiment 49, wherein the $R^2$ of the $C(R^2)$ of $A^{16}$ is hydrogen or halogen.

51. The compound of any prior embodiment, wherein $A^{19}$ is $C(R^2)$.

52. The compound of embodiment 51, wherein the $R^2$ of the $C(R^2)$ of $A^{19}$ is hydrogen or halogen.

53. The compound of any prior embodiment, wherein $A^{18}$ is $N(R^2)$.

54. The compound of embodiment 53, wherein the $R^2$ of the $N(R^2)$ of $A^{18}$ is hydrogen or halogen.

55. The compound of any prior embodiment, wherein $A^{20}$ is $C(R^2)$.

56. The compound of embodiment 55, wherein the $R^2$ of the $C(R^2)$ of $A^{20}$ is hydrogen or halogen.

57. The compound of embodiment 55, wherein the $R^2$ of the $C(R^2)$ of $A^{20}$ is not hydrogen.

58. The compound of embodiment 55, wherein the $R^2$ of the $C(R^2)$ of $A^{20}$ is optionally substituted alkyl, optionally substituted alkyloxy, carboxyl, or optionally substituted alkyloxycarbonyl.

59. The compound of embodiment 55, wherein the $R^2$ of the $C(R^2)$ of $A^{20}$ is C1-C6 unsubstituted alkyl, trifluoromethyl, unsubstituted C1-C4 alkyloxy, carboxyl, or unsubstituted C1-C4 alkyloxycarbonyl.

60. The compound of any one of embodiments 1-54, wherein $A^{20}$ is N.

61. The compound of any prior embodiment, wherein $A^{21}$ is $C(R^2)$.

62. The compound of embodiment 61, wherein the $R^2$ of the $C(R^2)$ of $A^{21}$ is hydrogen or halogen.

63. The compound of embodiment 61, wherein the $R^2$ of the $C(R^2)$ of $A^{21}$ is not hydrogen.

64. The compound of embodiment 61, wherein the $R^2$ of the $C(R^2)$ of $A^{21}$ is optionally substituted alkyl, optionally substituted alkyloxy, carboxyl, or optionally substituted alkyloxycarbonyl.

65. The compound of embodiment 61, wherein the $R^2$ of the $C(R^2)$ of $A^{21}$ is C1-C6 unsubstituted alkyl, trifluoromethyl, unsubstituted C1-C4 alkyloxy, carboxyl, or unsubstituted C1-C4 alkyloxycarbonyl.

66. The compound of any one of embodiments 1-60, wherein $A^{21}$ is N.

67. The compound of any prior embodiment, wherein $A^{22}$ is $C(R^2)$.

68. The compound of embodiment 67, wherein the $R^2$ of the $C(R^2)$ of $A^{22}$ is hydrogen or halogen.

69. The compound of embodiment 67, wherein the $R^2$ of the $C(R^2)$ of $A^{22}$ is not hydrogen.

70. The compound of embodiment 67, wherein the $R^2$ of the $C(R^2)$ of $A^{22}$ is optionally substituted alkyl, optionally substituted alkyloxy, carboxyl, or optionally substituted alkyloxycarbonyl.

71. The compound of embodiment 67, wherein the $R^2$ of the $C(R^2)$ of $A^{22}$ is C1-C6 unsubstituted alkyl, trifluoromethyl, unsubstituted C1-C4 alkyloxy, carboxyl, or unsubstituted C1-C4 alkyloxycarbonyl.

72. The compound of any one of embodiments 1-66, wherein $A^{22}$ is N.

73. The compound of any prior embodiment, wherein $A^{23}$ is $C(R^2)$.

74. The compound of embodiment 73, wherein the $R^2$ of the $C(R^2)$ of $A^{23}$ is hydrogen or halogen.

75. The compound of embodiment 73, wherein the $R^2$ of the $C(R^2)$ of $A^{23}$ is not hydrogen.

76. The compound of embodiment 73, wherein the $R^2$ of the $C(R^2)$ of $A^{23}$ is optionally substituted alkyl, optionally substituted alkyloxy, carboxyl, or optionally substituted alkyloxycarbonyl.

77. The compound of embodiment 73, wherein the $R^2$ of the $C(R^2)$ of $A^{23}$ is C1-C6 unsubstituted alkyl, trifluoromethyl, unsubstituted C1-C4 alkyloxy, carboxyl, or unsubstituted C1-C4 alkyloxycarbonyl.

78. The compound of any one of embodiments 1-72, wherein $A^{23}$ is N.

79. The compound of any prior embodiment, wherein $A^{24}$ is $C(R^2)$.

80. The compound of embodiment 79, wherein the $R^2$ of the $C(R^2)$ of $A^{24}$ is hydrogen or halogen.

81. The compound of embodiment 79, wherein the $R^2$ of the $C(R^2)$ of $A^{24}$ is not hydrogen.

82. The compound of embodiment 79, wherein the $R^2$ of the $C(R^2)$ of $A^{24}$ is optionally substituted alkyl, optionally substituted alkyloxy, carboxyl, or optionally substituted alkyloxycarbonyl.

83. The compound of embodiment 79, wherein the $R^2$ of the $C(R^2)$ of $A^{24}$ is C1-C6 unsubstituted alkyl, trifluoromethyl, unsubstituted C1-C4 alkyloxy, carboxyl, or unsubstituted C1-C4 alkyloxycarbonyl.

84. The compound of any one of embodiments 1-78, wherein $A^{24}$ is N.

85. The compound of any prior embodiment, wherein $R^1$ is not hydrogen.

86. The compound of any prior embodiment, wherein $R^1$ is hydroxyl or optionally substituted alkyloxy.

87. The compound of any prior embodiment, wherein $R^1$ is hydroxyl or unsubstituted C1-C4 alkyloxy.

88. The compound of embodiment 1, wherein: $A^2$ is $C(R^2)$; $A^3$ is $C(R^2)$; $A^4$ is $C(R^2)$; $A^5$ is $C(R^2)$; $A^7$ is N; $A^8$ is N; and $A^9$ is $C(R^2)$.

89. The compound of embodiment 88, wherein the $R^2$ on the $C(R^2)$ of $A^3$ is optionally substituted alkyl, optionally substituted alkyloxy, carboxyl, or optionally substituted alkyloxycarbonyl.

90. The compound of embodiment 88, wherein the $R^2$ on the $C(R^2)$ of $A^3$ is optionally substituted alkyl.

91. The compound of embodiment 88, wherein the $R^2$ on the $C(R^2)$ of $A^3$ is trifluoromethyl.

92. The compound of any one of embodiments 1 and 88-91, wherein: $A^{10}$ is $C(R^2)$; $A^{11}$ is N; $A^{12}$ is $C(R^2)$; and $A^{13}$ is $C(R^2)$.

93. The compound of embodiment 92, wherein the $R^2$ on the $C(R^2)$ of $A^{10}$ is optionally substituted alkyl, optionally substituted alkyloxy, carboxyl, or optionally substituted alkyloxycarbonyl.

94. The compound of embodiment 92, wherein the $R^2$ on the $C(R^2)$ of $A^{10}$ is optionally substituted alkyloxy.

95. The compound of embodiment 92, wherein the $R^2$ on the $C(R^2)$ of $A^{13}$ is optionally substituted alkyl, optionally substituted alkyloxy, carboxyl, or optionally substituted alkyloxycarbonyl.

96. The compound of embodiment 92, wherein the $R^2$ on the $C(R^2)$ of $A^{13}$ is optionally substituted alkyl.

97. The compound of any one of embodiments 1 and 88-96, wherein $A^{14}$ is $N(R^L)$ and $A^{15}$ is $C(O)$.

98. The compound of embodiment 97, wherein $R^L$ is hydrogen or halogen.

99. The compound of any one of embodiments 1 and 87-98, wherein: $A^{16}$ is $C(R^2)$; $A^{17}$ is N; $A^{18}$ is $N(R^2)$; and $A^{19}$ is $C(R^2)$.

100. The compound of any one of embodiments 1 and 88-99, wherein each of $A^{20}$, $A^{21}$, $A^{22}$, $A^{23}$, and $A^{24}$ is independently $C(R^2)$.

101. The compound of embodiment 100, wherein the $R^2$ on the $C(R^2)$ of $A^{24}$ is optionally substituted alkyl, optionally substituted alkyloxy, carboxyl, or optionally substituted alkyloxycarbonyl.

102. The compound of embodiment 100, wherein the $R^2$ on the $C(R^2)$ of $A^{24}$ is optionally substituted alkyl.

103. The compound of embodiment 100, wherein the $R^2$ on the $C(R^2)$ of $A^{21}$ is optionally substituted alkyl, optionally substituted alkyloxy, carboxyl, or optionally substituted alkyloxycarbonyl.

104. The compound of embodiment 100, wherein the $R^2$ on the $C(R^2)$ of $A^{21}$ is optionally substituted alkyloxy.

105. The compound of any one of embodiments 1 and 88-104, wherein the $R^1$ is hydroxyl or optionally substituted alkyloxy.

106. The compound of any one of embodiments 1 and 88-105, wherein the $R^1$ is hydroxyl or unsubstituted C1-C4 alkyloxy.

107. The compound of any prior embodiment, wherein $R^1$, $R^2$, and $R^L$ in each instance are independently, unless otherwise defined, hydrogen, halogen, optionally substituted C1-C6 alkyl, hydroxyl, carboxyl, optionally substituted cycloalkyl, optionally substituted C1-C6 alkyloxy, optionally substituted amino, acyl, optionally substituted alkyloxycarbonyl, optionally substituted aryl, optionally substituted heteroaryl, or optionally substituted non-aromatic heterocyclic group.

108. The compound of any prior embodiment, wherein $R^1$, $R^2$, and $R^L$ in each instance are independently, unless otherwise defined, hydrogen, halogen, unsubstituted C1-C6 alkyl, hydroxyl, carboxyl, unsubstituted cycloalkyl, unsubstituted C1-C6 alkyloxy, unsubstituted amino, acyl, unsubstituted alkyloxycarbonyl, unsubstituted aryl, unsubstituted heteroaryl, or unsubstituted non-aromatic heterocyclic group.

109. The compound of any prior embodiment, wherein $R^1$, $R^2$, and $R^L$ in each instance are independently, unless otherwise defined, hydrogen or halogen.

110. The compound of embodiment 1, wherein the compound is any one of the compounds shown in FIGS. 1A-1N, or a salt thereof.

111. A method of treating a condition in an animal with a compound as recited in any one of embodiments 1-110, the method comprising administering an effective amount of the compound to the animal, wherein the condition comprises at least one of an inflammatory disease, a metabolic disease, an autoimmune disease, cancer, and an infectious disease.

112. The method of 111, wherein the condition comprises an autoimmune disease.

113. The method of embodiment 112, wherein the autoimmune disease comprises inflammatory bowel disease.

114. The method of embodiment 113, wherein the inflammatory bowel disease comprises Crohn's disease.

115. The method of embodiment 113, wherein the inflammatory bowel disease comprises ulcerative colitis.

116. The method of embodiment 112, wherein the autoimmune disease comprises at least one of systemic lupus erythematosus, lupus nephritis, and cutaneous lupus.

117. The method of embodiment 112, wherein the autoimmune disease comprises rheumatoid arthritis.

118. The method of embodiment 112, wherein the autoimmune disease comprises type 1 diabetes.

119. The method of embodiment 112, wherein the autoimmune disease comprises psoriasis.

120. The method of embodiment 111, wherein the condition comprises a metabolic disease.

121. The method of embodiment 120, wherein metabolic the disease comprises at least one of prediabetes and type 2 diabetes.

122. The method of embodiment 111, wherein the condition comprises an inflammatory disease.

123. The method of embodiment 122, wherein the inflammatory disease comprises at least one of nonalcoholic fatty liver disease, nonalcoholic steatohepatitis, and cirrhosis.

124. The method of embodiment 111, wherein the condition comprises an infectious disease.

125. The method of embodiment 124, wherein the infectious disease comprises viral infection.

126. A method of treating a condition in an animal with a compound that binds LANCL3 or LANCL3 and LANCL2, wherein the condition comprises at least one of an inflammatory disease, a metabolic disease, an autoimmune disease, cancer, and an infectious disease.

127. The method of embodiment 126, wherein the compound is a compound as recited in any one of embodiments 1-110.

128. The method of embodiment 126, wherein the method comprises a method as recited in any one of embodiments 111-125.

We claim:

1. A compound of Formula (I):

or a salt or ester thereof, wherein:

$A^1$ and $A^6$ are each C;

$A^2$ and $A^7$ are each independently N or $C(R^2)$, with the proviso that at least one of $A^2$ and $A^7$ is N;

$A^3$, $A^4$, $A^5$, and $A^9$ are each $C(R^2)$;

$A^8$ is N;

$A^{11}$ and $A^{13}$ are each independently N or $C(R^2)$, with the proviso that at least one of $A^{11}$ and $A^{13}$ is N;

$A^{14}$ and $A^{15}$ are each C(O) or $N(R^L)$, with the proviso that $A^{14}$ and $A^{15}$ are not both C(O) and are not both $N(R^L)$;

$A^{16}$, $A^{17}$, $A^{18}$, and $A^{19}$ are each independently selected from O, $N(R^2)$, S, N, and $C(R^2)$, with the provisos that: $A^{17}$ is N, $A^{18}$ is $N(R^2)$, or $A^{17}$ is N and $A^{18}$ is $N(R^2)$; and one and only one of $A^{16}$, $A^{17}$, $A^{18}$, and $A^{19}$ is O, $N(R^2)$, or S;

$A^{10}$, $A^{12}$, $A^{20}$, $A^{21}$, $A^{22}$, $A^{23}$, and $A^{24}$ are each independently N or $C(R^2)$;

- - - represents delocalized pi bonds;

$R^1$ is hydroxyl or optionally substituted alkyloxy;

$R^2$ and $R^L$ in each instance are independently hydrogen, halogen, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, thiol, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

2. The compound of claim 1, wherein the $R^2$ of the $C(R^2)$ of each of $A^2$, $A^4$, $A^5$, and $A^7$, if present, is hydrogen.

3. The compound of claim 2, wherein the $R^2$ of the $C(R^2)$ of $A^3$ and the $R^2$ of the $C(R^2)$ of $A^9$ are each independently hydrogen, optionally substituted alkyl, optionally substituted alkyloxy, carboxyl, or optionally substituted alkyloxycarbonyl.

4. The compound of claim 1, wherein $A^{10}$ and $A^{12}$ are each $C(R^2)$.

5. The compound of claim 4, wherein the $R^2$ of each of $A^{10}$ and $A^{12}$ is hydrogen.

6. The compound of claim 1, wherein one or both of $A^{16}$ and $A^{19}$ is $C(R^2)$.

7. The compound of claim 6, wherein the $R^2$ of each of $A^{16}$, $A^{17}$, $A^{18}$, and $A^{19}$, if present, is hydrogen.

8. The compound of claim 1, wherein $A^{21}$, $A^{22}$, $A^{23}$, and $A^{24}$ are each independently $C(R^2)$.

9. The compound of claim 8, wherein the $R^2$ of the $C(R^2)$ of $A^{22}$ is hydrogen.

10. The compound of claim 8, wherein the $R^2$ of the $C(R^2)$ of each of $A^{20}$, $A^{21}$, $A^{22}$, $A^{23}$, and $A^{24}$, if present, is hydrogen.

11. The compound of claim 10, wherein $A^{20}$ is $C(R^2)$.

12. The compound of claim 8, wherein the $R^2$ of the $C(R^2)$ of each of $A^{20}$, $A^{22}$, and $A^{23}$, if present, is hydrogen.

13. The compound of claim 12, wherein:
$A^{20}$ is $C(R^2)$;
the $R^2$ of the $C(R^2)$ of $A^{21}$ is hydrogen; and
the $R^2$ of the $C(R^2)$ of $A^{24}$ is optionally substituted alkyl or optionally substituted alkyloxy.

14. The compound of claim 12, wherein:
$A^{20}$ is $C(R^2)$;
the $R^2$ of the $C(R^2)$ of $A^{24}$ is hydrogen; and
the $R^2$ of the $C(R^2)$ of $A^{21}$ is optionally substituted alkyl or optionally substituted alkyloxy.

15. The compound of claim 1, wherein $R^2$ and $R^L$ in each instance are independently hydrogen, halogen, unsubstituted alkyl, halogen-substituted alkyl, unsubstituted alkyloxy, halogen-substituted alkyloxy, carboxyl, unsubstituted alkyloxycarbonyl, or halogen-substituted alkyloxycarbonyl.

16. The compound of claim 1, wherein the $R^2$ of the $C(R^2)$ of each of $A^2$, $A^4$, $A^5$, $A^7$, $A^{16}$, $A^{17}$, $A^{18}$, $A^{19}$, and $A^{22}$, if present, is hydrogen.

17. The compound of claim 1, wherein:
$A^{10}$, $A^{12}$, $A^{21}$, $A^{22}$, $A^{23}$, and $A^{24}$ are each $C(R^2)$; and
one or both of $A^{16}$ and $A^{19}$ is $C(R^2)$.

18. The compound of claim 17, wherein $R^2$ and $R^L$ in each instance are independently hydrogen, halogen, unsubstituted alkyl, halogen-substituted alkyl, unsubstituted alkyloxy, halogen-substituted alkyloxy, carboxyl, unsubstituted alkyloxycarbonyl, or halogen-substituted alkyloxycarbonyl.

19. The compound of claim 17, wherein $R^2$ and $R^L$ in each instance are independently hydrogen, halogen, unsubstituted alkyl, halogen-substituted alkyl, unsubstituted alkyloxy, or halogen-substituted alkyloxy.

20. The compound of claim 19, wherein $R^1$ is hydroxyl or unsubstituted alkyloxy.

21. The compound of claim 20, wherein $R^L$ and the $R^2$ of the $C(R^2)$ of each of $A^2$, $A^4$, $A^5$, $A^7$, $A^{16}$, $A^{17}$, $A^{18}$, $A^{19}$, and $A^{22}$, if present, are each hydrogen.

22. The compound of claim 20, wherein:
$A^7$ and $A^{11}$ are N;
$A^2$, $A^{13}$, and $A^{20}$ are each $C(R^2)$; and
$R^L$ and the $R^2$ of the $C(R^2)$ of each of $A^2$, $A^4$, $A^5$, $A^9$, $A^{16}$, $A^{17}$, $A^{18}$, $A^{19}$, $A^{20}$, $A^{22}$, and $A^{23}$, if present, are each hydrogen.

23. The compound of claim 1, wherein the compound is any one of:

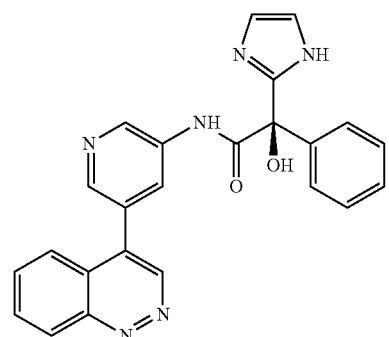

;

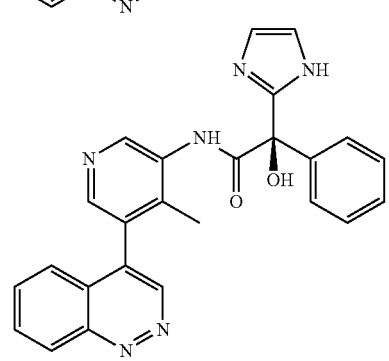

;

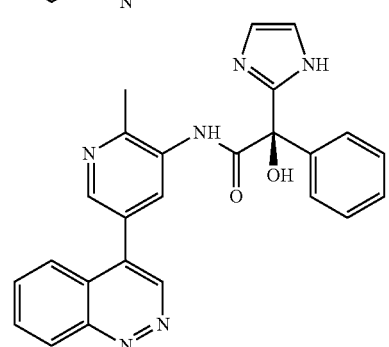

;

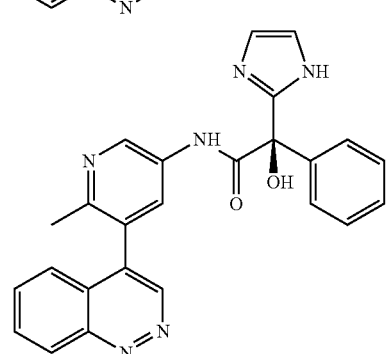

;

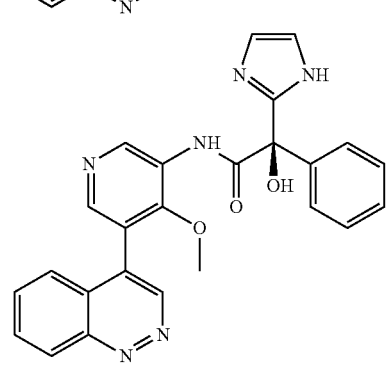

;

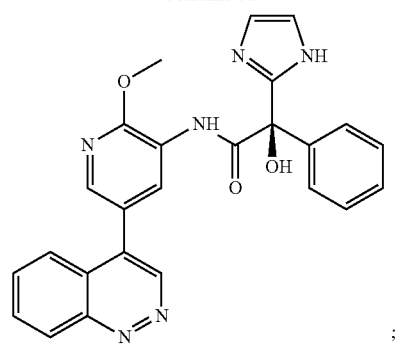
;
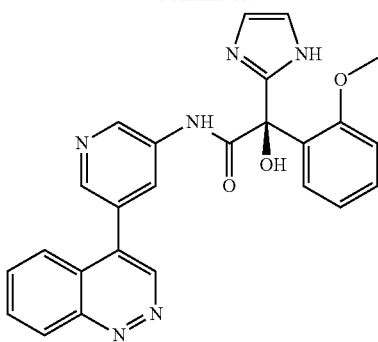
;
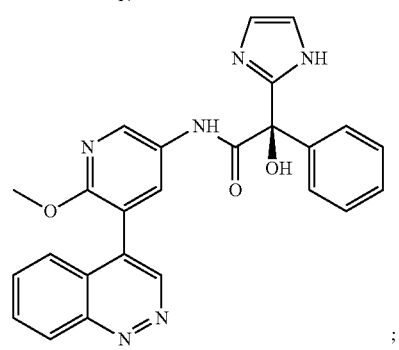
;
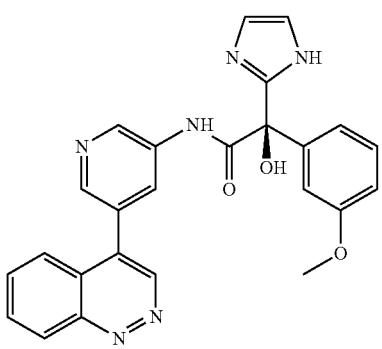
;
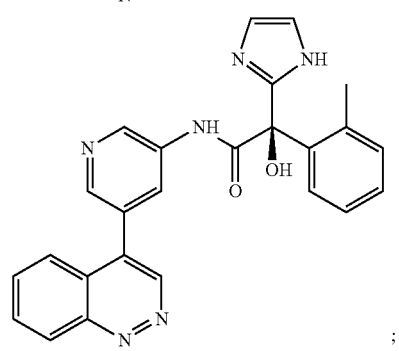
;
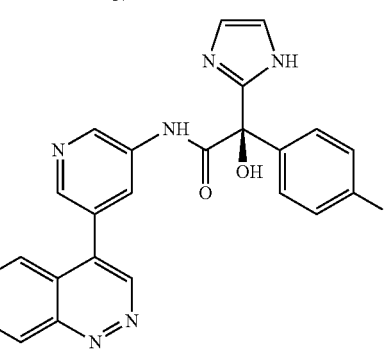
;
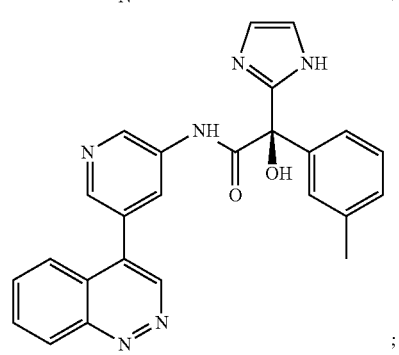
;
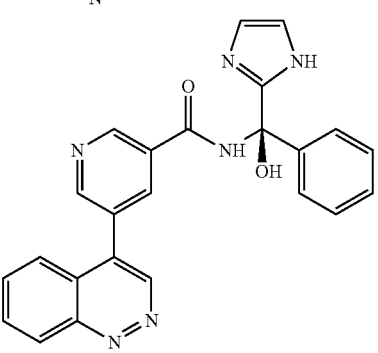
;
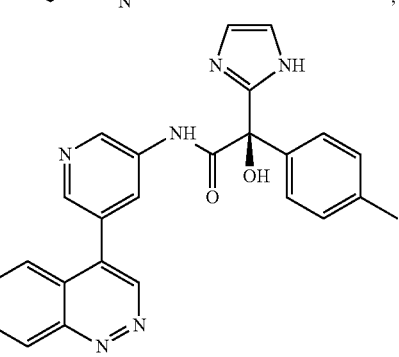
;
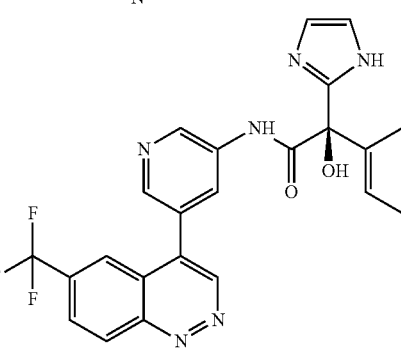
;

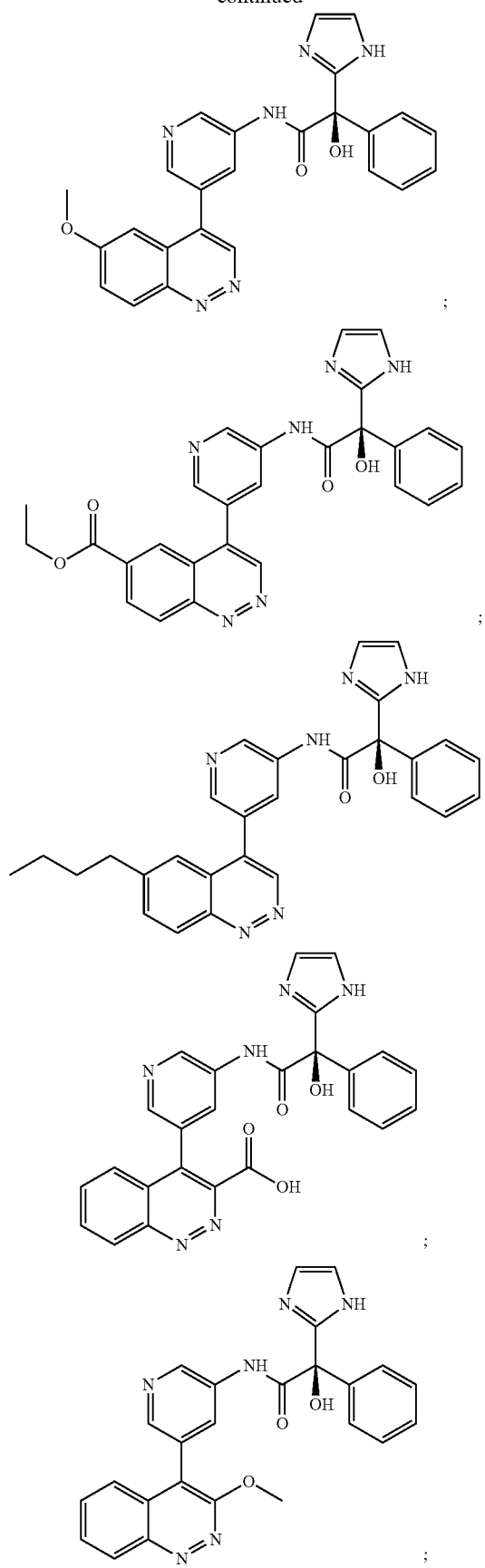
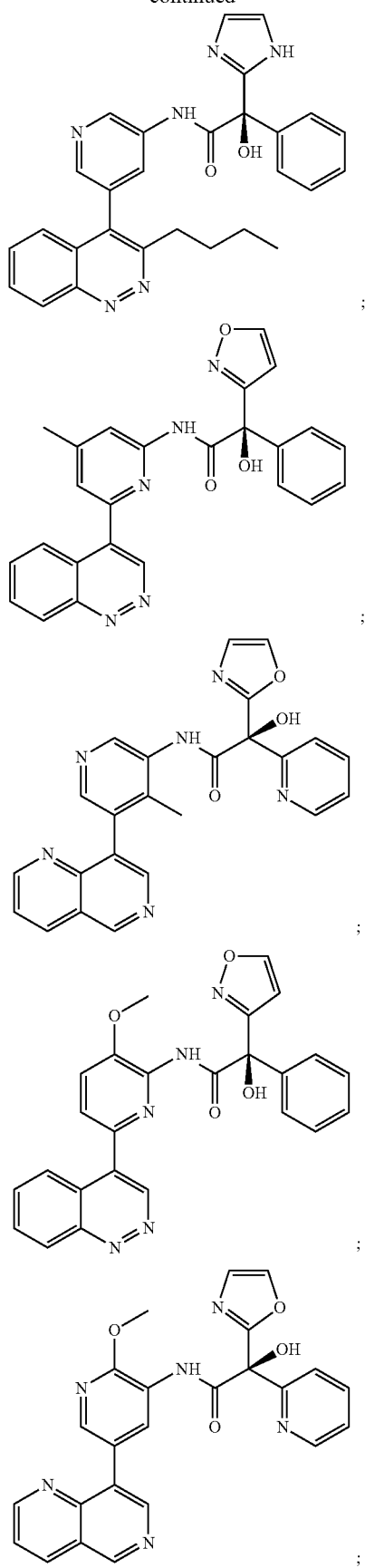

53
-continued
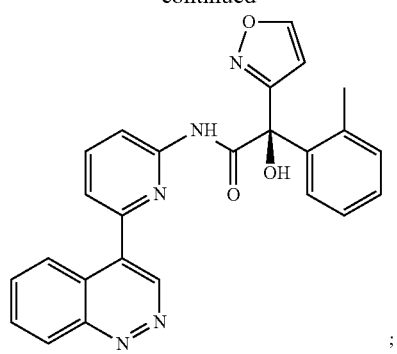
;
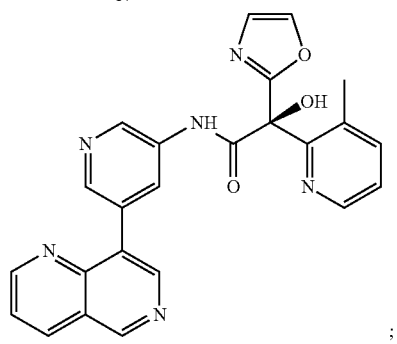
;
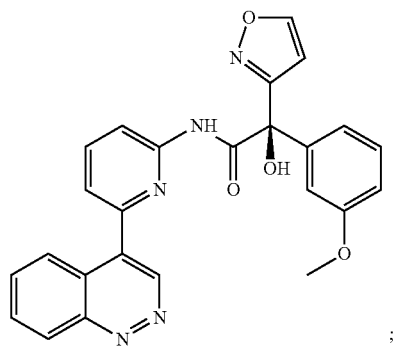
;
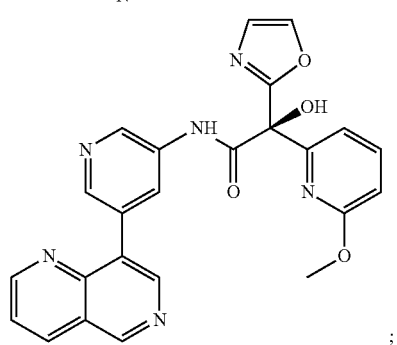
;
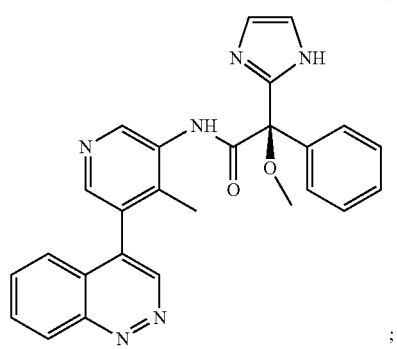
;
54
-continued
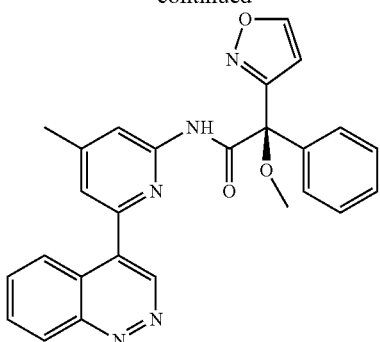
;
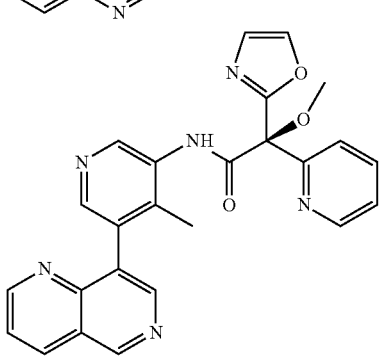
;
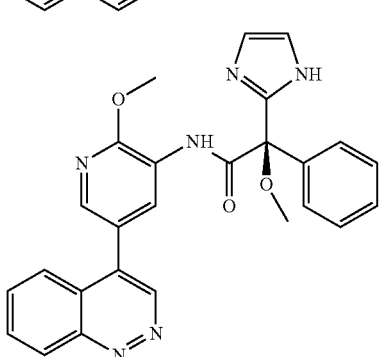
;
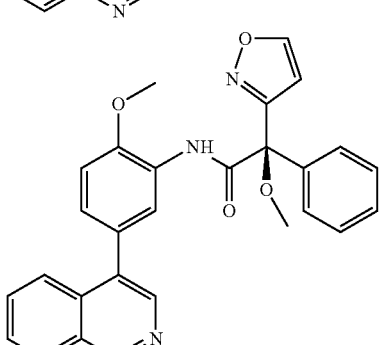
;
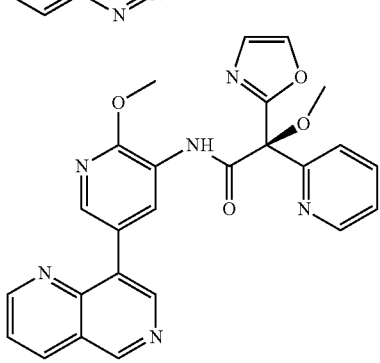
;

-continued
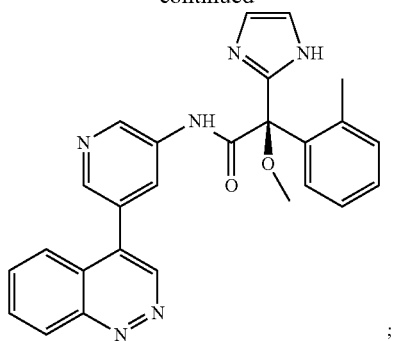
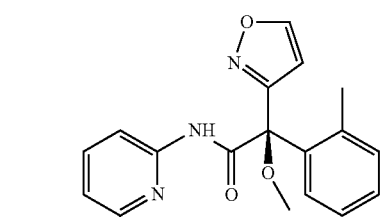
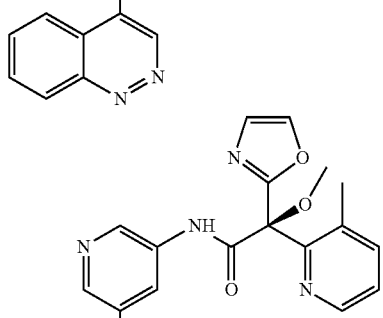
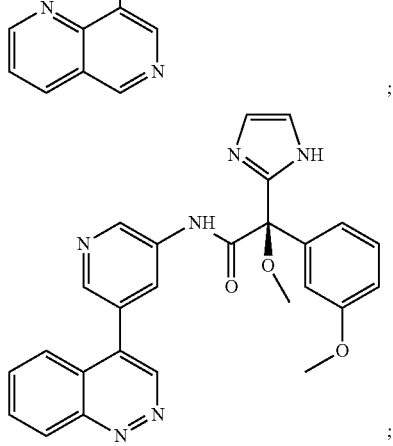
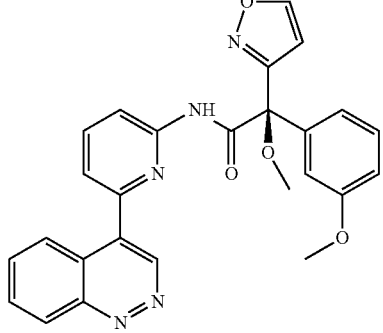
-continued
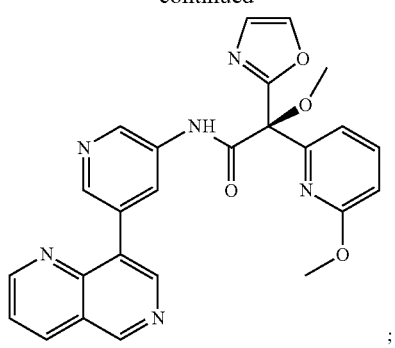
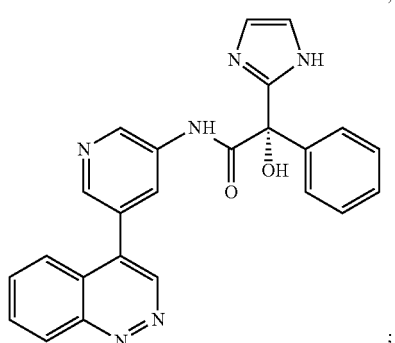
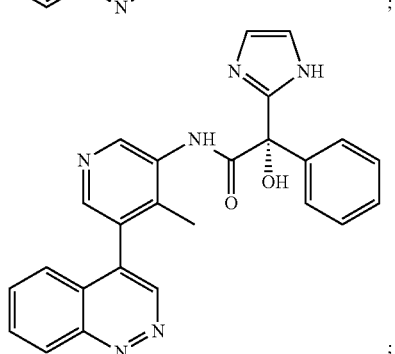
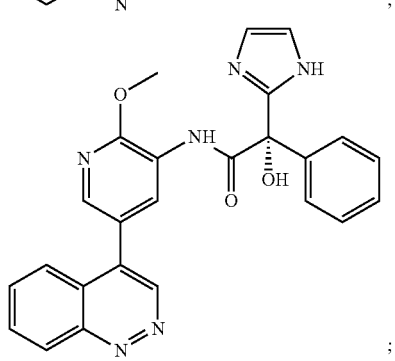
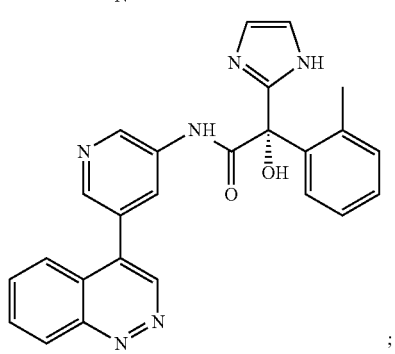

57
-continued
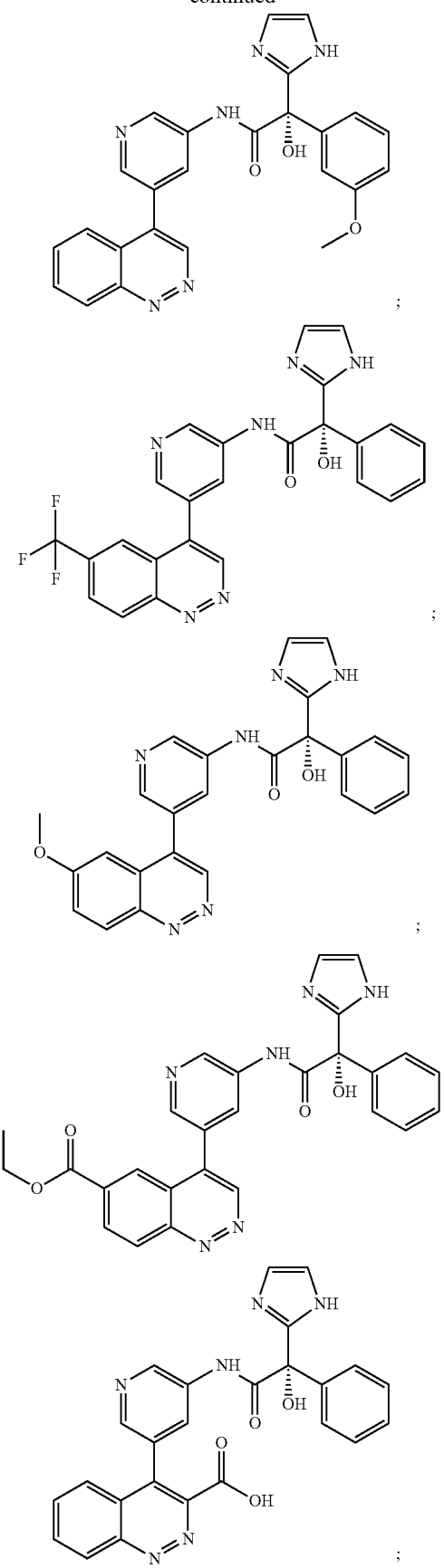
58
-continued
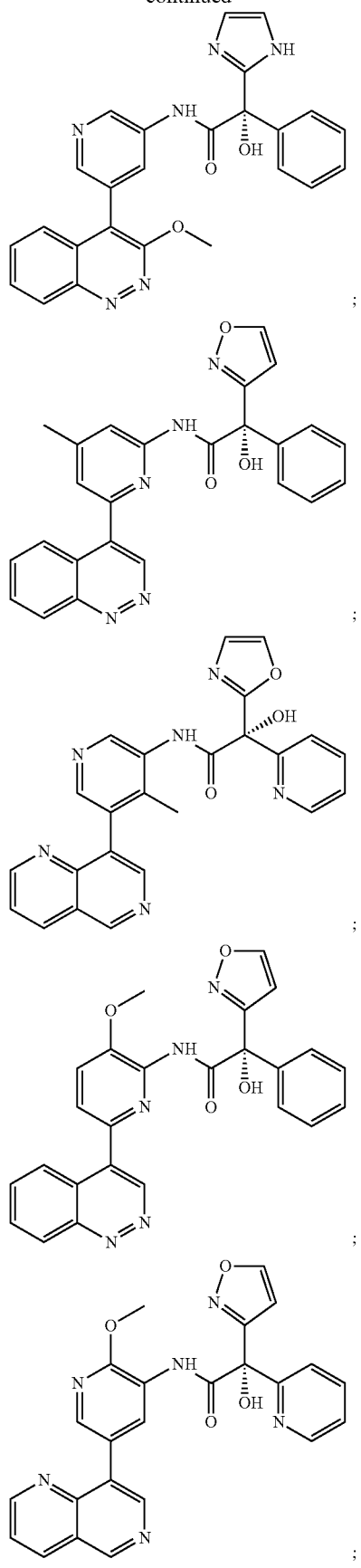

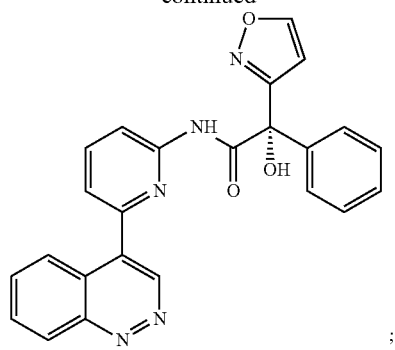
;
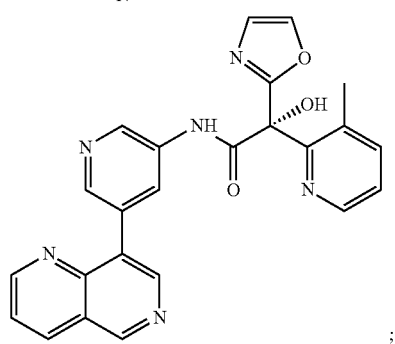
;
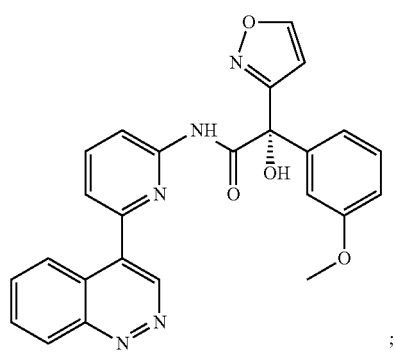
;
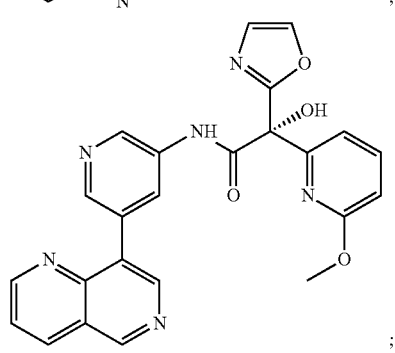
;
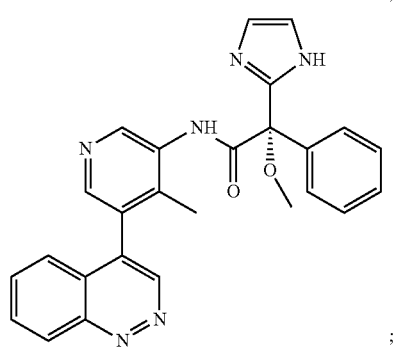
;
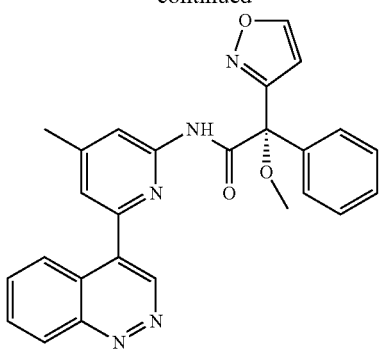
;
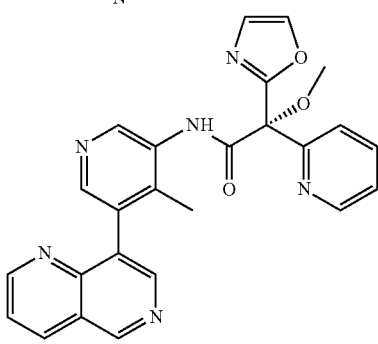
;
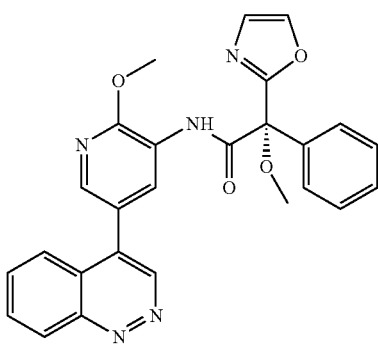
;
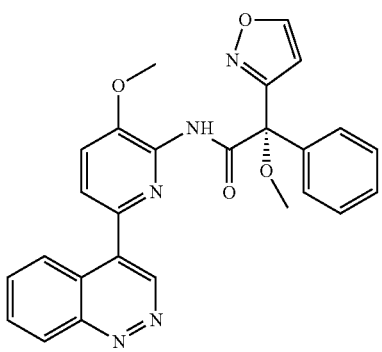
;
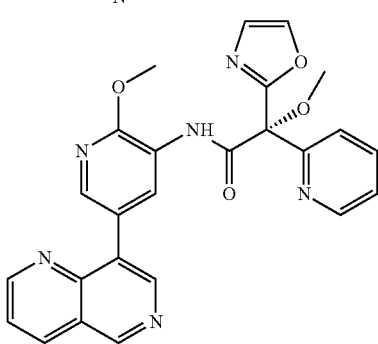
;

-continued
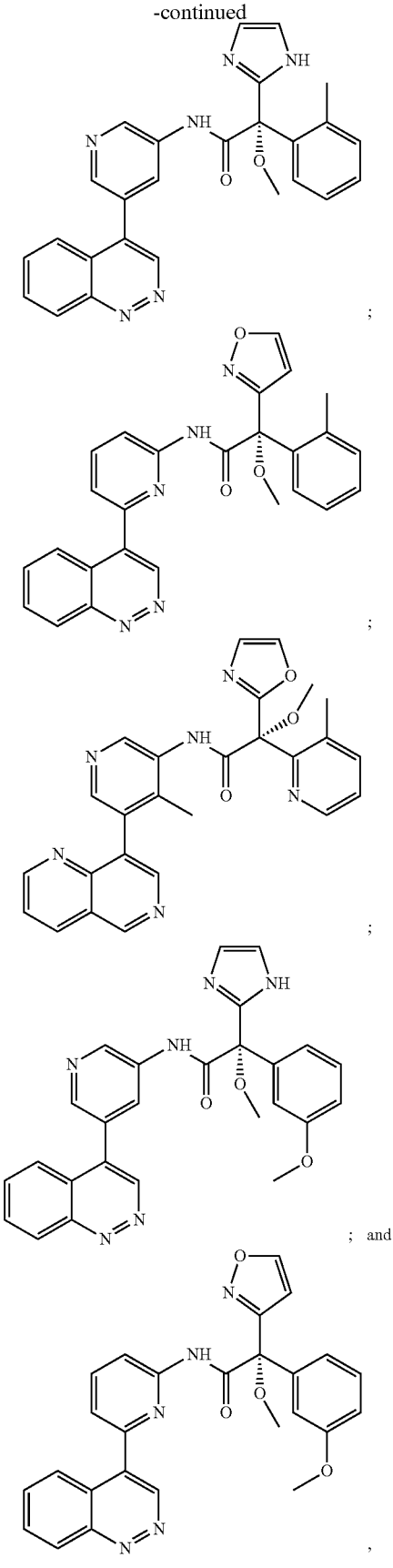
or a salt of any of the foregoing.
24. The compound of claim 1, wherein the compound is any one of:
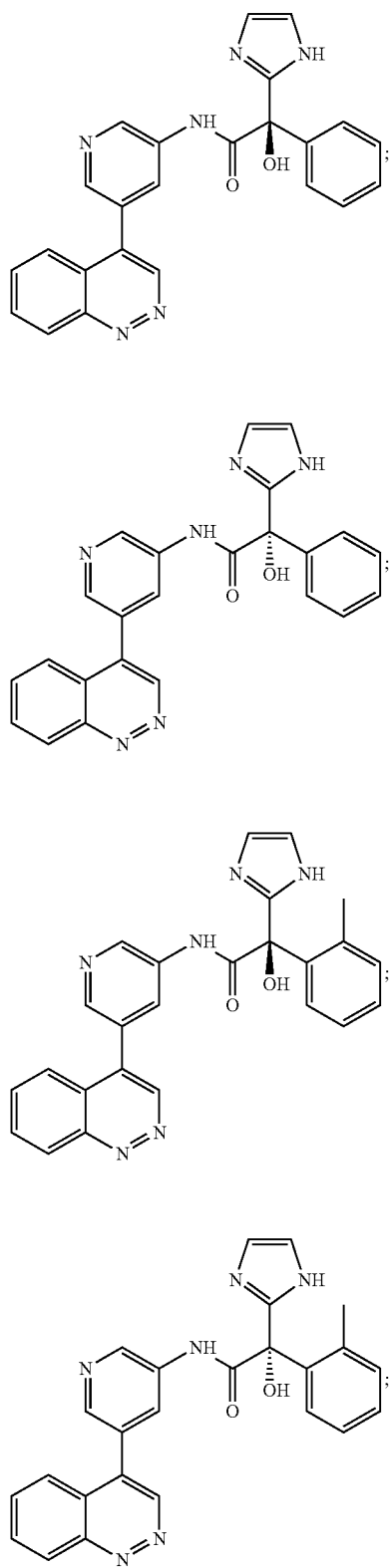

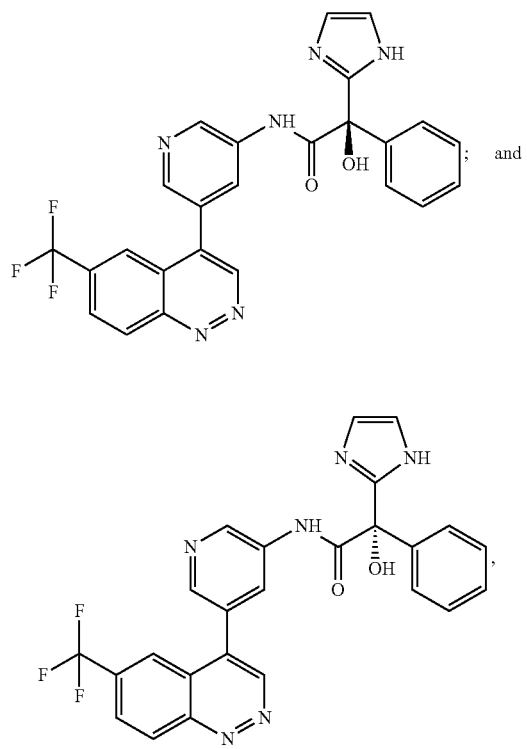

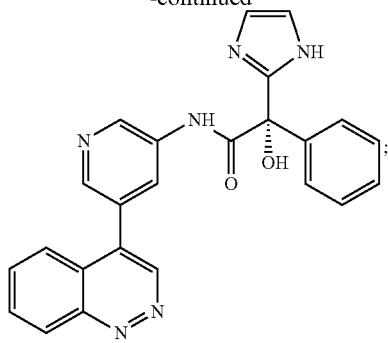

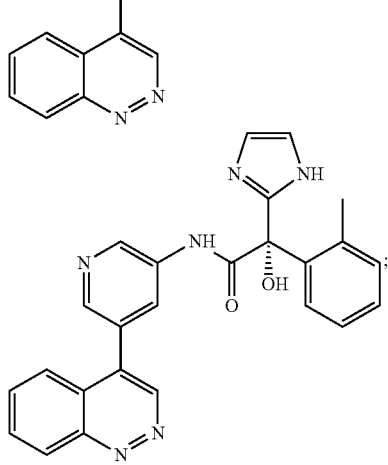

or a salt of any of the foregoing.

25. A method of treating a condition in an animal with a compound as recited in claim 1, the method comprising administering an effective amount of the compound to the animal, wherein the condition comprises at least one of nonalcoholic steatohepatitis, hyperglycemia, rheumatoid arthritis, psoriasis, inflammatory bowel disease, lupus, and multiple sclerosis.

26. The method of 25, wherein the condition is nonalcoholic steatohepatitis.

27. The method of claim 25, wherein the condition is type 1 diabetes.

28. The method of claim 25, wherein the compound is any one of:

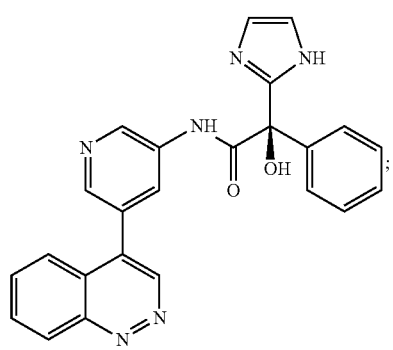

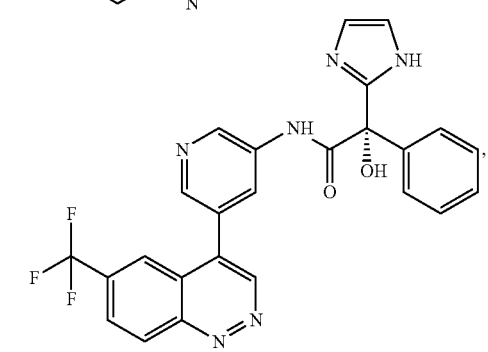

or a salt of any of the foregoing.

29. The method of claim 26, wherein the compound is any one of:
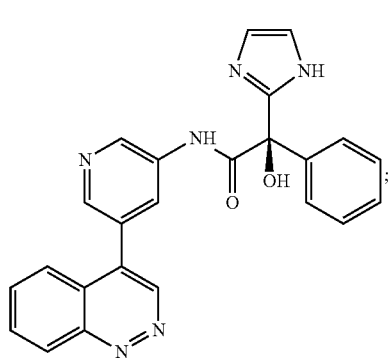
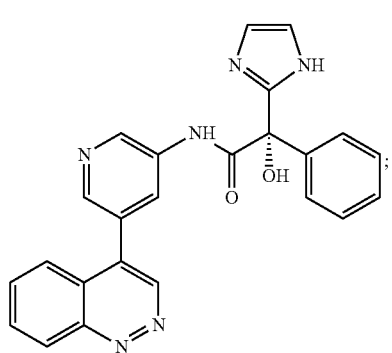
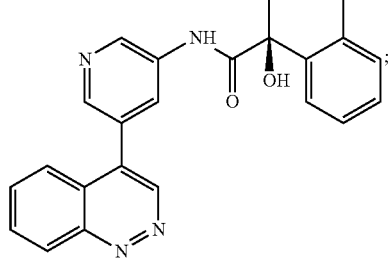
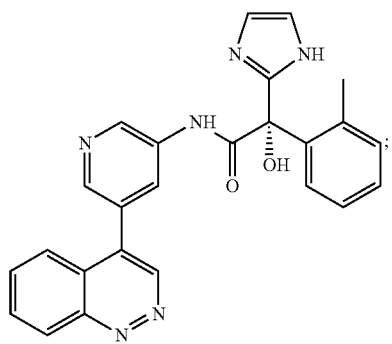
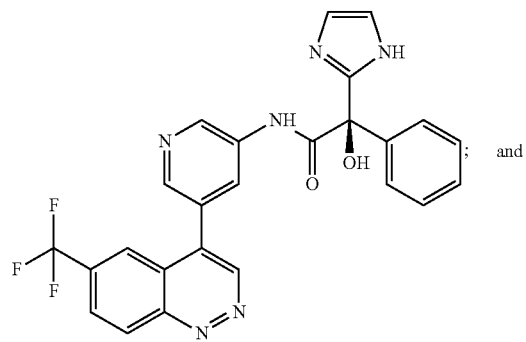
and
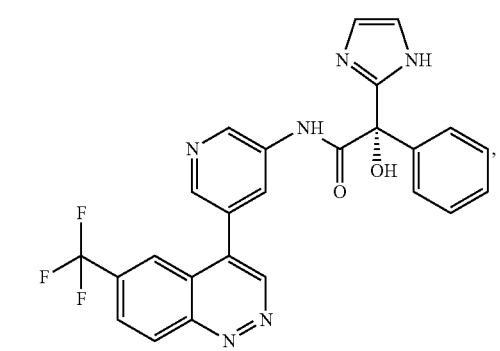 [SMILES: O=C(Nc1cncc(-c2cnnc3ccc(C(F)(F)F)cc23)c1)[C@](O)(c1ccccc1)c1ncc[nH]1]
or a salt of any of the foregoing.
30. The method of claim 27, wherein the compound is any one of:
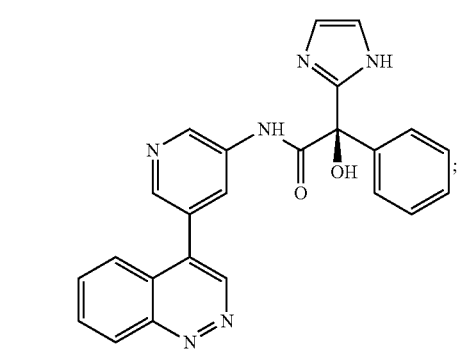
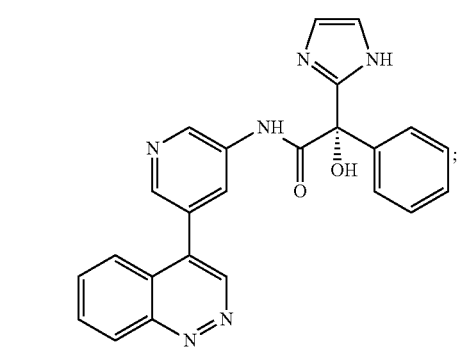

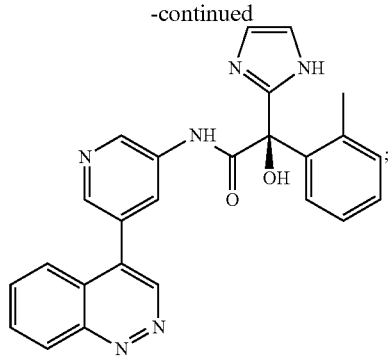
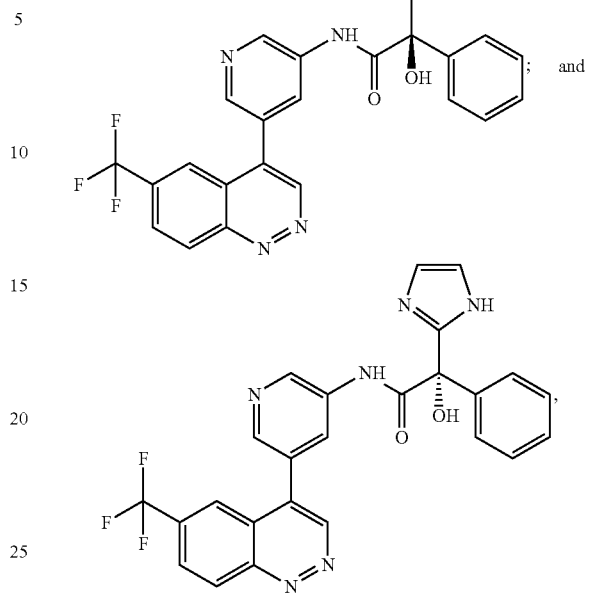
or a salt of any of the foregoing.
* * * * *